United States Patent
Sheps et al.

(10) Patent No.: US 11,076,958 B2
(45) Date of Patent: Aug. 3, 2021

(54) ANNULOPLASTY RING DELIVERY CATHETERS

(71) Applicant: Valtech Cardio, Ltd., Or Yehuda (IL)

(72) Inventors: Tal Sheps, Givat Shmuel (IL); Tal Hammer, Ramat Gan (IL); Tal Reich, Moledet (IL); Amir Gross, Tel Aviv-Jaffa (IL); Yuval Zipory, Modi'in (IL); Oz Cabiri, Hod Hasharon (IL); Yosef Gross, Moshav Mazor (IL)

(73) Assignee: Valtech Cardio, Ltd., Or Yehuda (IL)

( * ) Notice: Subject to any disclaimer, the term of this patent is extended or adjusted under 35 U.S.C. 154(b) by 409 days.

(21) Appl. No.: 15/977,271

(22) Filed: May 11, 2018

(65) Prior Publication Data
US 2018/0256334 A1   Sep. 13, 2018

Related U.S. Application Data

(63) Continuation of application No. 14/273,155, filed on May 8, 2014, now Pat. No. 9,968,452, which is a
(Continued)

(30) Foreign Application Priority Data

May 4, 2010  (WO) .................. PCT/IL2010/000358
Nov. 8, 2012  (WO) .................. PCT/IL2012/050451

(51) Int. Cl.
*A61F 2/24*   (2006.01)
*A61B 17/068*   (2006.01)
(Continued)

(52) U.S. Cl.
CPC .......... *A61F 2/2466* (2013.01); *A61B 17/068* (2013.01); *A61B 90/50* (2016.02);
(Continued)

(58) Field of Classification Search
CPC .............. A61M 25/104; A61M 25/003; A61M 2025/1045; A61F 2/954; A61F 2/958;
(Continued)

(56) References Cited

U.S. PATENT DOCUMENTS 3,604,488 A   9/1971   Wishart et al.
3,656,185 A   4/1972   Carpentier
(Continued)

FOREIGN PATENT DOCUMENTS

EP   1034753 A1   9/2000
EP   3531975 A1   9/2019
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Melanie R Tyson
*Assistant Examiner* — Chima U Igboko
(74) *Attorney, Agent, or Firm* — Thomas C. Richardson

(57) ABSTRACT

Apparatus is provided for repairing a cardiac valve, the apparatus including a catheter sized for delivery through vasculature of a subject and an elongated and flexible annuloplasty structure having an elongated lumen and an annuloplasty structure axis extending along the lumen. The annuloplasty structure is sized and configured for delivery to a heart of the subject through the catheter substantially along a catheter axis of the catheter while the annuloplasty structure axis is substantially parallel to the catheter axis. The apparatus also includes a plurality of anchors configured for delivery to a region of cardiac tissue from a proximal end of the catheter toward a distal end of the catheter and substantially along the annuloplasty structure axis and the catheter
(Continued)

axis while at least a portion of the annuloplasty structure is within a delivery passage of the catheter. Other embodiments are also described.

19 Claims, 43 Drawing Sheets

Related U.S. Application Data continuation-in-part of application No. 14/242,151, filed on Apr. 1, 2014, now Pat. No. 9,592,122, which is a continuation-in-part of application No. 14/357, 040, filed as application No. PCT/IL2012/050451 on Nov. 8, 2012, now Pat. No. 9,724,192, and a continuation-in-part of application No. PCT/IL2012/050451, filed on Nov. 8, 2012, and a continuation-in-part of application No. 13/319,030, filed as application No. PCT/IL2010/000358 on May 4, 2010, now Pat. No. 9,636,224, which is a continuation-in-part of application No. 12/689,635, filed on Jan. 19, 2010, now Pat. No. 8,545,553, and a continuation-in-part of application No. 12/689,693, filed on Jan. 19, 2010, now Pat. No. 8,911,494, and a continuation-in-part of application No. 12/548,991, filed on Aug. 27, 2009, now Pat. No. 8,808,368, and a continuation-in-part of application No. 12/437,103, filed on May 7, 2009, now Pat. No. 8,715,342, and a continuation of application No. 12/437,103, filed on May 7, 2009, now Pat. No. 8,715,342, and a continuation-in-part of application No. 12/435,291, filed on May 4, 2009, now Pat. No. 8,147,542.

(60) Provisional application No. 61/820,979, filed on May 8, 2013.

(51) Int. Cl.
    *A61B 90/50* (2016.01)
    *A61B 17/00* (2006.01)
    *A61B 17/064* (2006.01)

(52) U.S. Cl.
    CPC .............. *A61B 2017/00243* (2013.01); *A61B 2017/00327* (2013.01); *A61B 2017/0649* (2013.01); *A61B 2017/0688* (2013.01); *A61F 2/2445* (2013.01); *A61F 2220/0016* (2013.01); *A61F 2230/0013* (2013.01); *A61F 2250/0012* (2013.01)

(58) Field of Classification Search
    CPC .... A61F 2/2442; A61F 2/2445; A61F 2/2448; A61F 2/2451; A61F 2/2466; A61F 2/2469; A61F 2/2409; A61F 2/2457; A61B 2017/00782; A61B 2017/0409
    See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Ferrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,674,279 A | 10/1997 | Wright et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpenter et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |

(56) References Cited

U.S. PATENT DOCUMENTS

| | | |
|---|---|---|
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B1 | 9/2003 | Hlavka et al. |
| 6,626,899 B2 | 9/2003 | Houser |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,087,064 B1 | 6/2006 | Hyde |
| 7,077,850 B2 | 7/2006 | Kortenbach |
| 7,077,862 B2 | 7/2006 | Vidlund et al. |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Weber et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,562 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |

(56) References Cited

U.S. PATENT DOCUMENTS

| | | |
|---|---|---|
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,683,538 B2 | 3/2010 | To et al. |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,780,726 B2 | 6/2010 | Seguin |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,871,368 B2 | 1/2011 | Zollinger et al. |
| 7,871,433 B2 | 1/2011 | Lattouf |
| 7,883,475 B2 | 2/2011 | Dupont et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 * | 7/2011 | Webler .................. A61F 2/2451 623/2.36 |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,545,553 B2 | 10/2013 | Zipory et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,645,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |

(56) References Cited

U.S. PATENT DOCUMENTS

| | | |
|---|---|---|
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,724,084 B2 | 8/2017 | Groothuis et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kaftan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0187613 A1 | 8/2005 | Bolduc et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0184242 A1 | 6/2006 | Lichtenstein |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |

(56) References Cited

U.S. PATENT DOCUMENTS

| | | |
|---|---|---|
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270679 A1 | 11/2007 | Nguyen et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fenton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0222083 A1 | 9/2009 | Nguyen et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subrarnanian et al. |
| 2010/0121437 A1 | 5/2010 | Subrarnanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168827 A1 | 7/2010 | Schultz |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280604 A1 | 11/2010 | Zipory et al. |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106247 A1 | 5/2011 | Miller et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |

(56) References Cited

U.S. PATENT DOCUMENTS

| | | |
|---|---|---|
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1* | 3/2012 | Ellis .................. A61B 17/0644 600/104 |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1* | 9/2012 | Tuval .................. A61F 2/2409 623/2.37 |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243659 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351906 A1 | 12/2015 | Hammer et al. |
| 2015/0351910 A1 | 12/2015 | Gilmore et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0224489 A1 | 8/2017 | Starksen et al. |
| 2017/0245993 A1 | 8/2017 | Gross et al. |
| 2017/0325959 A1 | 11/2017 | Sheps et al. |
| 2018/0008409 A1 | 1/2018 | Kutzik et al. |
| 2018/0049875 A1 | 2/2018 | Iflah et al. |
| 2018/0168803 A1 | 6/2018 | Pesce et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowsk et al. |
| 2019/0038411 A1 | 2/2019 | Alon |
| 2019/0111239 A1 | 4/2019 | Bolduc et al. |
| 2019/0117400 A1 | 4/2019 | Mederna et al. |
| 2019/0125325 A1 | 5/2019 | Sheps et al. |
| 2019/0151093 A1 | 5/2019 | Keidar et al. |
| 2019/0175346 A1 | 6/2019 | Schaffner et al. |
| 2019/0183648 A1 | 6/2019 | Trapp et al. |
| 2019/0290260 A1 | 9/2019 | Caffes et al. |
| 2019/0290431 A1 | 9/2019 | Genovese et al. |
| 2019/0343633 A1 | 11/2019 | Garvin et al. |

FOREIGN PATENT DOCUMENTS

| | | |
|---|---|---|
| WO | 9205093 A1 | 4/1992 |
| WO | 9846149 A11 | 10/1998 |
| WO | 02085250 A3 | 2/2003 |
| WO | 03047467 A1 | 6/2003 |
| WO | 2010000454 A1 | 1/2010 |
| WO | 2010085649 A1 | 7/2010 |
| WO | 2011051942 A1 | 5/2011 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |

(56) References Cited

FOREIGN PATENT DOCUMENTS

WO          2019182645 A1     9/2019
WO          2019224814 A1    11/2019

OTHER PUBLICATIONS

Ahmadi, A., G. Spiliner, and Th Johannesson. "Hemodynarnic changes following experimental production and correction of acute mitral regurgitation with an adjustable ring prosthesis," The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees. (2000).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103, (2000).

Amplatzer Cardiac Plug brochure (English pages), AGA Medical Corporation (Plymouth, MN) (copyright 2008-2010, downloaded Jan. 11, 2011).

Amplatzero® Cribriforrn Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

Odell JA et al., "Early Results o4yf a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

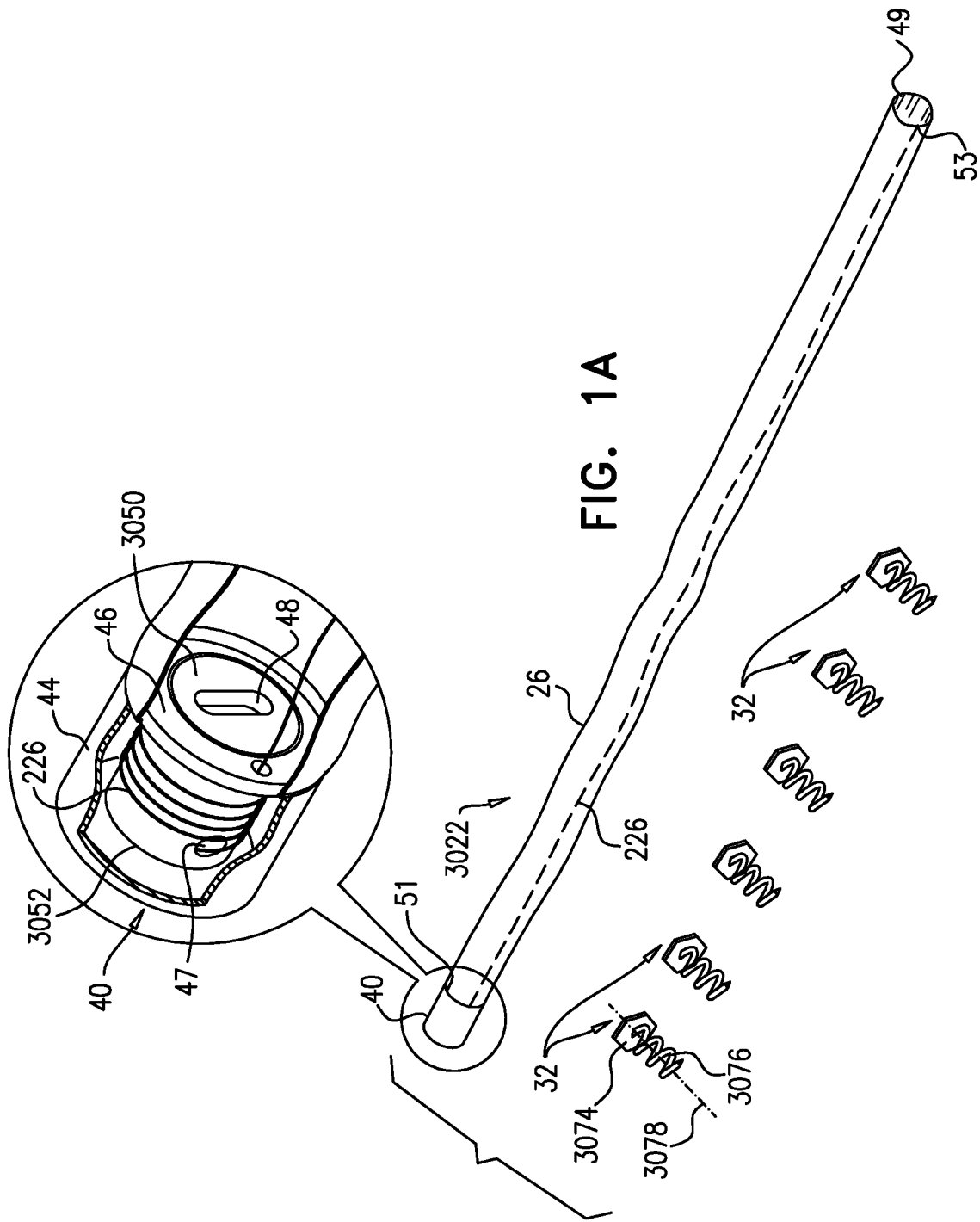

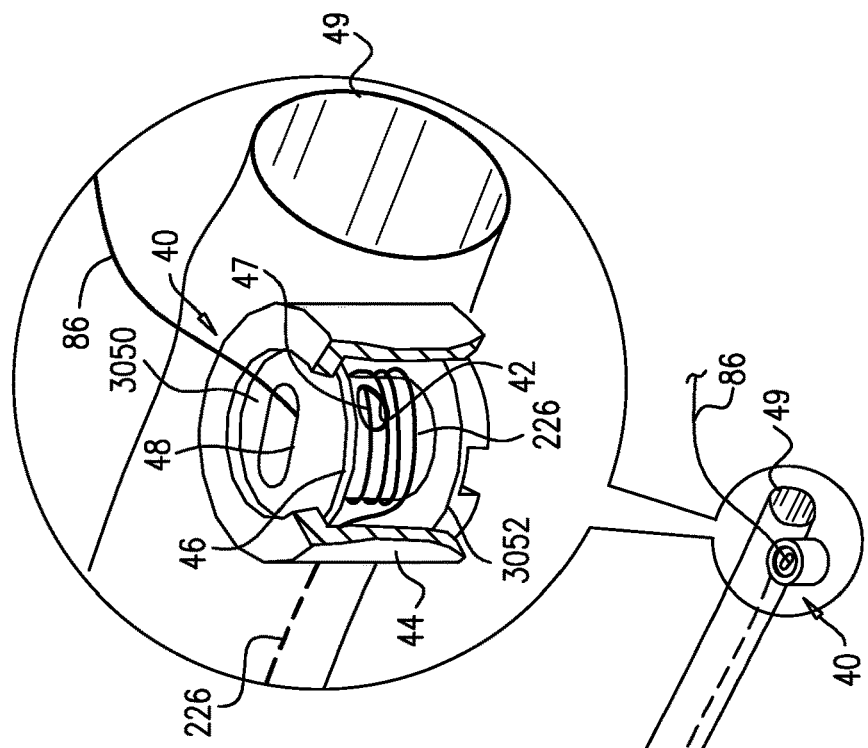
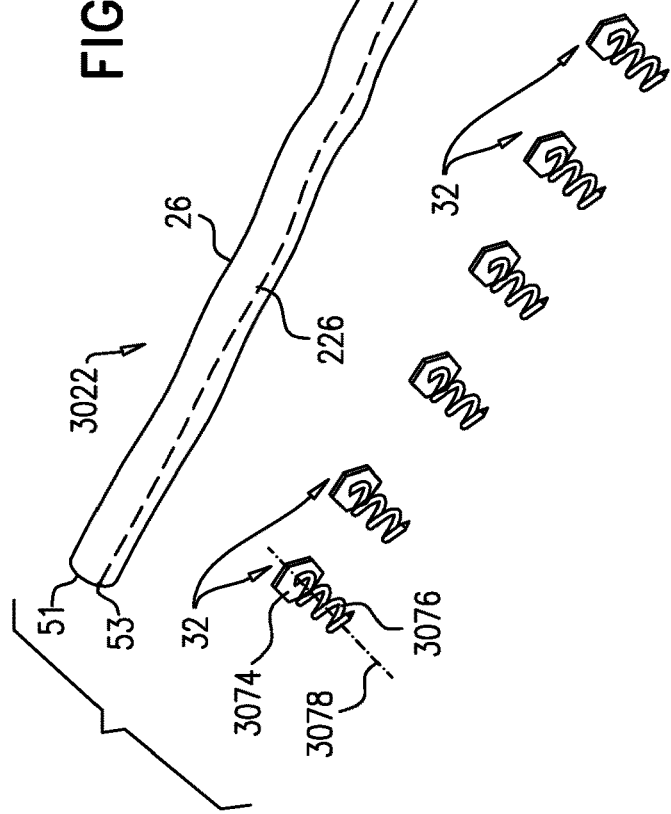
FIG. 1B

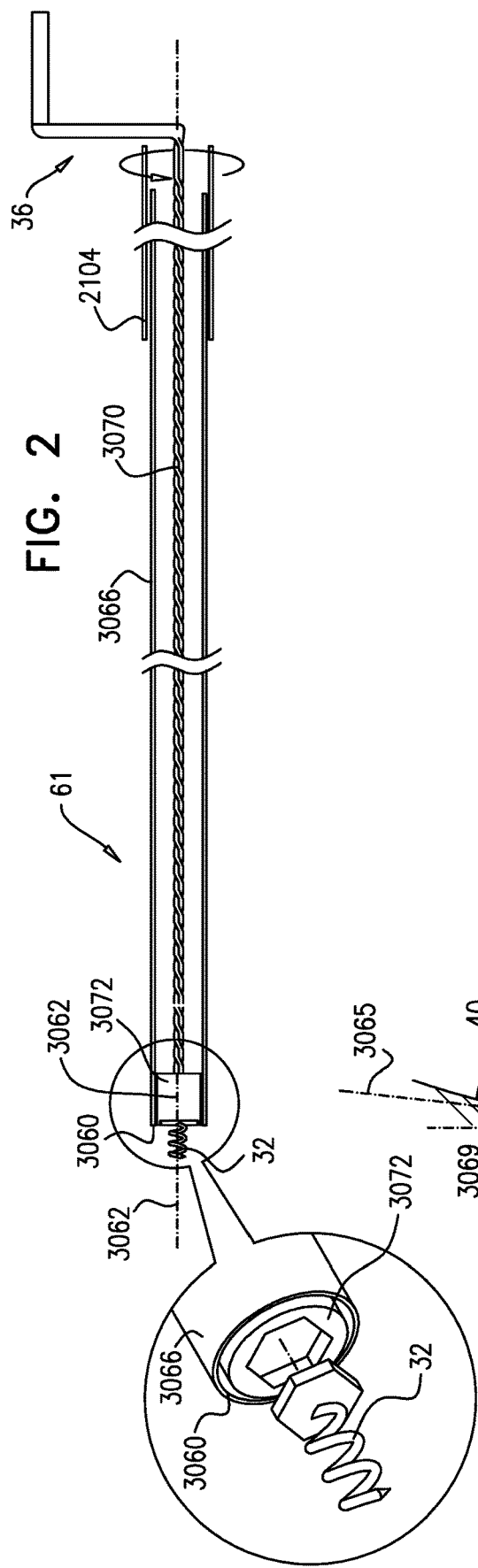
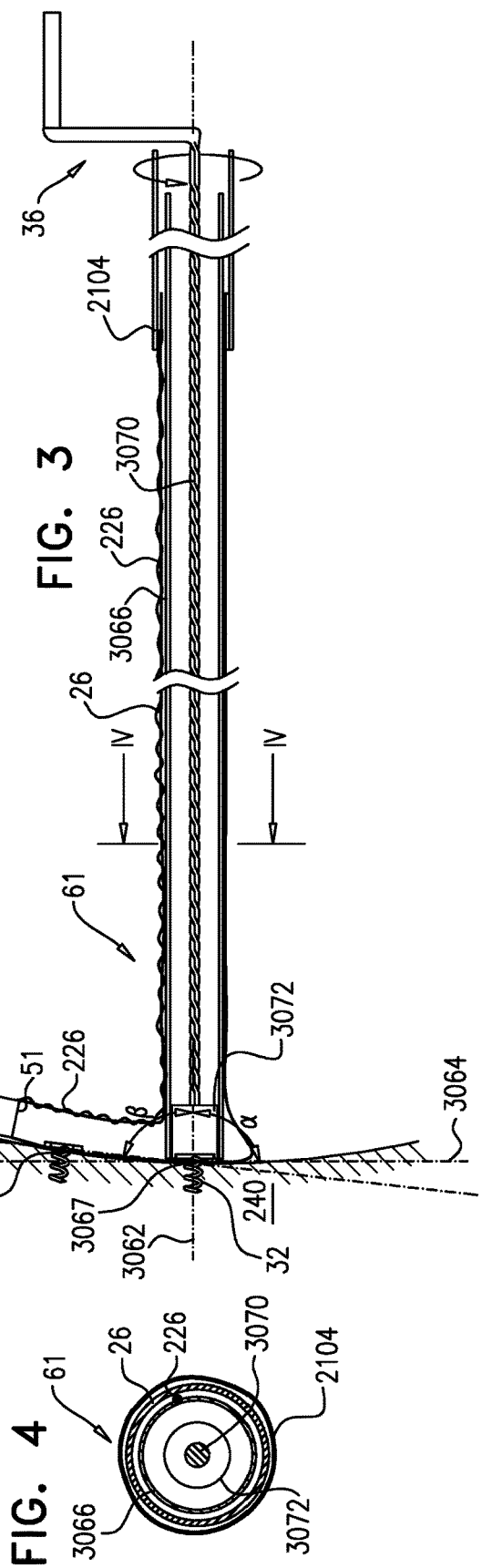
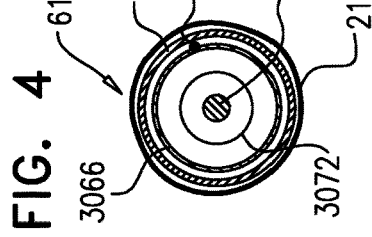

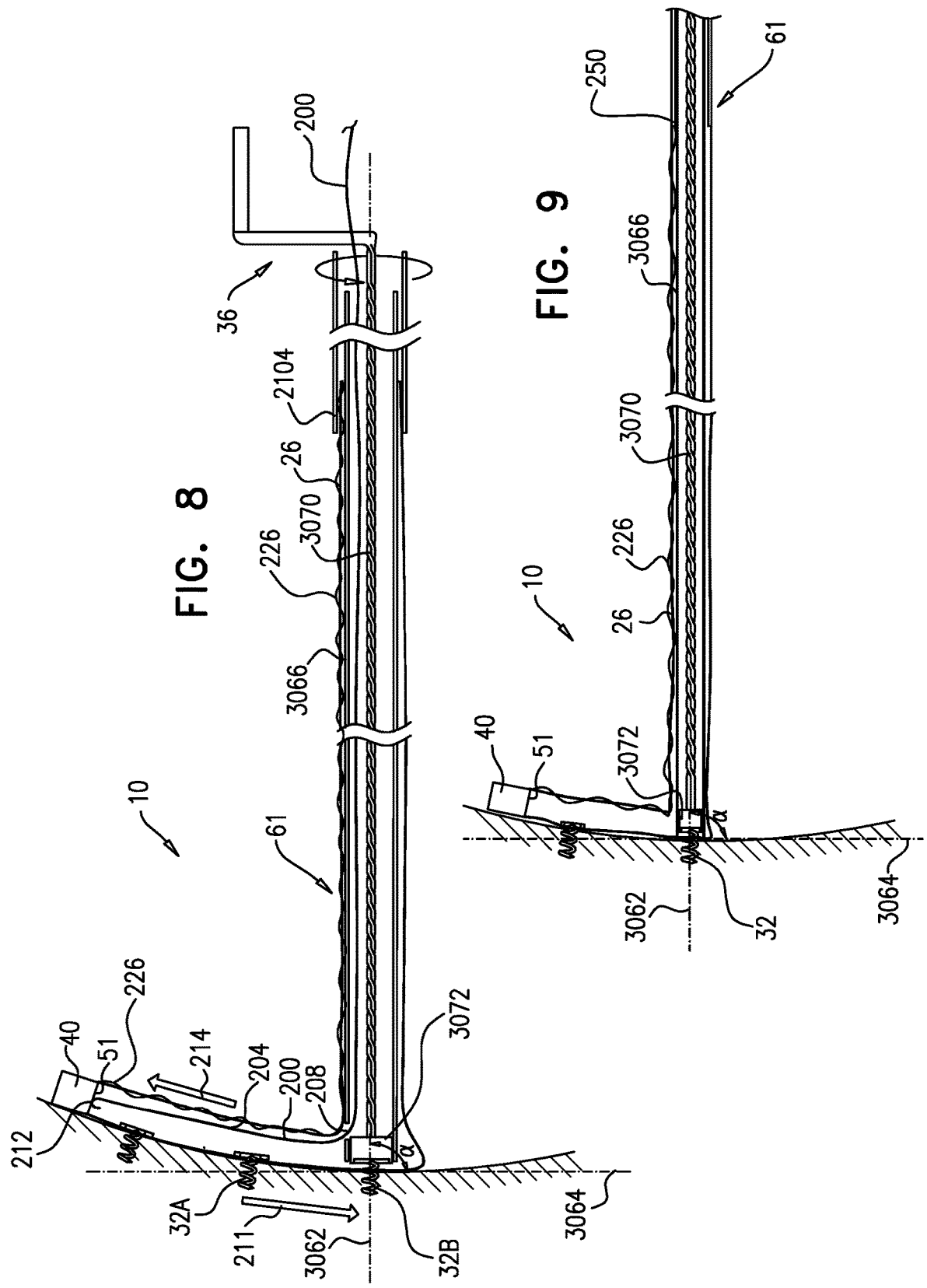

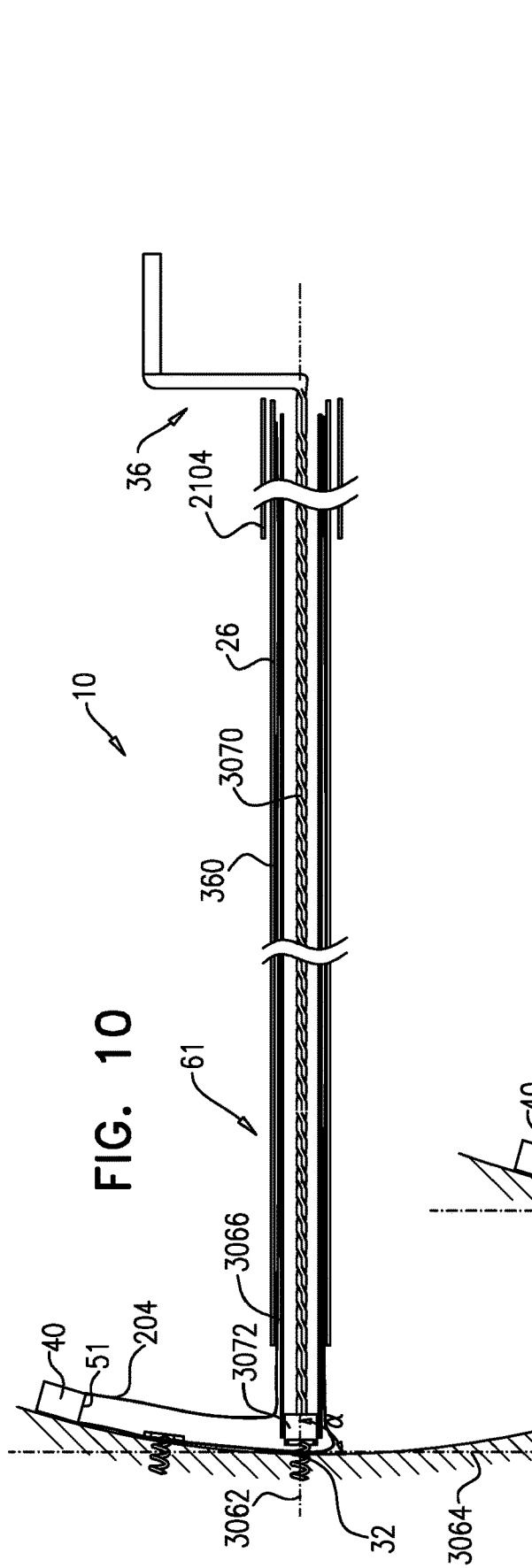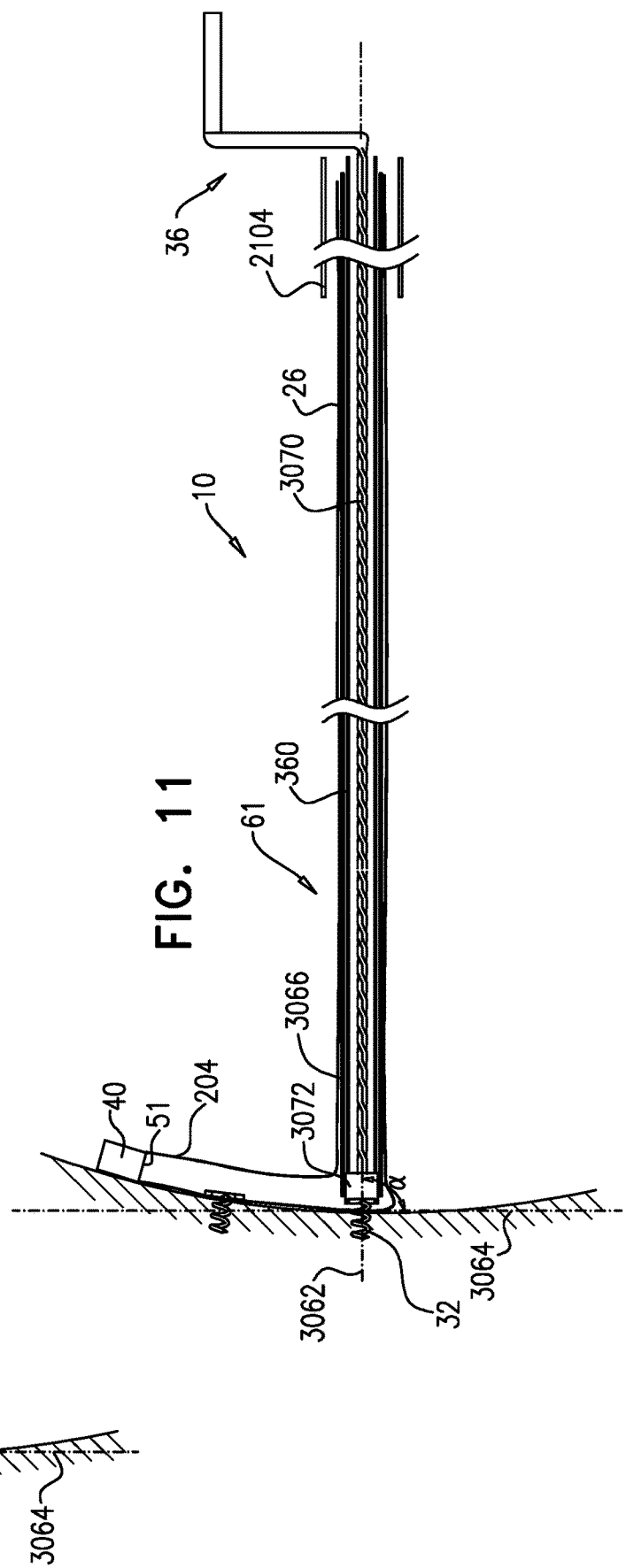

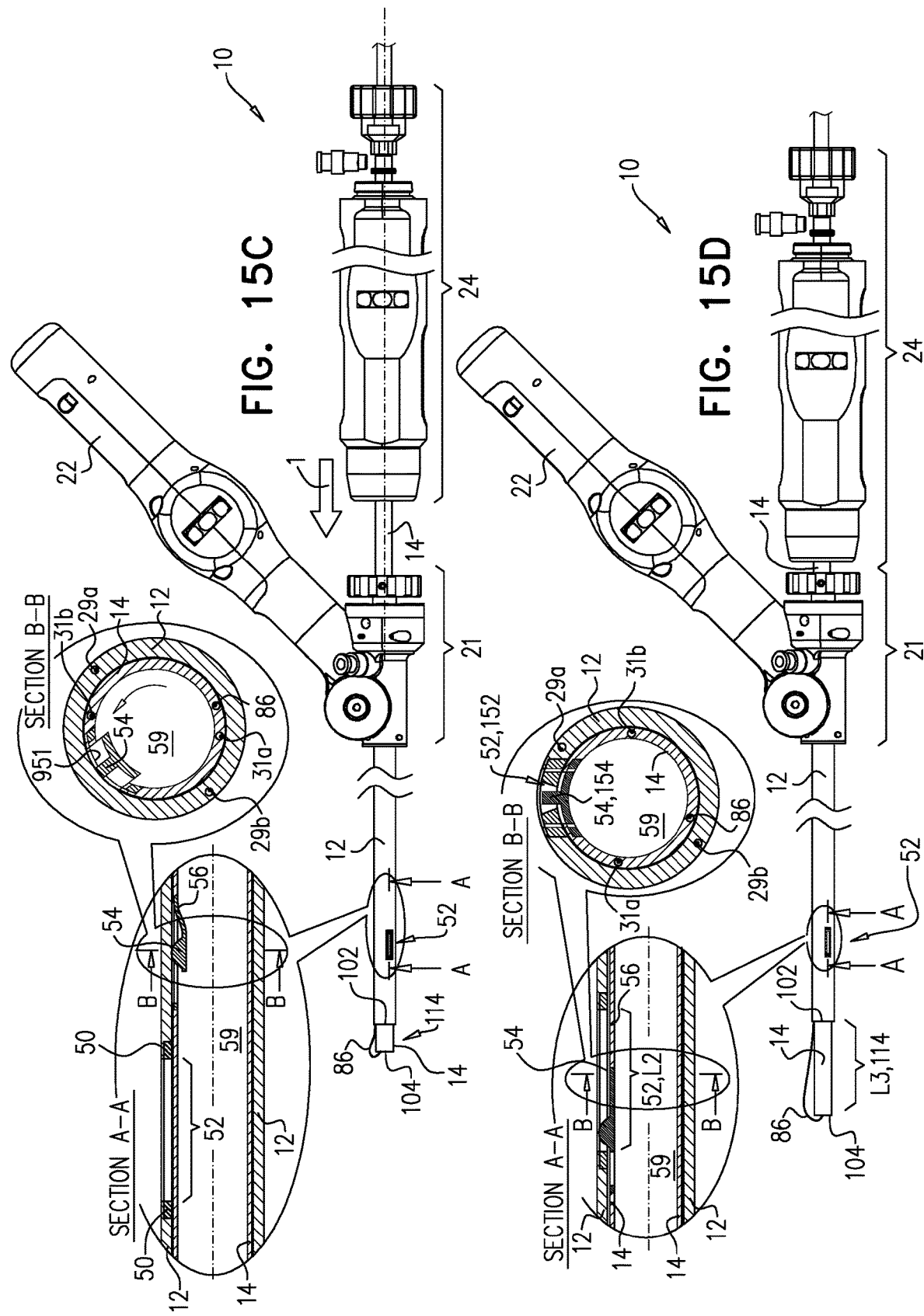

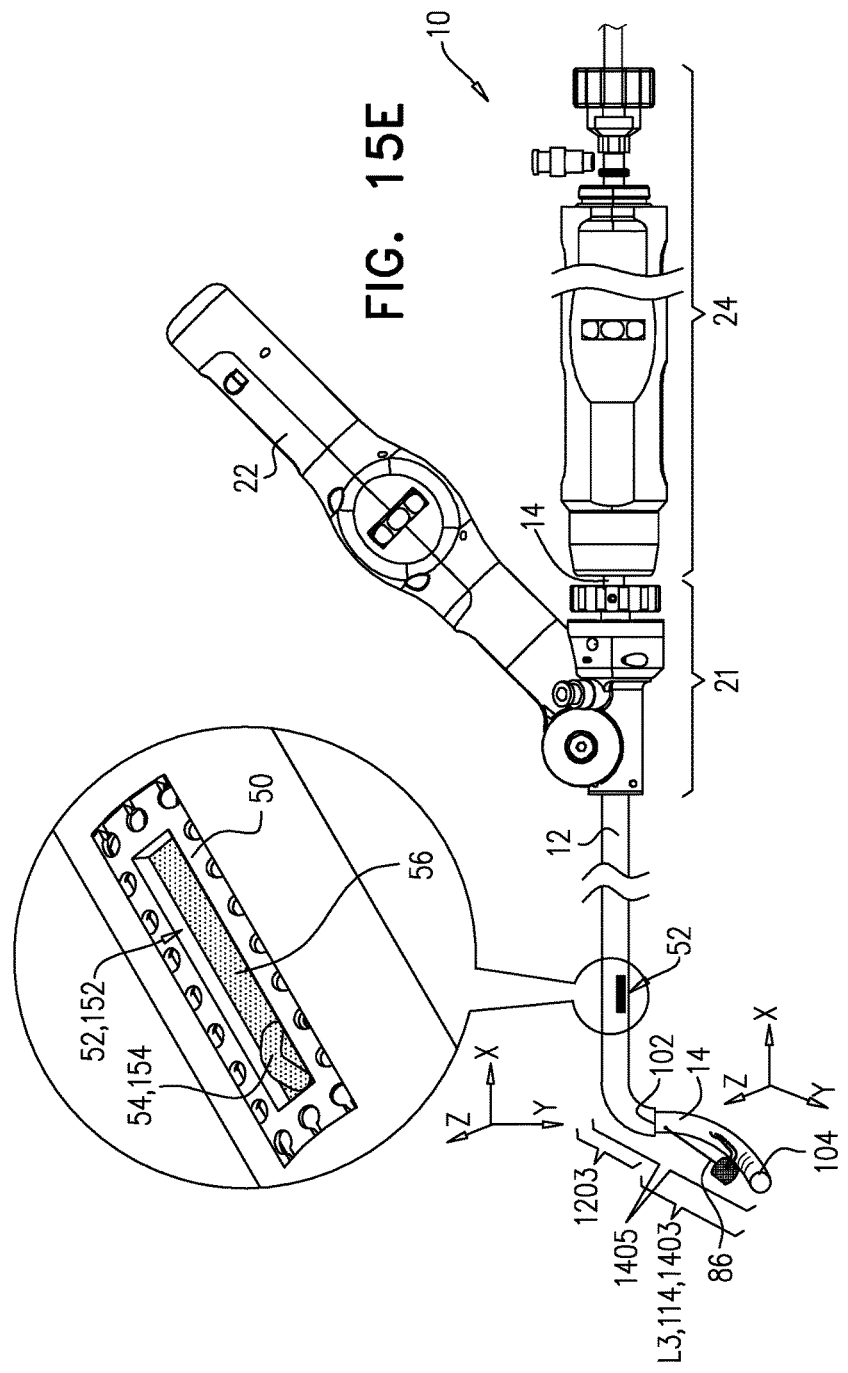

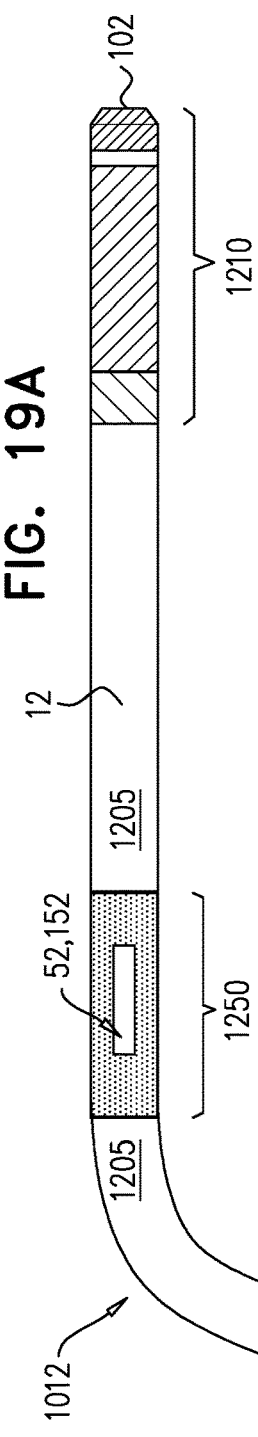
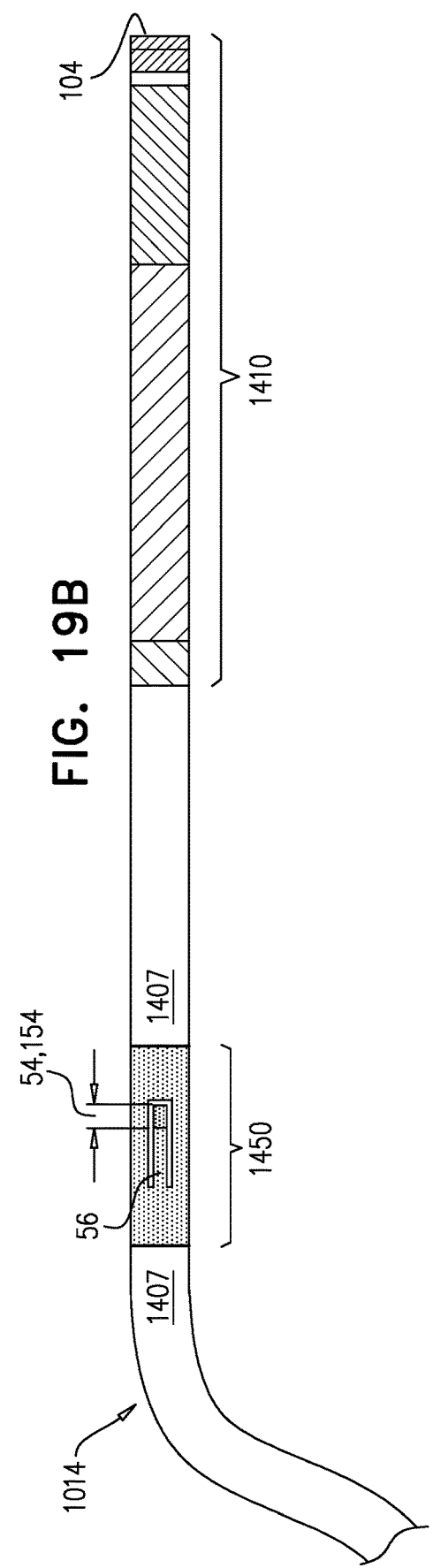

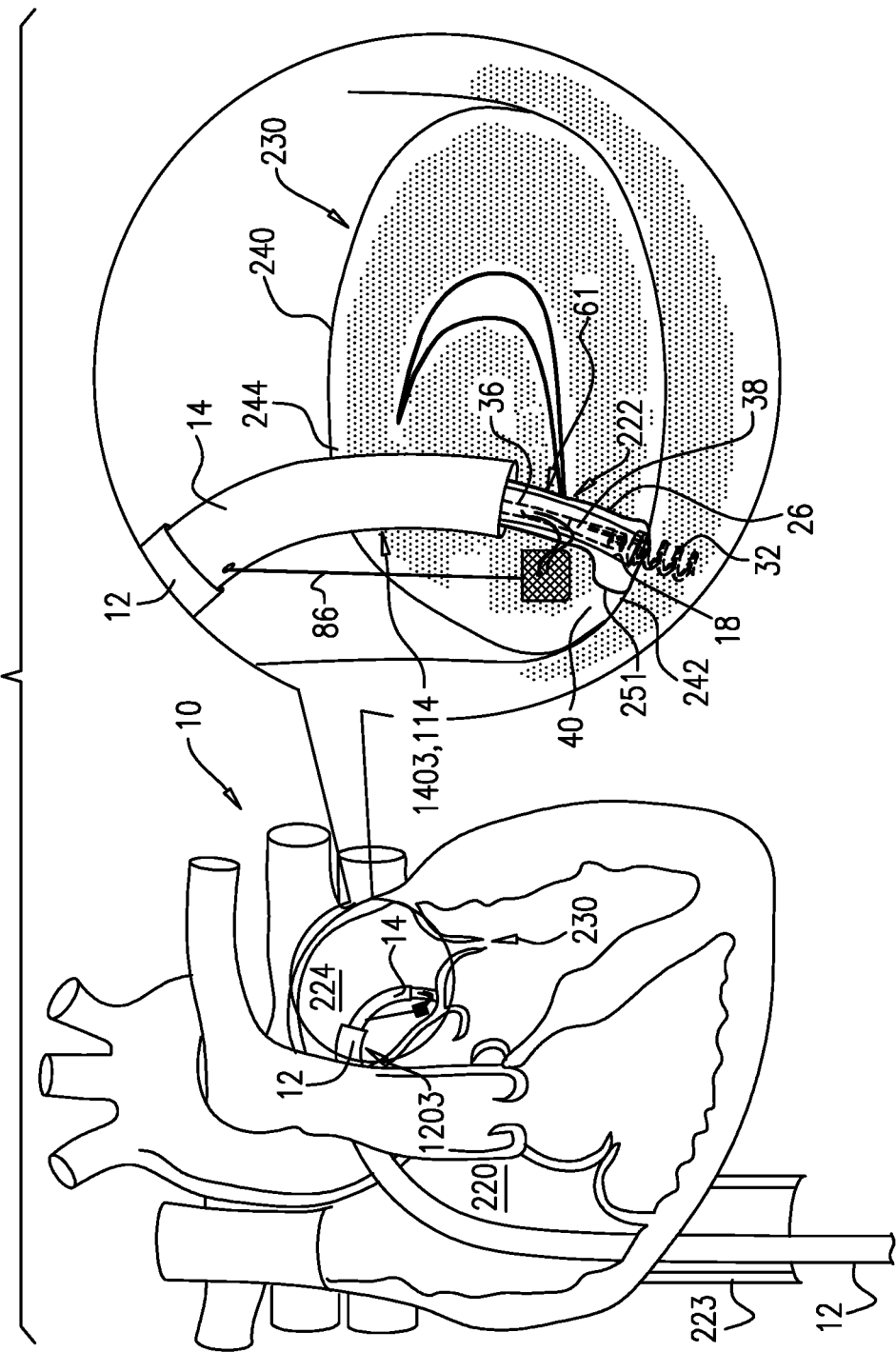

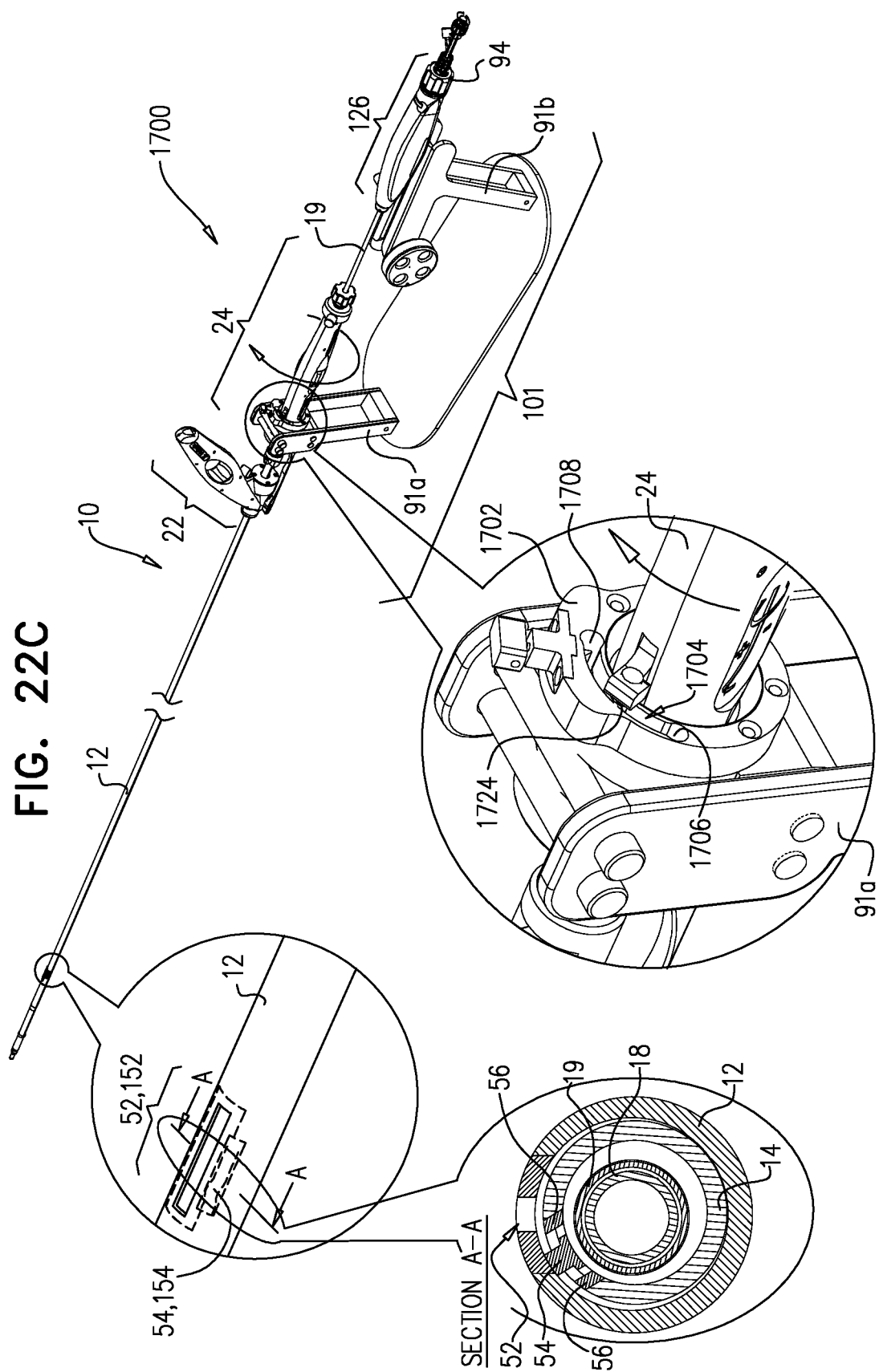

FIG. 23C
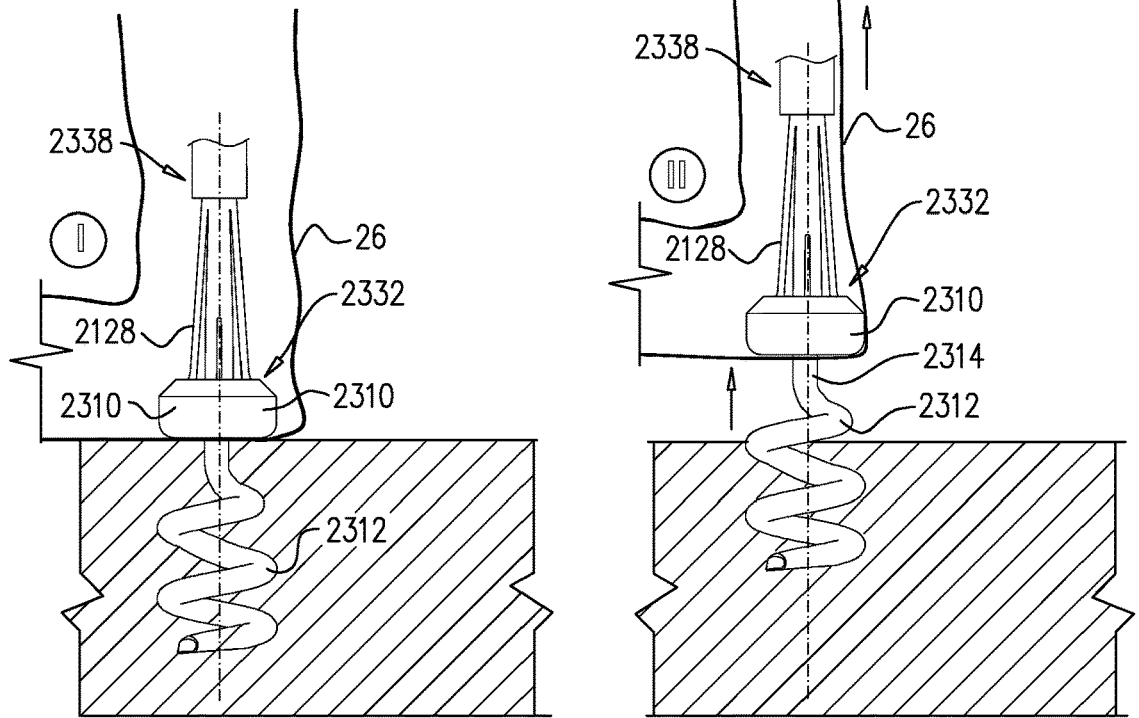
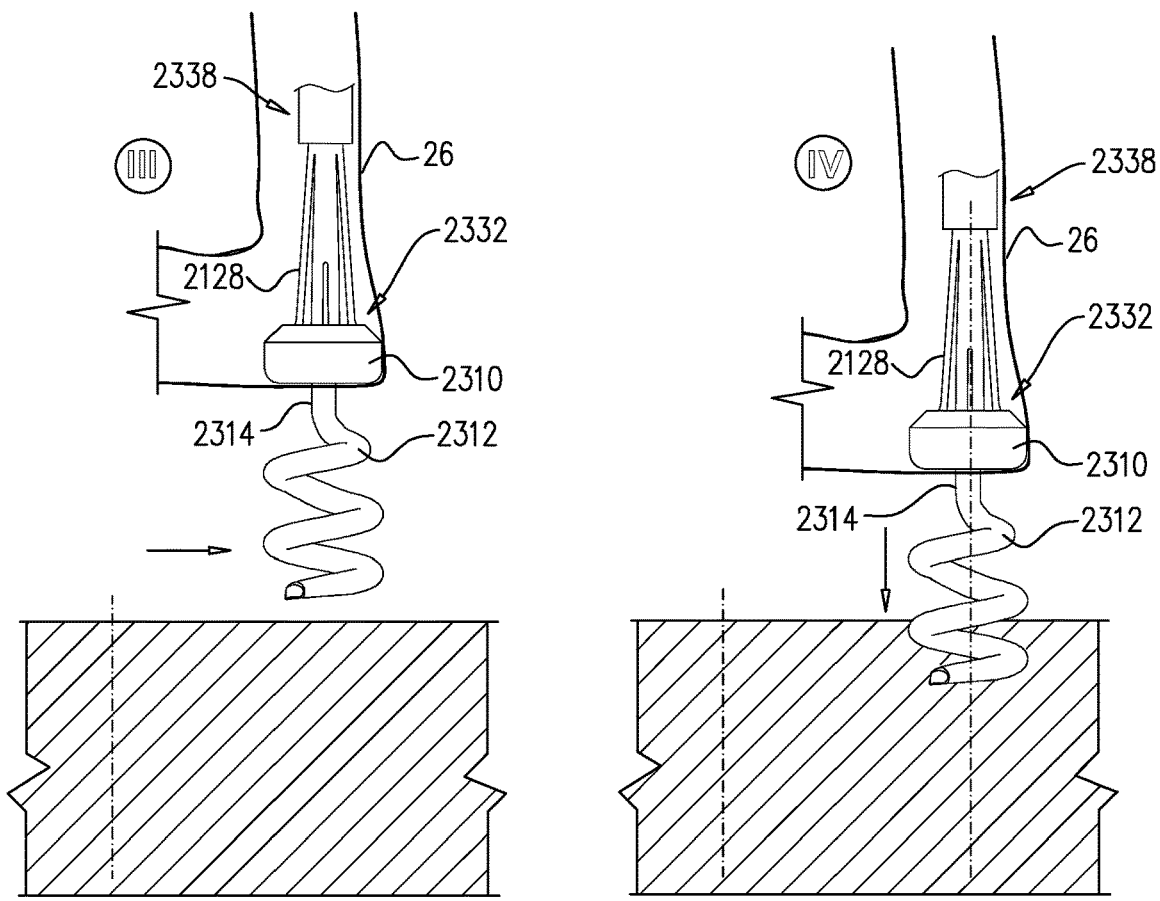

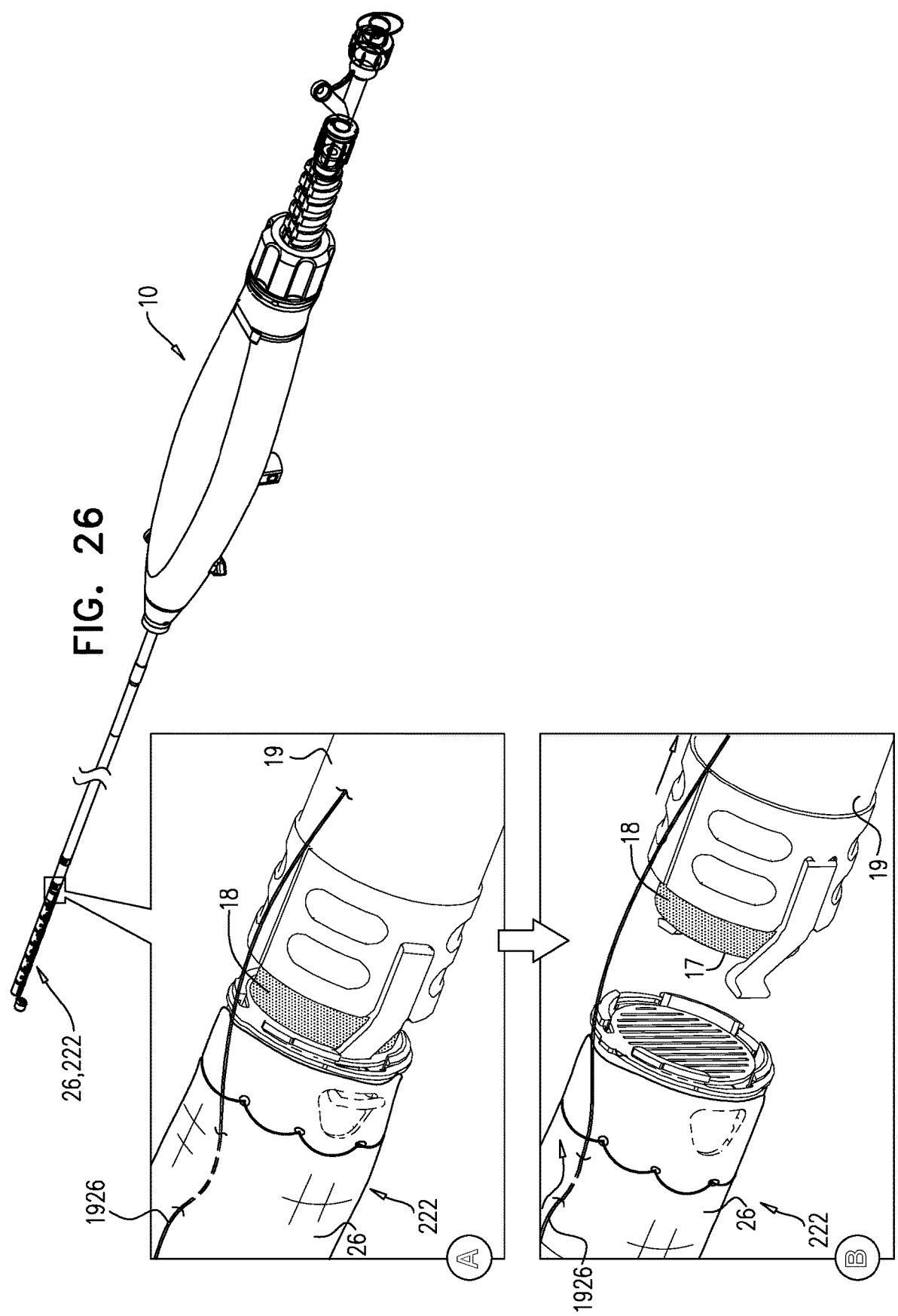

ANNULOPLASTY RING DELIVERY CATHETERS

CROSS-REFERENCES TO RELATED APPLICATIONS

The present application is a continuation application of U.S. patent application Ser. No. 14/273,155 to Sheps et al., entitled, "Annuloplasty ring delivery catheters," filed May 8, 2014 (U.S. Pat. No. 9,968,452), which:
  a. claims the priority from U.S. Provisional Patent Application 61/820,979 to Sheps et al., entitled, "Controlled steering functionality for implant-delivery tool," filed May 8, 2013, which is related to U.S. Provisional Patent Application 61/557,082 to Sheps et al., entitled, "Controlled steering functionality for implant-delivery tool," filed Nov. 8, 2011; U.S. Provisional Patent Application 61/717,303 to Sheps et al., entitled, "Controlled steering functionality for implant-delivery tool," filed Oct. 23, 2012; PCT Patent Application PCT/IL2012/050451 to Sheps et al., entitled, "Controlled steering functionality for implant-delivery tool," filed on Nov. 8, 2012, which published as WO/2013/069019; and U.S. Provisional Patent Application 61/745,848, to Sheps et al., entitled, "Controlled steering functionality for implant-delivery tool," filed Dec. 26, 2012;
  b. is a continuation-in-part of U.S. patent application Ser. No. 13/319,030 to Zipory et al., entitled, "Deployment techniques for annuloplasty ring and over-wire rotation tool, filed on Dec. 16, 2011, which published as US 2012/0078355, issued as U.S. Pat. No. 9,636,224, and is a U.S. national phase application of PCT Application PCT/IL2010/000358 to Zipory et al., entitled, "Deployment techniques for annuloplasty ring and over-wire rotation tool, filed on May 4, 2010, which published as WO 10/128503 and which:
    i. is a continuation-in-part of and claims the priority from U.S. patent application Ser. No. 12/435,291 to Maisano et al., entitled, "Adjustable repair chords and spool mechanism therefor," filed May 4, 2009, which issued as U.S. Pat. No. 8,147,542;
    ii. is a continuation-in-part of and claims the priority from U.S. patent application Ser. No. 12/437,103 to Zipory et al., entitled, "Annuloplasty ring with intra-ring anchoring," filed May 7, 2009, which issued as U.S. Pat. No. 8,715,342;
    iii. is a continuation-in-part of and claims the priority from U.S. patent application Ser. No. 12/548,991 to Maisano et al., entitled, "Implantation of repair chords in the heart," filed Aug. 27, 2009, which published as US 2010/0161042, and which issued as U.S. Pat. No. 8,808,368;
    iv. is a continuation-in-part of and claims the priority from U.S. patent application Ser. No. 12/689,635 to Zipory et al., entitled, "Over-wire rotation tool," filed on Jan. 19, 2010, which issued as U.S. Pat. No. 8,545,553; and
    v. is a continuation-in-part of and claims the priority from U.S. patent application Ser. No. 12/689,693 to Hammer et al., entitled, "Deployment techniques for annuloplasty ring," filed on Jan. 19, 2010, which published as US 2010/0280605, and which issued as U.S. Pat. No. 8,911,494;
  c. is a continuation-in-part of U.S. patent application Ser. No. 14/242,151 to Zipory et al., entitled, "Annuloplasty ring with intra-ring anchoring," filed Apr. 1, 2014, which published as US 2014/0343668, and which is a continuation of U.S. patent application Ser. No. 12/437, 103 to Zipory et al., entitled, "Annuloplasty ring with intra-ring anchoring," filed May 7, 2009, which issued as U.S. Pat. No. 8,715,342;
  d. is a continuation-in-part of PCT Patent Application PCT/IL2012/050451 to Sheps et al., entitled, "Controlled steering functionality for implant-delivery tool," filed on Nov. 8, 2012, which published as WO/2013/069019 and which claims priority from U.S. Provisional Patent Application 61/557,082 to Sheps et al., entitled, "Controlled steering functionality for implant-delivery tool," filed Nov. 8, 2011; and
  e. is a continuation-in-part of U.S. patent application Ser. No. 14/357,040 to Sheps et al., filed on May 8, 2014, which issued as U.S. Pat. No. 9,724,192, and which is a US national phase application of PCT Patent Application PCT/IL2012/050451 to Sheps et al., entitled, "Controlled steering functionality for implant-delivery tool," filed on Nov. 8, 2012, which published as WO/2013/069019 and which claims priority from U.S. Provisional Patent Application 61/557,082 to Sheps et al., entitled, "Controlled steering functionality for implant-delivery tool," filed Nov. 8, 2011.

All of these applications are incorporated herein by reference.

FIELD OF THE INVENTION

The present invention relates in general to valve repair, and more specifically to repair of an atrioventricular valve of a patient.

BACKGROUND OF THE INVENTION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

SUMMARY OF THE INVENTION

In some applications of the present invention, an adjustable partial annuloplasty ring is provided for repairing a dilated valve annulus of an atrioventricular valve, such as a mitral valve. The annuloplasty ring comprises a flexible sleeve and a plurality of anchors. An anchor deployment manipulator is advanced into a lumen of the sleeve, and, from within the lumen, deploys the anchors through a wall of the sleeve and into cardiac tissue, thereby anchoring the sleeve around a portion of the valve annulus. The anchors are typically deployed from a distal end of the manipulator while the distal end is positioned such that a central longitudinal axis through the distal end of the manipulator forms an angle with a surface of the cardiac tissue of between about 20 and 90 degrees, e.g., between about 45 and 90 degrees, e.g., between about 75 and 90 degrees, such as about 90 degrees. Typically, the anchors are deployed from the distal end of the manipulator into the cardiac tissue in a direction parallel to the central longitudinal axis through the distal end of the manipulator.

In some applications of the present invention, the anchors are deployed from the left atrium into the upper region of the ventricular wall near the atrium, tissue of which generally provides more secure anchoring than does the atrial wall. The above-mentioned angle of deployment enables such deployment into the upper region of the ventricular wall.

In some applications of the present invention, the anchor deployment manipulator comprises a steerable outer tube in which is positioned an anchor driver having an elongated, flexible shaft. Rotation of the anchor driver screws the anchors into the cardiac tissue. The anchors may, for example, be helical in shape. For some applications, the plurality of anchors are applied using the manipulator by loading a first one of the anchors onto the anchor driver, and deploying the anchor into the cardiac tissue. The anchor driver is withdrawn from the body of the subject, and a second one of the anchors is loaded onto the anchor driver. The anchor driver is reintroduced into the sleeve of the annuloplasty ring, and the second anchor is deployed. These steps are repeated until all of the anchors have been deployed. Alternatively, the anchor driver is configured to simultaneously hold a plurality of anchors, and to deploy them one at a time.

Typically, the manipulator is gradually withdrawn in a proximal direction during the anchoring procedure as anchors are deployed. The first anchor is thus deployed most distally in the sleeve (generally at or within a few millimeters of the distal tip of the sleeve), and each subsequent anchor is deployed more proximally.

The annuloplasty ring is typically configured to be placed only partially around the valve annulus (i.e., to assume a C-shape), and, once anchored in place, to be contracted so as to circumferentially tighten the valve annulus. To this end, the annuloplasty ring comprises a flexible contracting member such as a wire, which is typically positioned within the lumen of the sleeve. The annuloplasty ring further comprises an adjustment mechanism which facilitates contracting of the annuloplasty ring. For some applications, the adjustment mechanism comprises a spool to which a first end of the contracting member is coupled. The spool is positioned in a vicinity of either the proximal or the distal end of the sleeve. A second end of the contracting member is coupled to the sleeve in a vicinity of the end of the sleeve opposite the end to which the spool is positioned. Rotation of the spool winds a portion of the contracting member around the spool, thereby pulling the far end of the ring toward the spool and tightening the ring. For some applications, the spool is positioned in a vicinity of the distal end of the sleeve, and is oriented such that a driving interface thereof is accessible from within the sleeve. A screwdriver tool is inserted into the sleeve, and used to rotate the spool via the driving interface of the spool.

All of the tools and elements of the annuloplasty system that are introduced into left atrium are contained within the sleeve of the annuloplasty ring, which reduces the risk that any elements of the system will accidentally be released to the blood circulation, or damage surrounding tissue. In addition, the lumen of the sleeve provides guidance if it should be necessary to return to a previously deployed anchor, such as to tighten, loosen, remove, or relocate the anchor. For some applications, the anchors comprise helical screws, which facilitate such adjusting or removing.

The annuloplasty ring may be advanced toward the annulus of a valve in any suitable procedure, e.g., a transcatheter procedure, a minimally invasive procedure, or an open heart procedure.

In some applications of the present invention, a multi-component tubular system is provided for accessing a heart of a patient. The system comprises one or more steerable guiding catheters configured for directing the passage of devices therethrough into the heart. The multi-component tubular system is configured to deliver an implant in a desired orientation to an annulus of a cardiac valve of the patient and to facilitate anchoring of the implant to the annulus. For some applications of the present invention, the guiding system is advanced transluminally or transthoracically accessing an atrium of the heart. Typically, the system comprises two or more steerable catheters. A first catheter has a distal portion that is steerable to a first desired spatial orientation. A second catheter is disposed within the first catheter and has a distal portion that is steerable to a second desired spatial orientation. The system provides techniques and relative-spatial-orientation-controlling devices for controlling the orientation of the distal portion of the second catheter with respect to the first catheter without substantially distorting the first spatial orientation of the distal portion of the first catheter. For some applications, the relative-spatial-orientation-controlling device comprises a rotational locking mechanism provided by components of the catheter system.

For some applications, the first catheter is configured to provide a slit at the distal portion thereof (i.e., a first component of the rotational locking mechanism), and the second catheter is configured to provide a depressible pin (i.e., a second component of the rotational locking mechanism) at a distal portion thereof. The second catheter is configured for advancement through a lumen of the first catheter. During the advancement, the pin is depressed by an inner wall of the first catheter. The pin is configured to return to a resting state in which the pin is not depressed, when the pin is aligned with the slit of the first catheter. Since the first catheter provides the slit at a distal portion thereof, the second catheter may be introduced within the lumen of the first catheter in any suitable rotational orientation with respect to the first catheter.

The distal portion of the first catheter may be steered in a suitable direction following advancement of the first catheter through vasculature of the patient. Following the advancement of the first catheter and steering of the distal portion of the first catheter in any one or more suitable planes, the second catheter is advanced through the first catheter. The second catheter is advanced through the first catheter until at least a distal-most portion of the distal portion of the second catheter is exposed from within the lumen of the first catheter. Depending on the relative rotational orientation of the second catheter with respect to the first catheter, the physician may need to rotate the second catheter in order to engage the pin with the slit and lock the second catheter with respect to the first catheter. Such locking enables steering of the distal portion of the second catheter in any one or more suitable planes with respect to the distal portion of the first catheter in a manner which substantially maintains the spatial and rotational orientation of the first catheter during the steering of the second catheter. With such a rotational locking, during steering of the second catheter, the second catheter will not tend to assume the rotational configuration and angular, curved orientation of the first catheter, and vice versa. Additionally, the first catheter may be further steered without substantially disrupting the spatial, angular, and rotational orientation of the distal portion of the second catheter, and vice versa.

There is therefore provided, in accordance with some applications of the present invention, apparatus for use with a subject, the apparatus including:
- a first catheter, shaped to define a first lumen therethrough, a distal end portion of the first catheter being transluminally advanceable to a vicinity of an anatomical site;
- a second catheter, shaped to define a second lumen therethrough, a distal end portion of the second catheter being advanceable through the first lumen and out of a distal end of the first lumen; and
- a longitudinal implant, advanceable through at least part of the second lumen and out of a distal end of the second lumen, the first and second catheters are assembled:
  - to facilitate sliding of the second catheter within the first catheter, and sliding of the implant within the second catheter,
  - to configure the first catheter, the second catheter, and the implant to assume a multi-bend formation in which:
    - a first bend of the formation separates a first domain of the formation from a second domain of the formation,
    - a second bend of the formation separates the second domain of the formation from a third domain of the formation,
    - the first domain includes at least (1) part of the first catheter and (2) part of the second catheter,
    - the second domain includes the distal end portion of the second catheter, part of the implant, and none of the first catheter, and
    - the third domain includes part of the implant, none of the first catheter, and none of the second catheter.

In some applications of the present invention, a third bend of the formation separates the first domain from a fourth domain, and the fourth domain includes at least (1) part of the first catheter and (2) part of the second catheter.

In some applications of the present invention, the first catheter, the second catheter and the implant are transluminally advanceable such that at least the second domain and the first domain are disposed within a heart atrium of the subject.

In some applications of the present invention, the first domain of the multi-bend formation includes part of the first catheter, part of the second catheter, and part of the implant.

In some applications of the present invention, the apparatus further includes a proximal extracorporeal portion that is configured to facilitate the sliding of the second catheter within the first catheter, and the sliding of the implant within the second catheter, and to configure the first catheter, the second catheter and the implant to assume the multi-bend formation.

In some applications of the present invention, the apparatus further includes:
- a first locking mechanism located at respective distal portions of the first and second catheters, the first locking mechanism being configured to rotationally lock the first catheter with respect to the second catheter at the respective distal portions; and
- a second locking mechanism, the proximal extracorporeal portion including the second locking mechanism, the second locking mechanism being configured to rotationally lock the first catheter with respect to the second catheter at the proximal extracorporeal portion.

In some applications of the present invention, the first locking mechanism includes a detent at the distal portion of the second catheter, and the second catheter is shaped so as to define a slit at the distal portion thereof for engaging the detent of the first catheter to lock the second catheter to the first catheter.

In some applications of the present invention, the second locking mechanism includes a housing coupled to the first catheter, the housing being shaped so as to define a groove, and the second catheter is shaped so as to define a protrusion at a proximal portion thereof for engaging the groove of the housing to lock the second catheter to the first catheter.

In some applications of the present invention, the first and the second locking mechanisms are configured to lock substantially simultaneously.

In some applications of the present invention, the proximal extracorporeal portion is configured to bend the distal end portion of the first catheter.

In some applications of the present invention, when the distal end portion of the second catheter is disposed outside of the distal end of the first lumen, the proximal extracorporeal portion is configured to bend the distal end portion of the second catheter independently of bending of the distal end portion of the first catheter.

In some applications of the present invention, the proximal extracorporeal portion is configured to steer the first catheter.

In some applications of the present invention, the proximal extracorporeal portion is configured to steer the second catheter.

In some applications of the present invention, the proximal extracorporeal portion includes:
- a first control mechanism configured to steer the first catheter; and
- a second control mechanism configured to steer the second catheter;
- the first control mechanism and the second control mechanism are configured to control relative movement of the annuloplasty structure, by controlling the first and second catheters, respectively.

In some applications of the present invention, the apparatus further includes at least one tissue anchor configured for implantation through at least a portion of a wall of the implant while at least a portion of the implant is within the second lumen of the second catheter.

In some applications of the present invention, the at least one tissue anchor is configured to anchor a distal end portion of the longitudinal implant to tissue of the subject, and the tissue anchor facilitates the formation of the second bend.

In some applications of the present invention, the apparatus further includes a channel having an opening at a distal end thereof, the channel being advanceable within a lumen of the implant, the channel is configured to sandwich the portion of the wall of the implant between (1) the opening in the channel, and a (2) region of cardiac tissue.

In some applications of the present invention, the at least one tissue anchor is configured to anchor a distal end portion of the longitudinal implant to tissue of the subject, and the tissue anchor and the channel facilitate the formation of the second bend.

In some applications of the present invention, the channel is steerable.

In some applications of the present invention, the tissue anchor is configured to be deployed from the opening and through the portion of the wall during the sandwiching.

In some applications of the present invention, the apparatus further includes an adjustment mechanism coupled to the implant at a distal portion of the implant at the third domain, the adjustment mechanism being configured to adjust a degree of tension of the implant.

In some applications of the present invention, the apparatus further includes a guide member that is reversibly coupled to the adjustment mechanism at a distal portion of the guide member, a generally-triangular shape is formed in the apparatus between: (1) the guide member, (2) the distal portion of the implant structure at at least a portion of the third domain, and (3) at least a portion of the second domain.

In some applications of the present invention, the apparatus further includes a channel having an opening at a distal end thereof, the channel being advanceable within a lumen of the implant, the second domain includes a distal end portion of the channel, and a generally-triangular shape is formed in the apparatus between: (1) the guide member, (2) the distal portion of the implant structure at at least a portion of the third domain, and (3) the distal end portion of the channel.

In some applications of the present invention, the first and second catheters are independently steerable.

There is further provided, in accordance with some applications of the present invention, a method including:
  transluminally advancing to a vicinity of an anatomical site a distal end portion of a first catheter, shaped to define a first lumen therethrough;
  advancing a distal end of a second catheter through the first lumen of the first catheter, the second catheter being shaped to define a second lumen therethrough;
  advancing a longitudinal implant through at least part of the second lumen and out of a distal end of the second lumen;
  facilitating sliding of the second catheter within the first catheter, and sliding of the implant within the second catheter; and
  configuring the first catheter, the second catheter, and the implant to assume a multi-bend formation in which:
    a first bend of the formation separates a first domain of the formation from a second domain of the formation,
    a second bend of the formation separates the second domain of the formation from a third domain of the formation,
    the first domain includes at least (1) part of the first catheter and (2) part of the second catheter,
    the second domain includes the distal end portion of the second catheter, part of the implant, and none of the first catheter, and
    the third domain includes part of the implant, none of the first catheter, and none of the second catheter.

In some applications of the present invention, the method further includes:
  advancing through a lumen of the implant a channel having an opening at a distal end thereof; and
  sandwiching the portion of the wall of the implant between (1) the opening in the channel, and a (2) region of cardiac tissue.

In some applications of the present invention, deploying the tissue anchor includes deploying the tissue anchor from the opening and through the portion of the wall during the sandwiching.

There is yet further provided, in accordance with some applications of the present invention, apparatus for repairing a cardiac valve, the apparatus including:
  a catheter sized for delivery through vasculature of a subject, the catheter defining a delivery passage and having an elongated catheter axis extending therethrough;
  an elongated and flexible annuloplasty structure having an elongated lumen therein and a structure axis extending along the lumen, the annuloplasty structure is sized and configured for delivery to the heart through the catheter substantially along the catheter axis while the structure axis is substantially parallel to the catheter axis; and
  a plurality of anchors, configured for delivery to a region of cardiac tissue from a proximal end of the catheter toward a distal end of the catheter and substantially along the structure axis and the catheter axis while at least a portion of the annuloplasty structure is within the passage of the catheter.

In some applications of the present invention, the apparatus further includes an elongated and flexible anchor delivery channel sized and configured to extend within the structure lumen while at least a portion of the annuloplasty structure is within the passage of the catheter.

In some applications of the present invention, the apparatus further includes a first control mechanism and a second control mechanism, the first and the second control mechanisms are configured to enable independent movement of the catheter and the anchor delivery channel, respectively.

In some applications of the present invention, the anchor delivery channel is configured to be advanced with the annuloplasty structure during a period when the catheter is maintained in a substantially constant position.

In some applications of the present invention, the first control mechanism and the second control mechanism are configured to enable incremental release of the annuloplasty structure from a distal end of the channel as the plurality of anchors are sequentially deployed from the anchor delivery channel.

In some applications of the present invention, the plurality of anchors are configured for location within the anchor delivery channel, a distal end of the anchor delivery channel is configured for location within the structure lumen, and the annuloplasty structure is configured for location within the delivery passage.

In some applications of the present invention, the cardiac valve is a mitral valve.

In some applications of the present invention, the apparatus further includes an elongated introducer shaft sized for delivery through the vasculature, the introducer shaft defining a lumen and having an elongated shaft axis extending therethrough, the lumen is sized and configured to hold at least a portion of the catheter therein while the catheter axis is substantially parallel to the shaft axis.

In some applications of the present invention, further including a catheter control mechanism and an introducer control mechanism configured to enable independent movement of the catheter and the introducer shaft.

In some applications of the present invention, the apparatus further includes a first locking mechanism located at a distal region of the catheter and a second locking mechanism located at a proximal region of the catheter, the first and the second locking mechanisms are configured to inhibit rotation of the catheter.

In some applications of the present invention, the first locking mechanism includes a detent.

In some applications of the present invention, the first and the second locking mechanisms are configured to lock substantially simultaneously.

There is additionally provided, in accordance with some applications of the present invention, a device for repairing a cardiac valve, the device including:
- a catheter sized and configured for delivery through vasculature of a subject, the catheter defining a delivery passage and having an elongated catheter axis extending therethrough; and
- an elongated and flexible annuloplasty structure contained within the catheter and having an elongated lumen therein and a structure axis extending along the lumen, the annuloplasty structure is sized and configured for delivery to a heart of the subject through the catheter substantially along the catheter axis while the structure axis is substantially parallel to the catheter axis, and the annuloplasty structure is constructed of a material configured to be pierced by anchors delivered from within the annuloplasty structure.

There is yet additionally provided, in accordance with some applications of the present invention, apparatus, including:
- a catheter;
- an implant, slidable through the catheter, and including a sleeve;
- a reference-force member, slidable through the catheter, and configured such that sliding of the reference-force member distally through the catheter pushes the implant distally through the catheter; and
- a stiffening element:
    - stiffer than the sleeve,
    - couplable to the sleeve so as to inhibit a flexibility of the sleeve, and
    - couplable to the reference-force member such that movement of the reference-force member away from the sleeve decouples the stiffening element from the sleeve.

In some applications of the present invention, the stiffening element is couplable to the sleeve and to the reference-force member such that progressive proximal movement of the reference-force member away from the sleeve reduces the inhibition of the flexibility of progressively proximal portions of the sleeve.

In some applications of the present invention, the stiffening element is couplable to the sleeve and to the reference-force member such that progressive proximal movement of the reference-force member away from the sleeve decouples the stiffening element from progressively proximal portions of the sleeve.

In some applications of the present invention, the stiffening element is couplable to the sleeve by being threaded a plurality of times through the sleeve, and the movement of the reference-force member away from the sleeve decouples the stiffening element from the sleeve by unthreading the stiffening element from the sleeve.

In some applications of the present invention, the stiffening element includes a stiffening wire.

In some applications of the present invention, the reference-force member includes a reference-force tube that defines a lumen therethrough.

In some applications of the present invention, the reference-force tube is reversibly couplable to the implant.

In some applications of the present invention, the sleeve defines a lumen, and, when the reference-force tube is coupled to the implant, the lumen of the reference-force tube is in fluid communication with the lumen of the sleeve.

There is also provided, in accordance with some applications of the present invention, apparatus for use with a subject, the apparatus including:
- a catheter, shaped to define a lumen therethrough, a distal end portion of the catheter being transluminally advanceable to a vicinity of an anatomical site, the catheter having a first steerable segment and a second steerable segment, the first steerable segment being steerable in a first plane, and the second steerable segment being steerable in a second plane which is at a non-zero angle with respect to the first plane; and
- a longitudinal implant, advanceable through at least part of the lumen and out of a distal end of the lumen, the catheter and the implant are assembled to configure the catheter and the implant to assume a multi-bend formation in which:
    - a first bend of the formation separates a first domain of the formation from a second domain of the formation,
    - a second bend of the formation separates the second domain of the formation from a third domain of the formation,
    - the first domain includes at least (1) a distal part of the first steering segment of the catheter and (2) a proximal part of the implant,
    - the second domain includes (1) a distal part of the second steering segment of the catheter and (2) a middle part of the implant, and none of the first steering segment, and
    - the third domain includes a distal part of the implant and none of the catheter.

In some applications of the present invention, the second steerable segment is steerable in a second plane which is perpendicular with respect to the first plane.

In some applications of the present invention, the catheter includes:
- a first pull ring and at least one first-segment steering wire configured to steer the first steerable segment, and
- a second pull ring and at least one second-segment steering wire configured to steer the second steerable segment.

In some applications of the present invention, the apparatus further includes an adjustment mechanism coupled to the implant at a distal portion of the implant at the third domain, the adjustment mechanism being configured to adjust a degree of tension of the implant.

In some applications of the present invention, the apparatus further includes a guide member that is reversibly coupled to the adjustment mechanism at a distal portion of the guide member, a generally-triangular shape is formed in the apparatus between: (1) the guide member, (2) the distal portion of the implant structure at at least a portion of the third domain, and (3) at least a portion of the second domain.

In some applications of the present invention, the apparatus further includes a channel having an opening at a distal end thereof, the channel being advanceable within a lumen of the implant, the second domain includes a distal end portion of the channel, and a generally-triangular shape is formed in the apparatus between: (1) the guide member, (2) the distal portion of the implant structure at at least a portion of the third domain, and (3) the distal end portion of the channel.

The present invention will be more fully understood from the following detailed description of embodiments thereof, taken together with the drawings, in which:

BRIEF DESCRIPTION OF THE DRAWINGS

FIGS. 1A and 1B are schematic illustrations of an adjustable partial annuloplasty ring in a non-contracted state, in accordance with respective applications of the present invention;

FIG. 2 is a schematic longitudinal cross-sectional illustration of an anchor deployment manipulator, in accordance with some applications of the present invention;

FIG. 3 is a schematic longitudinal cross-sectional illustration of the anchor deployment manipulator of FIG. 2 advanced into the annuloplasty ring of FIG. 1A, in accordance with some applications of the present invention;

FIG. 4 is a schematic cross-sectional illustration of the anchor deployment manipulator of FIG. 2 advanced into the annuloplasty ring of FIG. 1A or 1B, taken along section IV-IV of FIG. 3, in accordance with some applications of the present invention;

FIG. 8 is a schematic illustration of the system of FIGS. 1-4 comprising a flexible pusher element, in accordance with some applications of the present invention;

FIG. 9 is a schematic illustration of a pusher tube applied to a proximal end of the sleeve of FIGS. 1-4, in accordance with some applications of the present invention;

FIGS. 10 and 11 are schematic illustrations of the system of FIGS. 1-4 comprising a steerable tube, in accordance with some applications of the present invention;

FIGS. 15A-E are schematic illustrations of cross-sectional images of components of the catheter system of FIGS. 13-14, in accordance with some applications of the present invention;

FIGS. 19A-B are schematic illustrations of components of the catheter system of FIGS. 13-14, in accordance with some other applications of the present invention;

FIGS. 20A-I are schematic illustrations of a procedure for implanting an annuloplasty ring structure to repair a mitral valve, in accordance with some applications of the present invention;

FIGS. 22A-D are schematic illustrations of an indicator and locking system comprising a protrusion and a housing, or cradle, shaped to define a groove, in accordance with some applications of the present invention;

FIGS. 23A-C are schematic illustrations of a tissue anchor, in accordance with some applications of the present invention;

FIG. 26 is a schematic illustration of a stiffening element, in accordance with some applications of the present invention;

DETAILED DESCRIPTION OF EMBODIMENTS

Figure 5A:
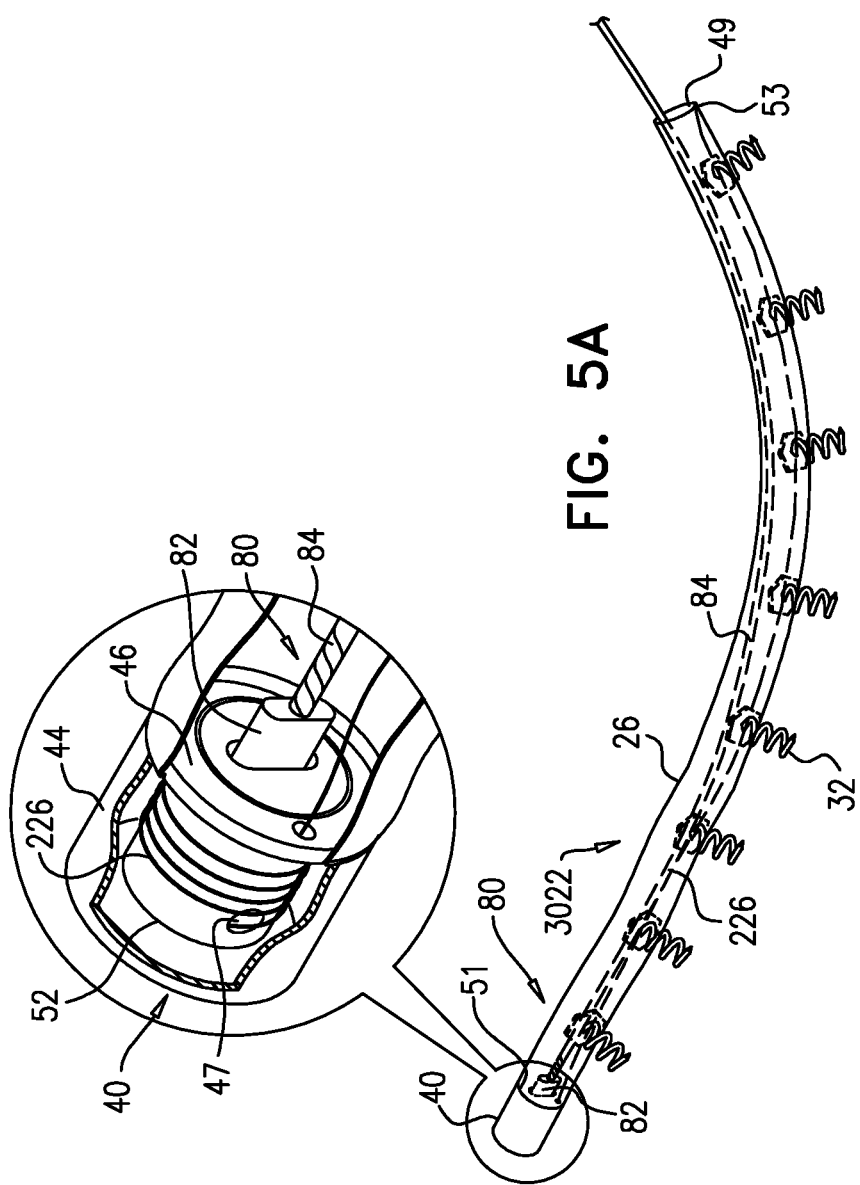
FIGS. 5A-B are schematic illustrations of a screwdriver tool being used to rotate a spool of an adjustment mechanism of the rings of FIGS. 1A and 1B, respectively, in accordance with respective applications of the present invention.

FIGS. 1A-4 are schematic illustrations of a system 10 for repairing a dilated atrioventricular valve, such as a mitral valve, in accordance with some applications of the present invention. System 10 comprises a longitudinal implant comprising an adjustable partial annuloplasty ring 3022, shown alone in FIGS. 1A and 1B in a non-contracted state, and an anchor deployment manipulator 61, shown alone in FIG. 2. Annuloplasty ring 3022 comprises a flexible sleeve 26. Anchor deployment manipulator 61 is advanced into sleeve 26, as shown in FIGS. 3 and 4, and, from within the sleeve, deploys anchors 32 through a wall of the sleeve into cardiac tissue, thereby anchoring the ring around a portion of the valve annulus.

FIGS. 1A and 1B are schematic illustration of annuloplasty ring 3022 in a non-contracted state, in accordance with some applications of the present invention. Sleeve 26 is typically configured to be placed only partially around the valve annulus (i.e., to assume a C-shape), and, once anchored in place, to be contracted so as to circumferentially tighten the valve annulus. Alternatively, the ring is configured to be placed entirely around the valve annulus. In order to tighten the annulus, annuloplasty ring 3022 comprises a flexible elongated contracting member 226 that extends along the ring.

Annuloplasty ring 3022 further comprises an adjustment mechanism 40, which facilitates contracting of the annuloplasty ring. Adjustment mechanism 40 is described in more detail hereinbelow. In addition, the ring comprises a plurality of anchors 32, typically between about 5 and about 20 anchors, such as about 10 or about 16 anchors. In FIGS. 1A and 1B, anchors 32 are shown prior to their insertion into ring 3022, while in FIG. 3 one of the anchors is shown deployed through the wall of sleeve 26, and a second one of the anchors is shown during deployment by anchor deployment manipulator 61. The insertion of the anchors into the sleeve and deployment of the anchors into cardiac tissue is described in detail hereinbelow.

Flexible sleeve 26 may comprise a braided, knitted, or woven mesh or a tubular structure comprising ePTFE. For some applications, the braid comprises metal and fabric fibers. The metal fibers, which may comprise Nitinol for example, may help define the shape of the sleeve, e.g., hold the sleeve open to provide space for passage and manipulation of deployment manipulator 61 within the sleeve. The fabric fibers may promote tissue growth into the braid. Optionally, the sleeve is somewhat elastic, which gives the sleeve a tendency to longitudinally contract, thereby helping tighten the sleeve. For example, the sleeve may be bellows- or accordion-shaped.

Typically, the sleeve is configured to have a tendency to assume a straight shape. This straightness helps the surgeon locate the next site for each subsequent anchor during the implantation procedure, as described hereinbelow with reference to FIGS. 6A-I. For example, because the sleeve assumes a generally straight shape, the sleeve may help provide an indication of distance between adjacent anchoring sites.

For some applications, the sleeve is configured to have a controllably variable stiffness. For example, a somewhat stiff wire may be placed in the sleeve to provide the stiffness, and subsequently be removed at the conclusion of the implantation procedure when the stiffness is no longer useful.

Elongated contracting member 226 comprises a wire, a ribbon, a rope, or a band, which typically comprises a flexible and/or superelastic material, e.g., nitinol, polyester, stainless steel, or cobalt chrome. In some applications, contracting member 226 comprises a braided polyester suture (e.g., Ticron). In some applications, contracting member 226 is coated with polytetrafluoroethylene (PTFE). In some applications, contracting member 226 comprises a plurality of wires that are intertwined to form a rope structure.

For some applications, contracting member 226 is positioned at least partially within a lumen of the sleeve 26, such as entirely within the lumen (as shown in FIGS. 1A-B, 5A-B, 6H, and 6I). For some applications in which the contracting member is positioned partially within the lumen, the contracting member is sewn into the wall of the sleeve, such that the contracting member is alternatingly inside and outside of the sleeve along the length of the sleeve (as shown in FIGS. 3, 8, and 9). Optionally, sleeve 26 defines an internal channel within which member 226 is positioned (configuration not shown). Alternatively, the contracting member is disposed outside the lumen of the sleeve, such as alongside an outer wall of the sleeve. For example, sleeve 26 may define an external channel within which member 226 is positioned, or the sleeve may comprise or be shaped so as to define external coupling elements, such as loops or rings (configuration not shown). For some applications, contracting member 226 is positioned approximately opposite the anchors.

In an embodiment of the present invention, adjustment mechanism 40 comprises a housing 44 which houses a spool 46, i.e., a rotatable structure, to which a first end 47 of contracting member 226 is coupled. Spool 46 is positioned in a vicinity of (e.g., within 1 cm of) either a distal end 51 of sleeve 26, as shown in FIGS. 1A and 3, or a proximal end 49 of sleeve 26, as shown in FIG. 1B. A second end 53 of contracting member 226 is coupled to the sleeve in a vicinity of (e.g., within 1 cm of) the end of the sleeve opposite the end to which the spool is positioned. In the configuration shown in FIGS. 1A and 3, second end 53 of contracting member 226 is coupled to the sleeve in a vicinity of proximal end 49 of the sleeve, while in the configuration shown in FIG. 1B, the second end of the contracting member is coupled to the sleeve in a vicinity of distal end 51 of the sleeve. Rotation of spool 46 winds a portion of the contracting member around the spool, thereby pulling the far end of the ring toward the spool and shortening and tightening the ring.

Alternatively, in some configurations, spool 46 is positioned at an intermediary position along the sleeve, rather than in a vicinity of one of the ends. For these configurations, contracting member 226 comprises two contracting members, which are respectively connected to the two ends of the sleeve, and both of which are connected to the spool. Rotating the spool contracts both contracting members. These configurations may be implemented using techniques described in U.S. patent application Ser. No. 12/341,960 to Cabiri, which published as US 2010/0161047, issued as U.S. Pat. No. 8,241,351, and which is incorporated herein by reference, with reference to FIG. 15 thereof.

Spool 46 is shaped to provide a hole 42 or other coupling mechanism for coupling first end 47 of contracting member 226 to the spool, and thereby to adjustment mechanism 40. Spool 46 is shaped to define a driving interface 48. For some applications, driving interface 48 is female. For example, the interface may be shaped to define a channel which extends through the cylindrical portion of spool 46 from an opening provided by an upper surface 3050 of spool 46 to an opening provided by a lower surface 3052 of spool 46. Alternatively, driving interface 48 is shaped so as to define an indentation (e.g., a groove) that does not extend entirely through the cylindrical portion of the spool. Further alternatively, driving interface 48 is male, and defines a protrusion, e.g., a hexagonal head or a head having another shape.

A distal portion of a screwdriver tool 80, which is described hereinbelow with reference to FIGS. 5A-B, engages spool 46 via driving interface 48 and rotates spool 46 in response to a rotational force applied to the screwdriver. The rotational force applied to the screwdriver tool rotates spool 46 via the portion of the screwdriver tool that engages driving interface 48 of spool 46.

Spool 46 typically comprises a locking mechanism that prevents rotation of the spool after contracting member 226 has been tightened. For example, locking techniques may be used that are described with reference to FIG. 4 of above-mentioned U.S. application Ser. No. 12/341,960 to Cabiri, which published as US 2010/0161047 and which is incorporated herein by reference.

Alternatively, in an embodiment of the present invention, adjustment mechanism 40 is configured to tighten contracting member 226, crimp the contracting member to hold the contracting member taut, and subsequently cut the excess length of the contracting member.

FIG. 2 is a schematic longitudinal cross-sectional illustration of anchor deployment manipulator 61, FIG. 3 is a schematic longitudinal cross-sectional illustration of the anchor deployment manipulator advanced into annuloplasty ring 3022, and FIG. 4 is a schematic cross-sectional illustration of the anchor deployment manipulator advanced into the annuloplasty ring, taken along section Iv-Iv of FIG. 3, in accordance with some applications of the present invention. Anchor deployment manipulator 61 is advanced into a lumen of sleeve 26, and, from within the lumen, deploys anchors 32 through a wall of the sleeve and into cardiac tissue, thereby anchoring the sleeve around a portion of the valve annulus. Typically, annuloplasty ring 3022 and anchor deployment manipulator 61 are introduced into the heart via a sheath 2104, as described hereinbelow with reference to FIGS. 6A-I.

In an embodiment of the present invention, at least one of anchors 32 is deployed from a distal end 3060 of manipulator 61 while the distal end is positioned such that a central longitudinal axis 3062 through distal end 3060 of manipulator 61 forms an angle α (alpha) of between about 20 and 90 degrees, e.g., between about 45 and 90 degrees, with the wall of sleeve 26 at the point at which the anchor penetrates the wall, such as between about 75 and 90 degrees, e.g., about 90 degrees. (In FIG. 3, a line 64 schematically illustrates the plane tangential to the wall of the sleeve at the anchor-penetration point.) This anchor-penetration point is typically at a portion of the sleeve that extends distally beyond the distal end of outer tube 3066 of deployment manipulator 61 (which is described hereinbelow), i.e., that is no longer in contact with the outer surface of outer tube 3066. Typically, all of the anchors are deployed at such angles, with the possible exception of the first anchor deployed near the distal end of the sleeve.

For some applications, at least one of anchors 32 is deployed from distal end 3060 of manipulator 61 while distal end 3060 is positioned such that longitudinal axis 3062 through distal end 3060 of manipulator 61 forms an angle β (beta) of between about 20 and 90 degrees (such as between about 45 and 90 degrees, e.g., such as between about 75 and 90 degrees, e.g., about 90 degrees) with a line 3065 defined by (a) a first point 3067 at which the anchor currently being deployed penetrates the wall of the sleeve and (b) a second point 3069 at which a most recently previously deployed anchor penetrates the wall of sleeve 26. Typically, all of the anchors are deployed at such angles, with the exception of the first anchor deployed near the distal end of the sleeve.

Typically, the anchors are deployed from distal end 3060 of manipulator 61 into the cardiac tissue in a direction parallel to central longitudinal axis 3062.

In an embodiment of the present invention, anchor deployment manipulator 61 comprises an outer tube 3066 and an anchor driver 36 which is at least partially positioned within tube 3066. Anchor driver 36 comprises an elongated, flexible shaft 3070, having at its distal end a driver head 3072. Rotation of the anchor driver screws the anchors into the cardiac tissue. Each of anchors 32 is shaped so as to define a coupling head 74 and a tissue coupling element 76. The anchors are typically rigid. Tissue coupling elements 76 may, for example, be helical or spiral in shape (e.g., having the shape of a corkscrew), as shown in the figures, may comprises screws, or may have other shapes. Coupling heads 74 may be either male (e.g., a hex or square protrusion) or female (e.g., a straight slot, a hex opening, a Phillips opening, or a Robertson opening). The use of helical anchors, which are screwed into the cardiac tissue, generally minimizes the force that needs to be applied during deployment of the anchors into the cardiac tissue. Alternatively, the anchors may comprise staples, clips, spring-loaded anchors, or other tissue anchors described in the references incorporated hereinabove in the Background section, or otherwise known in the art. For some applications, outer tube 3066 of deployment manipulator 61 is steerable, as known in the catheter art, while for other applications, a separate steerable tube is provided, as described hereinbelow with reference to FIG. 10 or FIG. 11. To provide steering functionality to deployment manipulator, outer tube 3066, steerable tube 360 (FIG. 10), or steerable tube 362 (FIG. 11), as the case may be, typically comprises one or more steering wires, the pulling and releasing of which cause deflection of the distal tip of the tube.

In an embodiment of the present invention, each of tissue coupling elements 76 is shaped so as to define a longitudinal axis 78 (shown in FIGS. 1A-B), and is configured to penetrate the cardiac tissue in a direction parallel to longitudinal axis 78. Deployment manipulator 61 is configured to deploy tissue coupling element 76 from distal end 3060 of the manipulator through the wall of sleeve 26 in a direction parallel to longitudinal axis 78 and parallel to central longitudinal axis 3062 through distal end 3060 of deployment manipulator 61 (shown in FIGS. 2, 3, and 7-10).

For some applications, the plurality of anchors are applied using the manipulator by loading a first one of the anchors onto the anchor driver, and deploying the anchor into the cardiac tissue. The anchor driver is withdrawn from the subject's body (typically while leaving outer tube 3066 of the deployment manipulator in place in the sleeve), and a second one of the anchors is loaded onto the anchor driver. The anchor driver is reintroduced into the outer tube of the manipulator, and the second anchor is deployed. These steps are repeated until all of the anchors have been deployed. Alternatively, the entire deployment manipulator, including the anchor driver, is removed from the body and subsequently reintroduced after being provided with another anchor. Further alternatively, the deployment manipulator is configured to simultaneously hold a plurality of anchors, and to deploy them one at a time (configuration not shown).

Typically, the first anchor 32 is deployed most distally in sleeve 26 (generally at or within a few millimeters of a distal end 51 of the sleeve), and each subsequent anchor is deployed more proximally, such that manipulator 61 is gradually withdrawn in a proximal direction during the anchoring procedure.

Figure 5B:
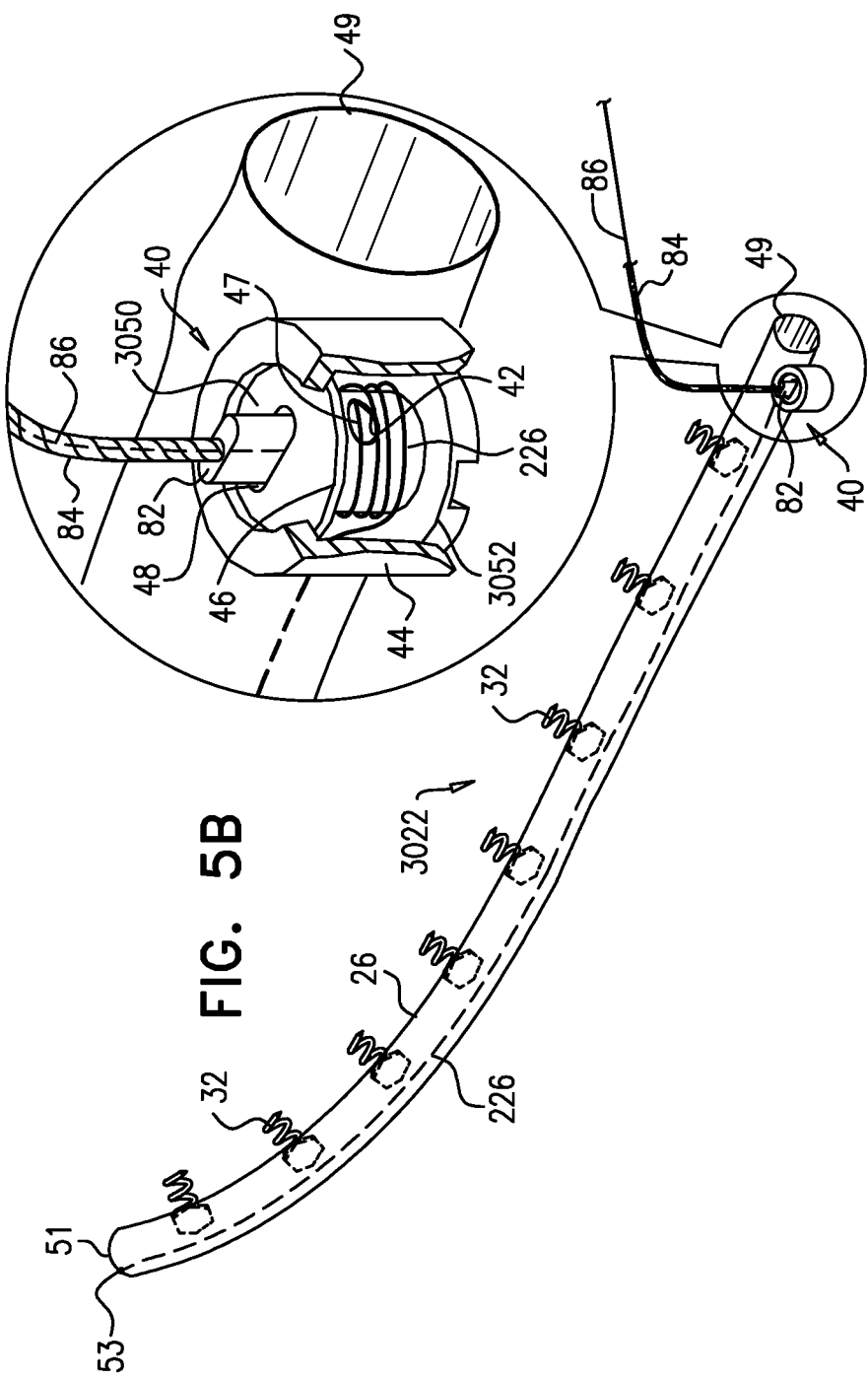

Reference is now made to FIGS. 5A-B, which are schematic illustrations of screwdriver tool 80 being used to rotate spool 46 of adjustment mechanism 40 of ring 3022, in accordance with some applications of the present invention. Screwdriver tool 80 has a head 82 that is either male (e.g., comprising a screwdriver head, having, such as a slot-head, an Allen-head, a Phillips-head, a Robertson-head, or a hex-head) or female (e.g., comprising a wrench head, having, for example, a square or hex opening), as appropriate for the driving interface provided. Typically, the screwdriver tool comprises a shaft 84, at least a portion of which is flexible. For some applications, the screwdriver tool is used that is described in above-referenced U.S. patent application Ser. No. 12/341,960 (which published as US 2010/0161047, issued as U.S. Pat. No. 8,241,351, and which is incorporated herein by reference), with reference to FIG. 4 thereof. Alternatively, anchor driver 36 of deployment manipulator 61 serves as screwdriver tool 80, and is used to rotate the spool, in which case driving interface 48 is appropriately shaped to receive driver head 3072 of anchor driver 36.

In the configuration shown in FIG. 5A, contracting member 226 is coupled to distal end 51 of sleeve 26, as shown hereinabove in FIGS. 1A and 3. Adjustment mechanism 40 is oriented such that driving interface 48 thereof is accessible from within sleeve 26. Screwdriver tool 80 is inserted into sleeve 26, and used to rotate spool 46 via the driving interface. Alternatively, anchor driver 36 of deployment manipulator 61 serves as screwdriver tool 80, and is used to rotate the spool, in which case driving interface 48 is appropriately shaped to engage driver head 3072 of anchor driver 36. In either case, the sleeve thus serves to guide the screwdriver tool to driving interface 48. For some applications, an interior surface of the sleeve is tapered near the distal end of the sleeve, to help guide the screwdriver head to the driving interface. For some applications, during the implantation procedure, anchor deployment manipulator 61 is left slightly inserted into proximal end 49 of sleeve 26 after all of anchors 32 have been deployed, in order to facilitate passage of screwdriver tool 80 into sleeve 26.

In the configuration shown in FIG. 5B, access to driving interface 48 is provided from outside sleeve 26. For some applications, adjustment mechanism 40 comprises a wire 86 that is attached to the mechanism and passes out of the body of the subject, typically via sheath 2104. In order to readily bring the screwdriver tool to driving interface 48, screwdriver tool 80 is guided over (as shown) the wire, or alongside the wire (configuration not shown).

For some applications, adjustment mechanism 40 is positioned in a vicinity of (e.g., within 1 cm of) distal end 51 of sleeve 26, and access to driving interface 48 is provided from outside sleeve 26, as described with reference to FIG. 5B (in which the adjustment mechanism is positioned in a vicinity of proximal end 49 of the sleeve).

For some applications in which access to driving interface 48 is provided from outside sleeve 26, the screwdriver tool is initially removably attached to the driving interface, prior to the commencement of the implantation procedure, and is subsequently decoupled from the driving interface after spool 46 has been rotated. In these applications, adjustment mechanism 40 may be positioned in a vicinity of distal end 51 or proximal end 49 of sleeve 26, or at an intermediate location along the sleeve. Optionally, at least a portion of a shaft of the screwdriver tool is positioned within sheath 2104, which is described hereinbelow with reference to FIGS. 6A-I.

Reference is now made to FIGS. 6A-I, which are schematic illustrations of a procedure for implanting annuloplasty ring 3022 to repair a mitral valve 230, in accordance with some applications of the present invention. The procedure is typically performed with the aid of imaging, such as fluoroscopy, transesophageal echo, and/or echocardiography.

Figure 6A:
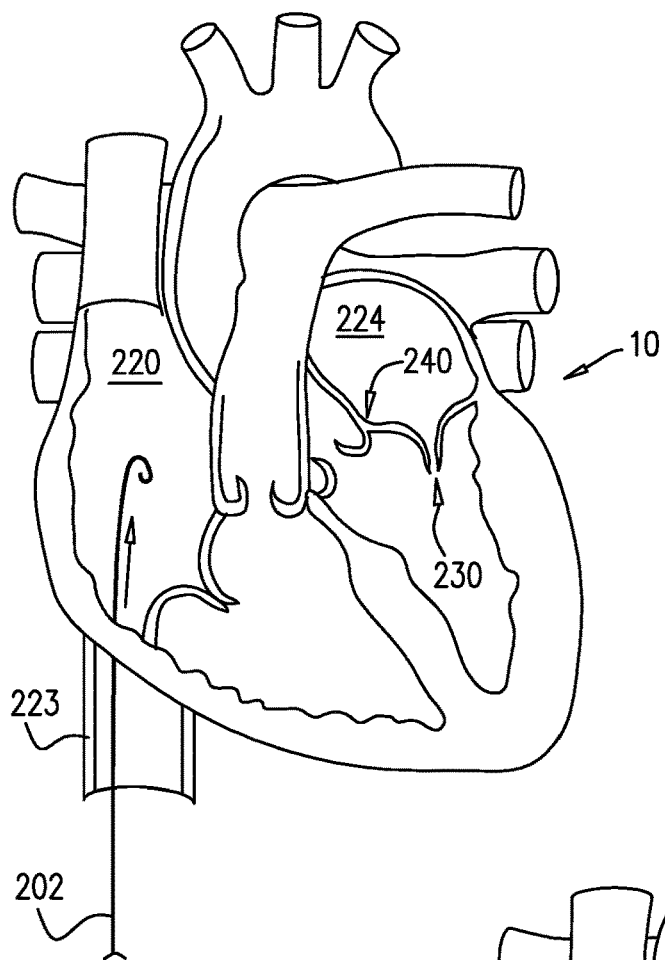
FIGS. 6A-I are schematic illustrations of a procedure for implanting the annuloplasty ring of FIG. 1A to repair a mitral valve, in accordance with some applications of the present invention.

The procedure typically begins by advancing a semi-rigid guidewire 202 into a right atrium 220 of the patient, as shown in FIG. 6A.

Figure 6B:
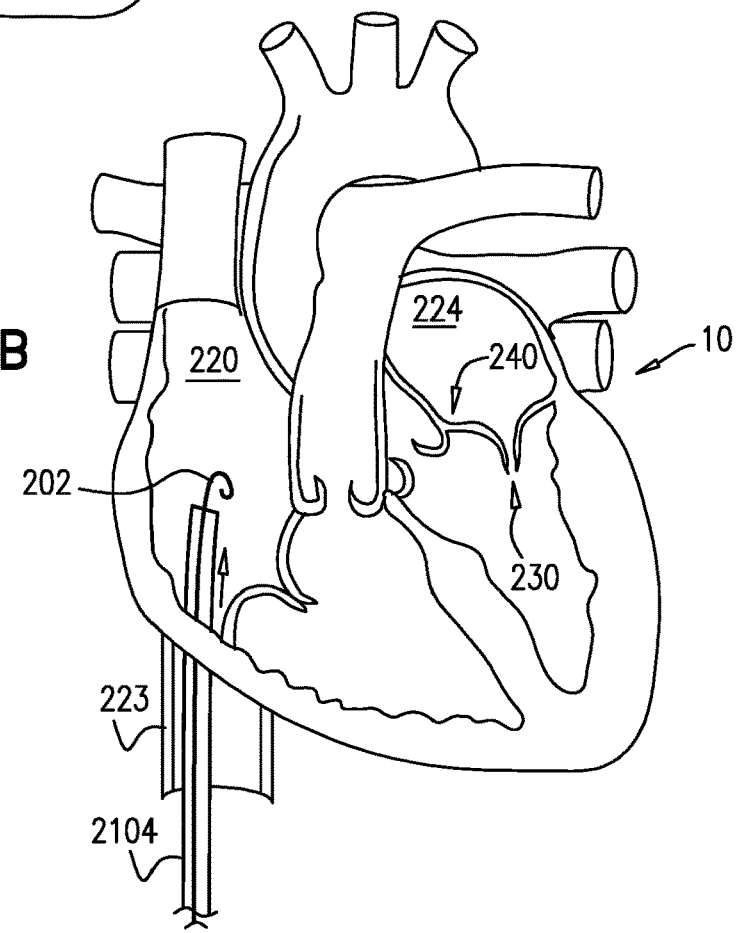
Figure 6C:
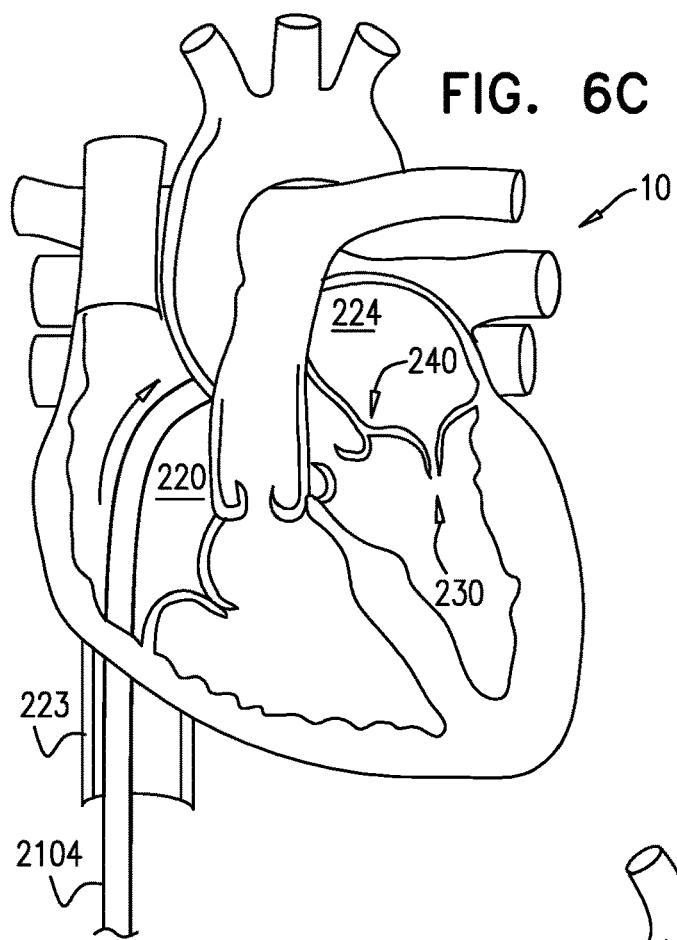

As show in FIG. 6B, guidewire 202 provides a guide for the subsequent advancement of a sheath 2104 therealong and into the right atrium. Once sheath 2104 has entered the right atrium, guidewire 202 is retracted from the patient's body. Sheath 2104 typically comprises a 14-20 F sheath, although the size may be selected as appropriate for a given patient. Sheath 2104 is advanced through vasculature into the right atrium using a suitable point of origin typically determined for a given patient. For example:

sheath 2104 may be introduced into the femoral vein of the patient, through an inferior vena cava 223, into right atrium 220, and into a left atrium 224 trans septally, typically through the fossa ovalis;

sheath 2104 may be introduced into the basilic vein, through the subclavian vein to the superior vena cava, into right atrium 220, and into left atrium 224 trans septally, typically through the fossa ovalis; or sheath 2104 may be introduced into the external jugular vein, through the subclavian vein to the superior vena cava, into right atrium 220, and into left atrium 224 transseptally, typically through the fossa ovalis.

In an embodiment of the present invention, sheath 2104 is advanced through an inferior vena cava 223 of the patient (as shown) and into right atrium 220 using a suitable point of origin typically determined for a given patient.

Sheath 2104 is advanced distally until the sheath reaches the interatrial septum.

Figure 6D:
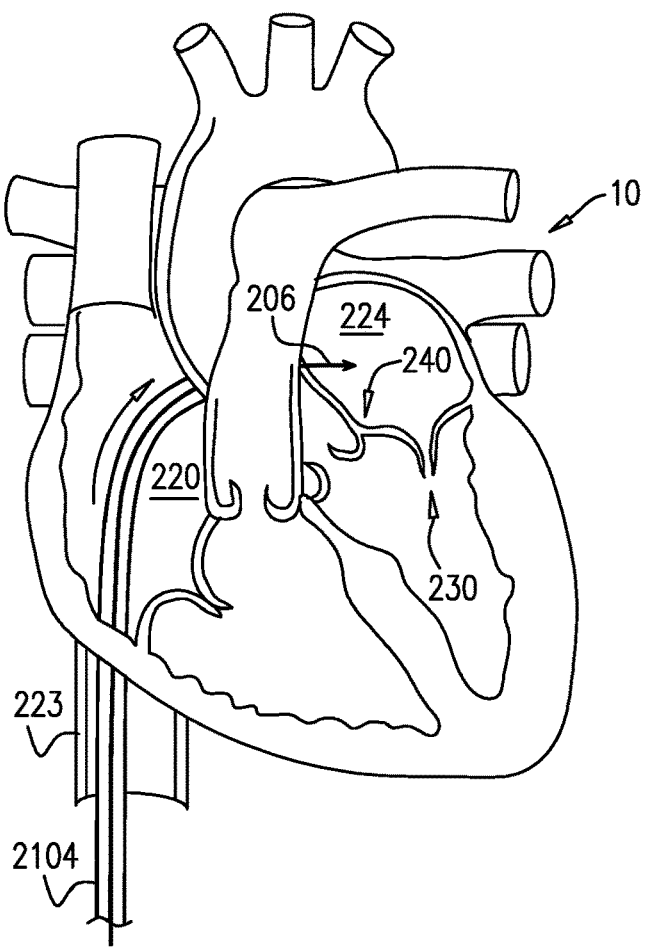

As shown in FIG. 6D, a resilient needle 206 and a dilator (not shown) are advanced through sheath 2104 and into the heart. In order to advance sheath 2104 transseptally into left atrium 224, the dilator is advanced to the septum, and needle 206 is pushed from within the dilator and is allowed to puncture the septum to create an opening that facilitates passage of the dilator and subsequently sheath 2104 therethrough and into left atrium 224. The dilator is passed through the hole in the septum created by the needle. Typically, the dilator is shaped to define a hollow shaft for passage along needle 206, and the hollow shaft is shaped to define a tapered distal end. This tapered distal end is first advanced through the hole created by needle 206. The hole is enlarged when the gradually increasing diameter of the distal end of the dilator is pushed through the hole in the septum.

Figure 6E:
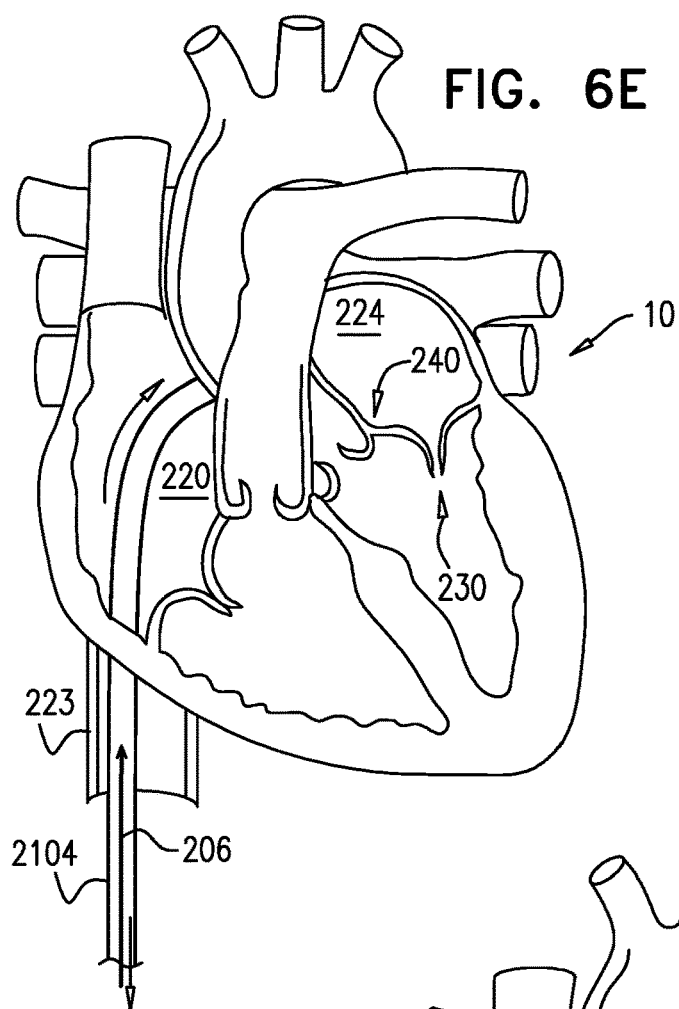

The advancement of sheath 2104 through the septum and into the left atrium is followed by the extraction of the dilator and needle 206 from within sheath 2104, as shown in FIG. 6E.

Figure 6F:
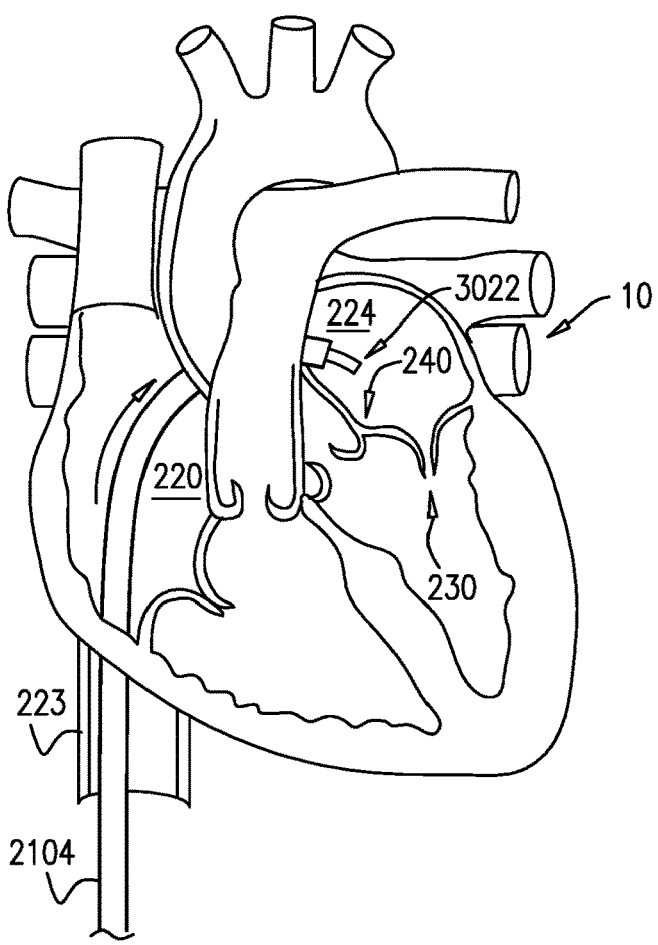

As shown in FIG. 6F, annuloplasty ring 3022 (with anchor deployment manipulator 61 therein) is advanced through sheath 2104 into left atrium 224.

Figure 6G:
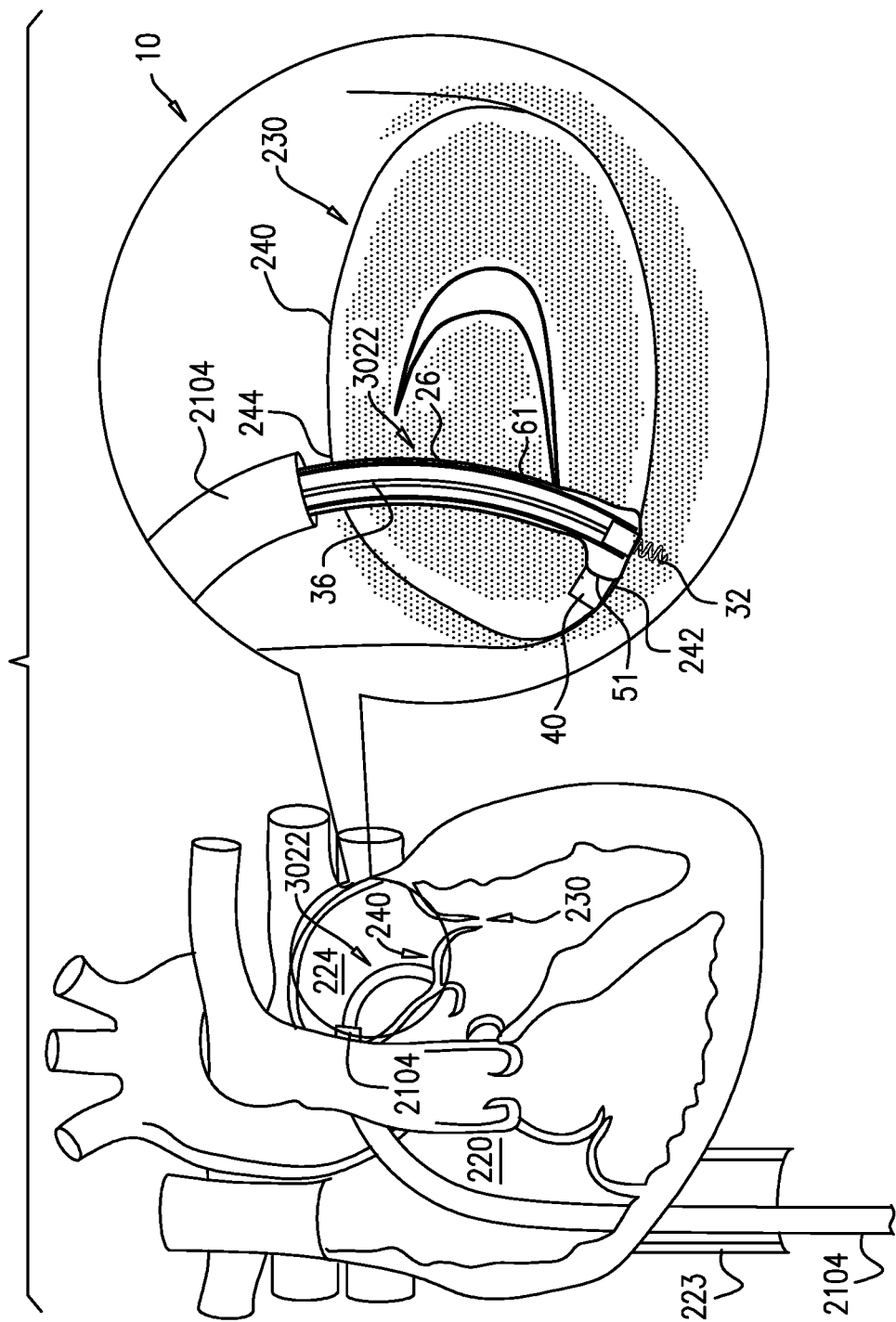

As shown in FIG. 6G, distal end 51 of sleeve 26 is positioned in a vicinity of a left fibrous trigone 242 of an annulus 240 of mitral valve 230. (It is noted that for clarity of illustration, distal end 51 of sleeve 26 is shown schematically in the cross-sectional view of the heart, although left trigone 242 is in reality not located in the shown cross-sectional plane, but rather out of the page closer to the viewer.) Alternatively, the tip is positioned in a vicinity of a right fibrous trigone 244 of the mitral valve (configuration not shown). Further alternatively, the distal tip of the sleeve is not positioned in the vicinity of either of the trigones, but is instead positioned elsewhere in a vicinity of the mitral valve, such as in a vicinity of the anterior or posterior commissure. For some applications, outer tube 3066 of anchor deployment manipulator 61 is steerable, as is known in the catheter art, while for other applications, a separate steerable tube is provided, as described hereinbelow with reference to FIG. 10 and FIG. 11. In either case, the steering functionality typically allows the area near the distal end of the manipulator to be positioned with six degrees of freedom. Once positioned at the desired site near the selected trigone, manipulator 61 deploys a first anchor 32 through the wall of sleeve 26 into cardiac tissue near the trigone.

Figure 6H:
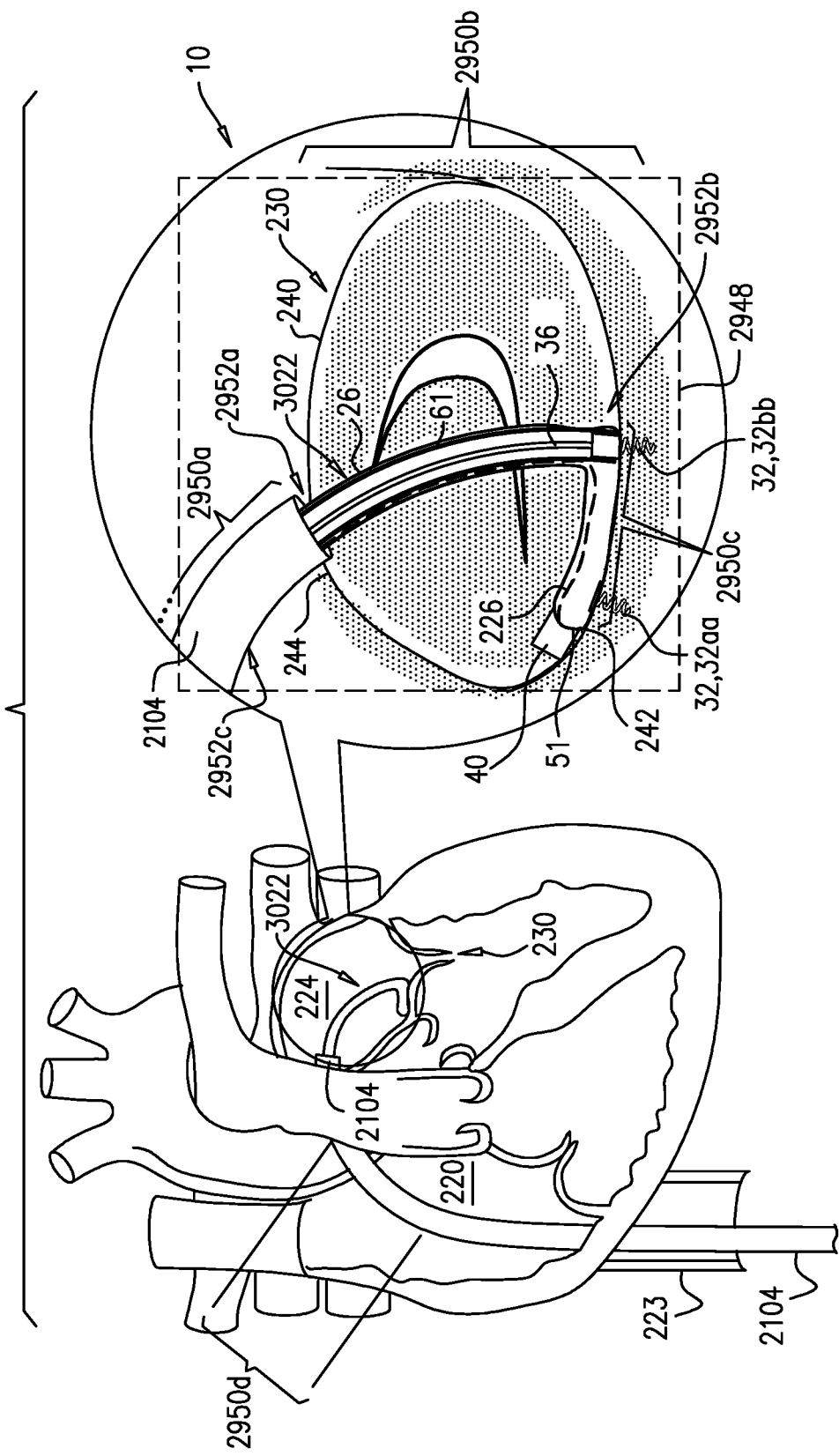

As shown in FIG. 6H, deployment manipulator 61 is repositioned along annulus 240 to another site selected for deployment of a second anchor 32. Typically, the first anchor is deployed most distally in the sleeve (generally at or within a few millimeters of the distal tip of the sleeve), and each subsequent anchor is deployed more proximally, such that the manipulator is gradually withdrawn in a proximal direction during the anchoring procedure. The already-deployed first anchor 32 holds the anchored end of sleeve 26 in place, so that the sleeve is drawn from the site of the first anchor towards the site of the second anchor. Deployment manipulator 61 deploys the second anchor through the wall of the sleeve into cardiac tissue at the second site. Depending on the tension applied between the first and second anchor sites, the portion of sleeve 26 therebetween may remain tubular in shape, or may become flattened, which may help reduce any interference of the ring with blood flow.

For some applications, in order to provide the second and subsequent anchors, anchor driver 36 is withdrawn from the subject's body via sheath 2104 (typically while leaving outer tube 3066 of the deployment manipulator in place in the sleeve), provided with an additional anchor, and then reintroduced into the subject's body and into the outer tube. Alternatively, the entire deployment manipulator, including the anchor driver, is removed from the body and subsequently reintroduced upon being provided with another anchor. Further alternatively, deployment manipulator 61 is configured to simultaneously hold a plurality of anchors, and to deploy them one at a time at the selected sites.

Figure 6I:
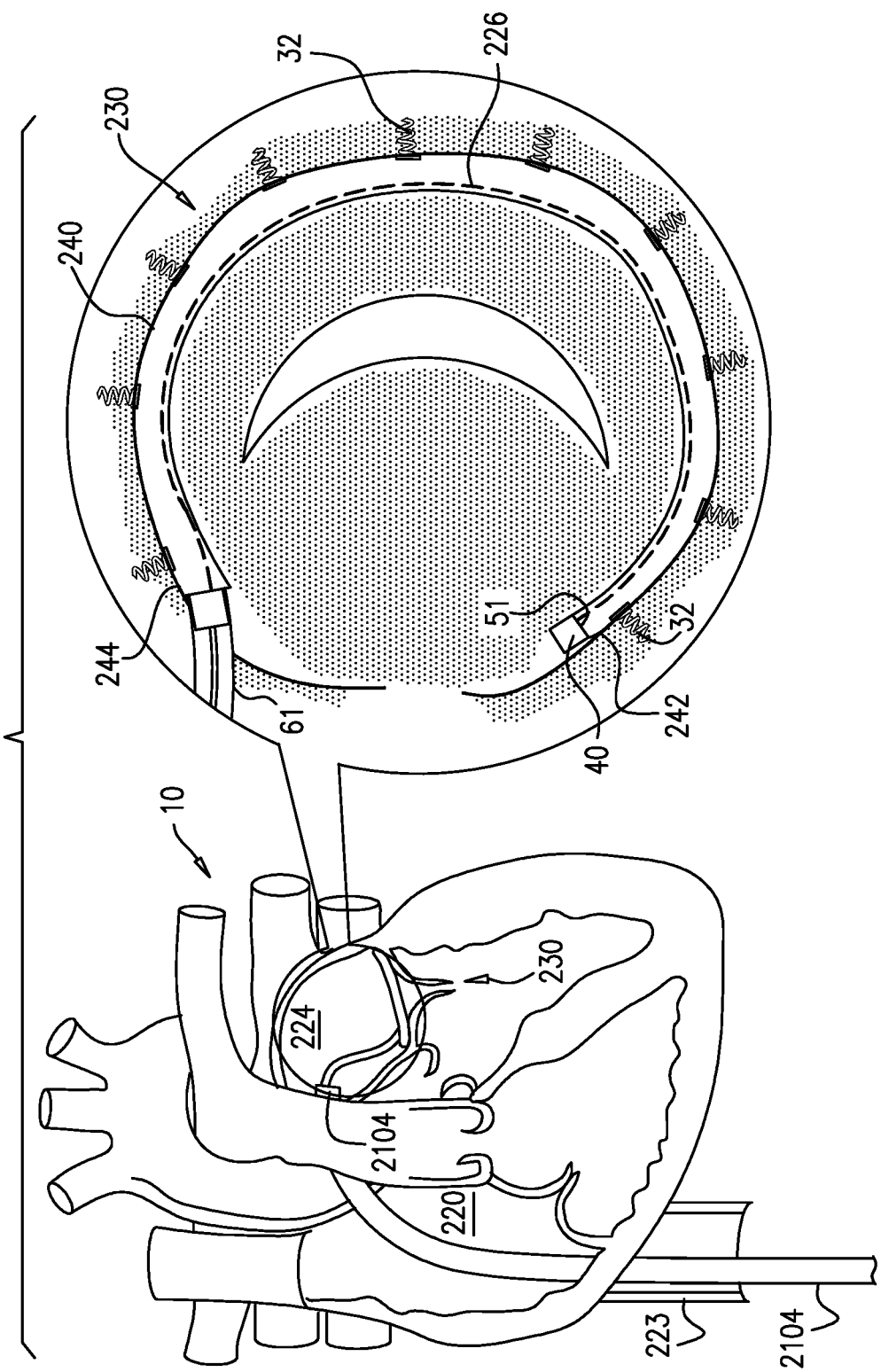

As shown in FIG. 6I, the deployment manipulator is repositioned along the annulus to additional sites, at which respective anchors are deployed, until the last anchor is deployed in a vicinity of right fibrous trigone 244 (or left fibrous trigone 242 if the anchoring began at the right trigone). Alternatively, the last anchor is not deployed in the vicinity of a trigone, but is instead deployed elsewhere in a vicinity of the mitral valve, such as in a vicinity of the anterior or posterior commissure.

As described hereinabove with reference to FIGS. 1A and 1B, a screwdriver tool or anchor driver 36 of deployment manipulator 61 is used to rotate spool 46 of adjustment mechanism 40, in order to tighten ring 3022. (For clarity of illustration, contracting member 226 of ring 3022, although provided, is not shown in FIGS. 6A-I.) Alternatively, another technique is used to tighten the ring, such as described hereinabove.

For some applications, sleeve 26 is filled with a material (e.g., polyester, polytetrafluoroethylene (PTFE), polyethylene terephthalate (PET), or expanded polytetrafluoroethylene (ePTFE)) after being implanted. The material is packed within at least a portion, e.g., 50%, 75%, or 100%, of the lumen of sleeve 26. The filler material functions to prevent (1) formation within the lumen of sleeve 26 of clots or (2) introduction of foreign material into the lumen which could obstruct the sliding movement of contracting member 226.

For some applications, proximal end 49 of sleeve 26 is closed upon completion of the implantation procedure. Alternatively, the proximal end of the sleeve may have a natural tendency to close when not held open by manipulator 61.

Figure 7:
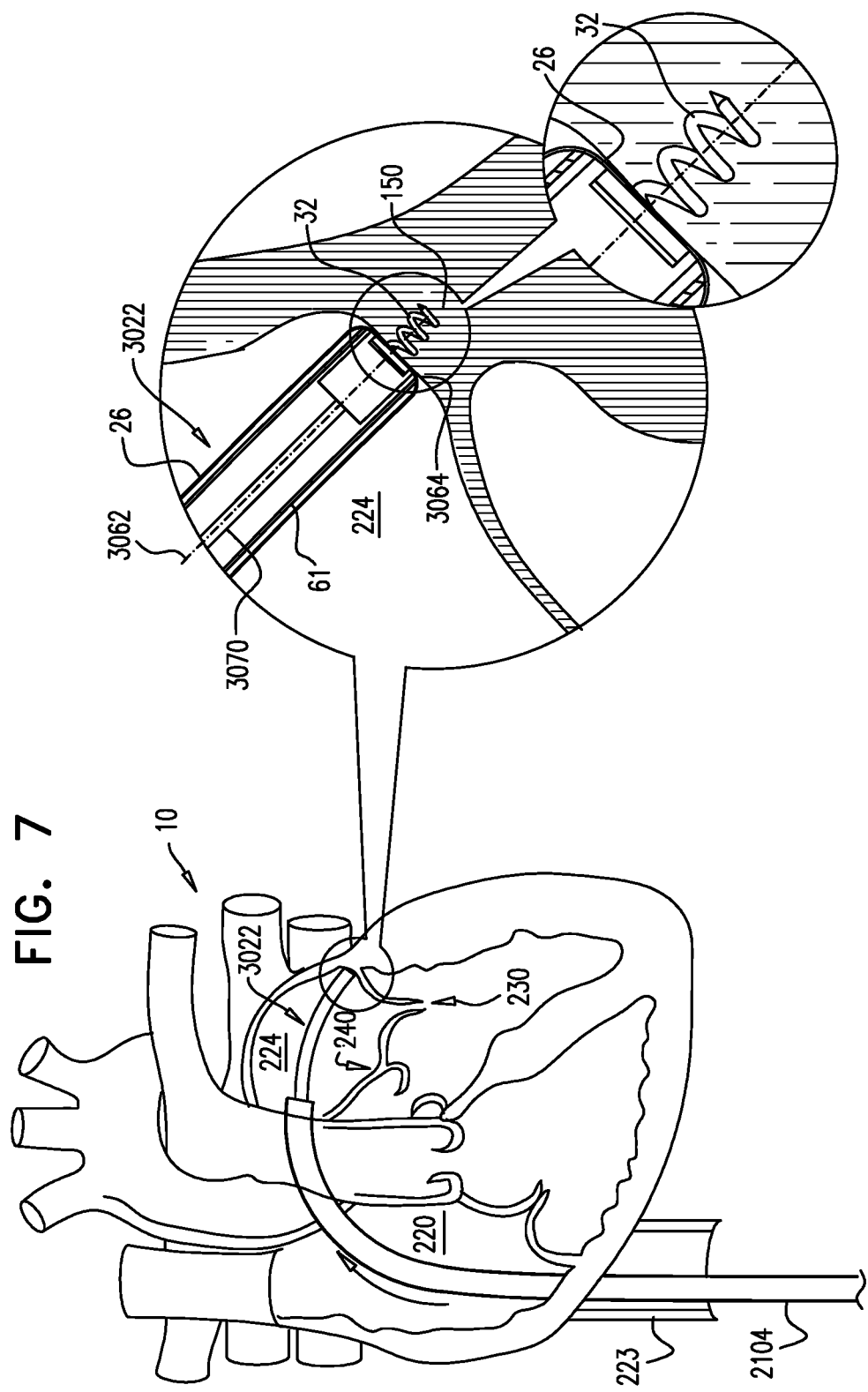
FIG. 7 is a schematic illustration of the deployment of an anchor into cardiac tissue, in accordance with some applications of the present invention.

Reference is made to FIG. 7, which is a schematic illustration of the deployment of one of anchors 32 into cardiac tissue, in accordance with some applications of the present invention. In this embodiment, one or more (such as all) of anchors 32 are deployed from left atrium 224, through tissue of the atrial wall, and into tissue of an upper region of the ventricular wall 150 near the atrium. Because the tissue of the upper region of ventricular wall is thicker than that of the atrial wall, deploying the anchors into the upper region of the ventricular wall generally provides more secure anchoring. In addition, because the anchors are not deployed laterally through the atrial wall, the risk of perforating the atrial wall is reduced.

Annuloplasty ring 3022 may be advanced toward annulus 240 in any suitable procedure, e.g., a transcatheter procedure, a minimally invasive procedure, or an open heart procedure (in which case one or more elements of system 10 are typically rigid). Regardless of the approach, the procedure typically includes the techniques described hereinabove with reference to FIGS. 6G-I and 7.

For some applications, following initial contraction of annuloplasty ring 3022 during the implantation procedure, the ring may be further contracted or relaxed at a later time after the initial implantation. Using real-time monitoring, tactile feedback and optionally in combination with fluoroscopic imaging, a screwdriver tool or anchor driver 36 of deployment manipulator 61 is reintroduced into the heart and used to contract or relax annuloplasty ring 3022.

Reference is now made to FIG. 8, which is a schematic illustration of system 10 comprising a flexible pusher element 200, in accordance with some applications of the present invention. Pusher element 200 aids with accurately positioning successive anchors 32 during an implantation procedure, such as described hereinabove with reference to FIGS. 6H and 6I. For some applications, pusher element 200 is positioned partially within tube 3066 of deployment manipulator 61 such that a distal portion 204 of pusher element 200 extends distally out of tube 3066, through an opening 208 in a vicinity of a distal end of the tube (e.g., that is within 3 mm of the distal end, such as within 2 mm of the distal end). A proximal portion of pusher element 200 passes through outer tube 3066 from opening 208 to the proximal end of tube 3066. Opening 208 is provided either through a wall of the tube (as shown in FIG. 8), or through the distal end of the tube (configuration not shown). Alternatively, pusher element 200 is positioned within sleeve 26, but outside of tube 3066 (configuration not shown). Typically, the pusher element is elongated, and is at least as long as sleeve 26.

Pusher element 200 helps move the distal end of deployment manipulator 61 from a first site of the annulus at which the manipulator has already deployed a first anchor (e.g., anchor 32A in FIG. 8) to a second site for deployment of a second anchor (e.g., anchor 32B), in a direction indicated schematically by an arrow 211. Pusher element 200 is pushed distally out of opening 208 of tube 3066, so that a distal end 212 of pusher element 200 engages and pushes against an interior surface of sleeve 26, in a direction indicated schematically by an arrow 214. The interior surface of the sleeve may be distal end 51 of the sleeve (as shown), or the wall of the sleeve at a location between distal end 51 and opening 208 (not shown). As a result, the distal end of manipulator 61 moves in the opposite direction, i.e., as indicated by arrow 211, toward a subsequent anchoring site. The movement in the direction of arrow 211 is generally along a line or curve defined by the portion of pusher element 200 already extended between the anchors that have already been deployed.

For some applications, as manipulator 61 is positioned at successive deployment sites of the cardiac tissue, pusher element 200 is extended respective distances through opening 208, each of which distances is successively greater. For other applications, after manipulator 61 is positioned at each successive deployment site, the pusher element is pulled back in a proximal direction, and again extended a desired distance in a distal direction, such that the pusher element pushes again the wall of the sleeve (at a different location on the wall for each successive relocation of manipulator 61).

This technique thus aids in locating each subsequent anchoring site for manipulator 61. The pusher element may also help control the distance between adjacent anchoring sites, because they surgeon may push the pusher element a known distance after deploying each anchor.

Pusher element 200 typically comprises a strip, wire, ribbon, or band, and has a cross-section that is circular, elliptical, or rectangular. Pusher element 200 typically comprises a flexible and/or superelastic material, such as a metal such as nitinol, stainless steel, or cobalt chrome. Distal end 212 of pusher element 200 is dull, so that it does not penetrate sleeve 26. For example, the distal end may be folded back, as shown in FIG. 8.

FIG. 9 is a schematic illustration of a pusher tube 250 applied to proximal end 49 of sleeve 26, in accordance with some applications of the present invention. Pusher tube 250 pushes gently in a distal direction on proximal end 49 of sleeve 26. For example, if, during withdrawal of outer tube 3066 in a proximal direction, the outer tube snags on the wall of sleeve 26 (which, as mentioned above, may comprise braided or woven fabric), such pushing may help free the snag. For some applications, the techniques of this embodiment are practiced in combination with those of the embodiment described hereinbelow with reference to FIG. 12. (Although in the embodiment described with reference to FIG. 9, system 10 typically comprises contracting member 226, for clarity of illustration the contracting member is not shown in the figure.)

FIG. 10 is a schematic illustration of system 10 comprising a steerable tube 360, in accordance with some applications of the present invention. In this embodiment, outer tube 3066 of deployment manipulator 61 is not steerable. Instead, to provide steering functionality, deployment manipulator 61 comprises a separate steering tube 360, which is positioned around at least a portion of outer tube 3066. Outer tube 3066, because it does not provide this steering functionality, may have a smaller diameter than in the embodiment described hereinabove with reference to FIG. 3. Because outer tube 3066 has a smaller diameter, sleeve 26 may also have a smaller diameter than in the embodiment described hereinabove with reference to FIG. 3. For some applications, the techniques of this embodiment are practiced in combination with those of the embodiment described hereinabove with reference to FIG. 9. (Although in the embodiment described with reference to FIG. 10, system 10 typically comprises contracting member 226, for clarity of illustration the contracting member is not shown in the figure.)

FIG. 11 is a schematic illustration of system 10 comprising a steerable tube 362, in accordance with some applications of the present invention. In this embodiment, outer tube 3066 of deployment manipulator 61 is not steerable. Steering functionality is instead provided by separate steering tube 362, which is positioned around at least a portion of shaft 3070 of anchor driver 36, and within outer tube 3066. For some applications, the techniques of this embodiment are practiced in combination with those of the embodiment described hereinabove with reference to FIG. 9. (Although in the embodiment described with reference to FIG. 11, system 10 typically comprises contracting member 226, for clarity of illustration the contracting member is not shown in the figure.)

Figure 12:
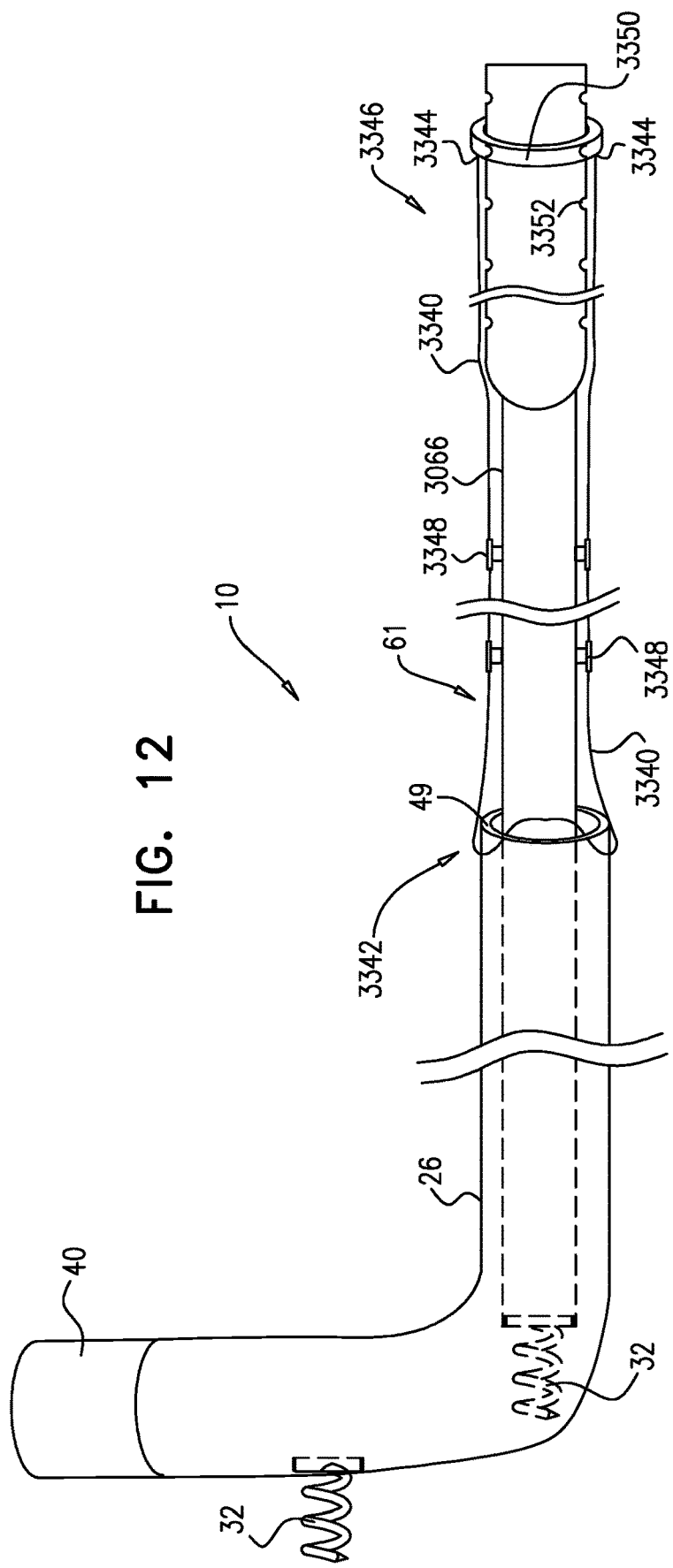
FIG. 12 is a schematic illustration of the system of FIGS. 1-4 comprising a pulling wire, in accordance with some applications of the present invention.

FIG. 12 is a schematic illustration of system 10 comprising a pulling wire 3340, in accordance with some applications of the present invention. A distal portion 3342 of pulling wire 3340 is coupled to proximal end 49 of sleeve 26, such as by passing through one or more holes near the proximal end. One or more proximal portions 3344 of the pulling wire are coupled to an external control handle 3346 of system 10, which is manipulated by the surgeon outside of the subject's body. Optionally, a portion of deployment manipulator 61 (e.g., a portion of outer tube 3066) which is never inserted in sleeve 26 comprises one or more coupling elements 3348, such as loops or tubes, through which pulling wire 3340 passes in order to hold the pulling wire close to the external surface of the deployment manipulator.

Pulling wire 3340 holds sleeve 26 surrounding deployment manipulator 61. As the pulling wire is released in a distal direction as deployment manipulator 61 is withdrawn in a proximal direction, the release of the sleeve allows the sleeve to gradually be removed from around the deployment manipulator. In FIG. 12, the sleeve is shown partially removed from the manipulator, including the portion of the sleeve through which one of anchors 32 has been deployed.

For some applications, control handle 3346 is configured to release pulling wire 3340 incrementally, such that each time the wire is further released by a set distance. As a result, the deployment manipulator is withdrawn from the sleeve by this set distance, and subsequently-deployed anchors are approximately this set distance apart from one another. For example, the handle may comprise a control ring 3350 that is coupled to proximal portions 3344 of the wire, and removably engages slots 3352 on the handle that are spaced apart by this set distance. Upon completion of the implantation procedure, in order to detach the pulling wire from the sleeve, one end of the wire may be cut or released, and the wire detached from the sleeve by pulling on the other end of the wire.

(Although in the embodiment described with reference to FIG. 12, system 10 typically comprises contracting member 226, for clarity of illustration the contracting member is not shown in the figure.)

Figure 13:
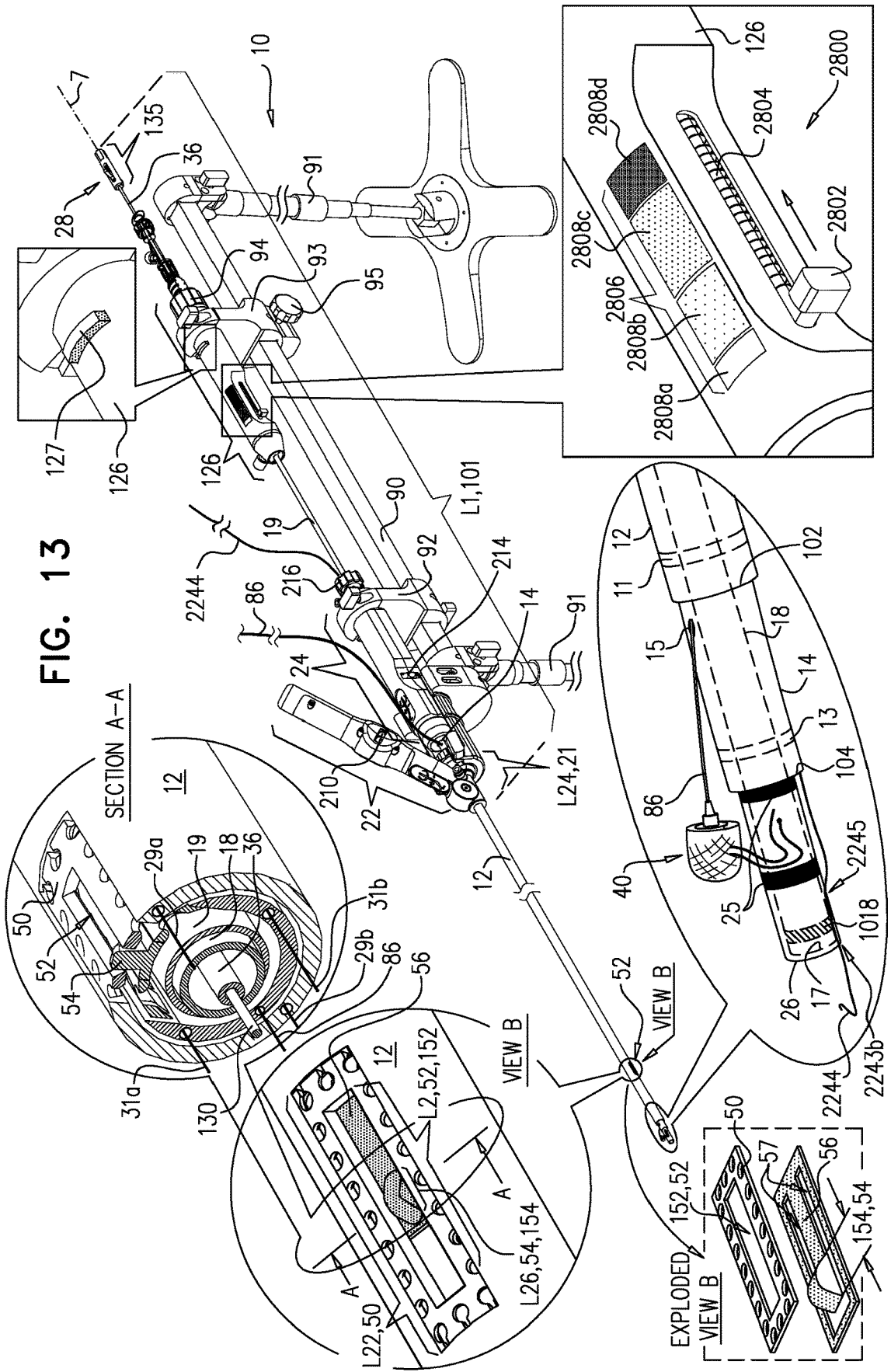
FIGS. 13-14 are schematic illustrations of multi-component tubular system for delivering and anchoring an implant and for controlling a relative spatial orientation of components of the catheter system, in accordance with some applications of the present invention.
Figure 14:
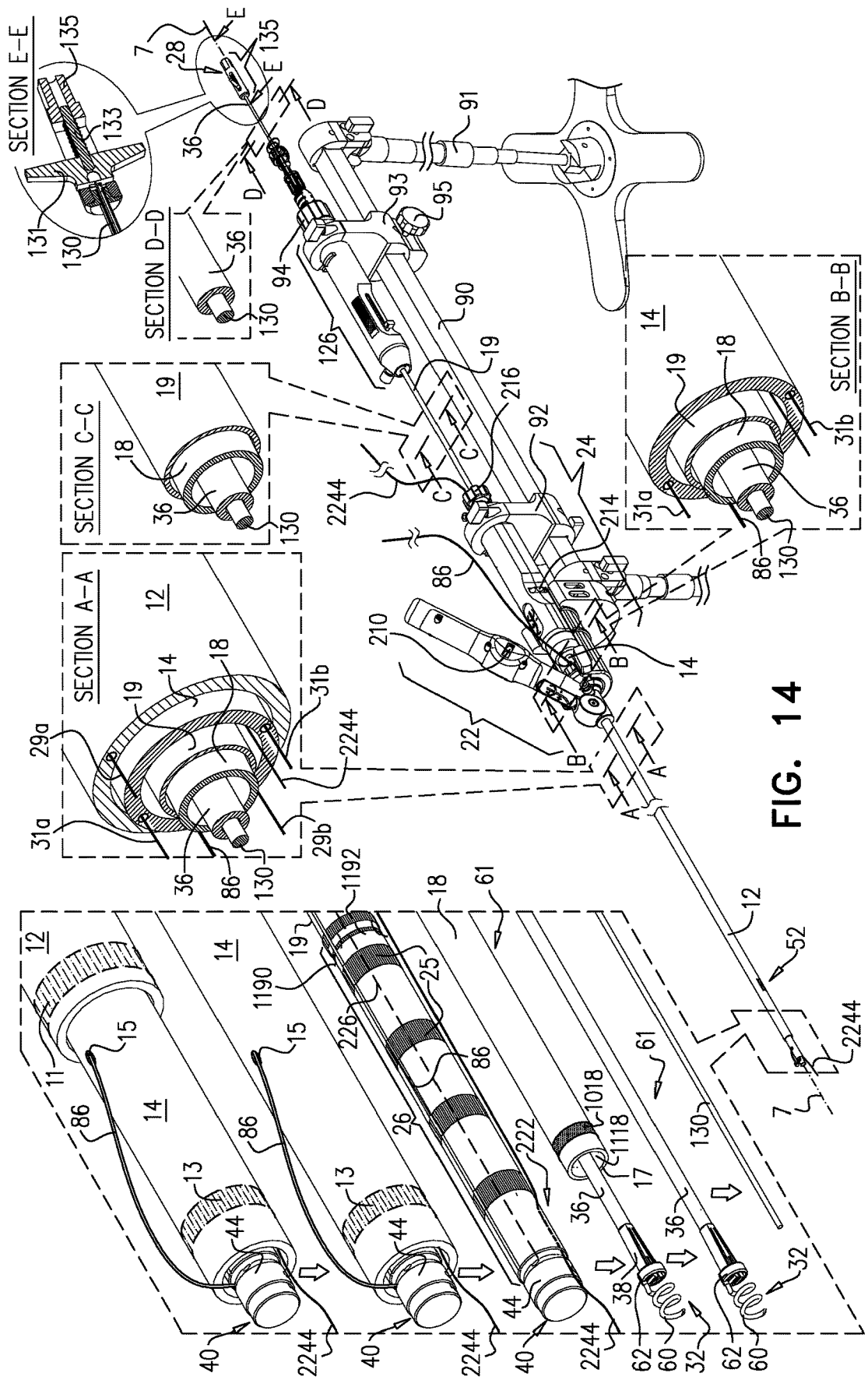

Reference is now made to FIGS. 13-14, which are schematic illustrations of a multi-component tubular system 10 providing one or more rotationally-controlled steering catheters configured for delivering an implant to a heart of a patient, in accordance with some applications of the present invention. System 10 provides an implant-delivery tool. Typically, system 10 comprises a first, outer catheter 12 comprising a sheath configured for advancement through vasculature of a patient. For some applications of the present invention, outer catheter 12 comprises a sheath configured for advancement through a femoral artery toward an interatrial septum of a heart of a patient. A distal steerable end portion of outer catheter 12 is configured to pass through the septum and be oriented in a desired spatial orientation. System 10 comprises a second catheter, or guide catheter 14, comprising a steerable distal end portion. Catheter 14 is configured for advancement through a lumen of outer catheter 12. Outer catheter 12 provides a first coupling 152 (e.g., a slit 52) at a distal portion thereof (e.g., a portion of catheter 12 that is proximal to the steerable distal end portion). Guide catheter 14 comprises a second coupling 154 (e.g., a depressible engager 54 comprising a detent) that is coupled to a displaceable tab 56 coupled to a base. As is described herein, depressible engager 54 (or the second coupling 154) is configured so as to protrude within slit 52 (or the first coupling 152). Thus, slit 52 defines a second-coupling-receiving element.

First coupling 152 of catheter 12 defines a longer coupling, the second coupling 154 of catheter 14 defines a shorter coupling. The first and second couplings 152 and 154 of outer catheter 12 and guide catheter 14, respectively, enable axial advancement and rotational motion of guide catheter 14 through the lumen of outer catheter 12 until engager 54 of catheter 14 is aligned with and engages slit 52 of catheter 12, as will be described hereinbelow. As shown in cross-section A-A of FIG. 13, guide catheter 14 is configured to be concentrically disposed within a lumen of outer catheter 12. It is to be noted that the scope of the present invention includes catheter 12 providing the shorter coupling, and catheter 14 providing the longer coupling. For example, catheter 14 may be shaped so as to provide slit 52, and catheter 12 may comprise engager 54, which is configured to engage slit 52 of catheter 14.

As shown in the exploded view of view B, first coupling 152 is shaped so as to define slit 52. For some applications, slit 52 is provided by a metal frame 50, as shown. Metal frame 50 has a length L22 of between 7 and 15 mm, e.g., 13 mm. For such applications, a slit is created in material of catheter 12 (e.g., by creating a slit in the polymer material of catheter 12 during manufacturing of catheter 12), and frame 50 is coupled to catheter 12. Second coupling 154 comprises an engager 54 which comprises a protrusion disposed at a distal portion of displaceable tab 56 of a base of engager 54. The base of engager 54 is shaped so as to define slits 57 which form tab 56. Engager 54 is depressible when a force is applied thereto, and tab 56 facilitates movement of engager 54 in response to and in the absence of force applied to engager 54. For some applications, during manufacture of catheter 14, catheter 14 is manipulated in order to couple thereto engager 54 and tabs 56, e.g., engager 54 and tabs 56 are embedded within the polymer of catheter 14.

It is to be noted that although slit 52 and depressible engager 54 are shown on outer catheter 12 and guide catheter 14, respectively, at distal portions of catheters 12 and 14, slit 52 and engager 54 may be provided along any suitable portion of catheters 12 and 14, respectively (e.g., a respective proximal portions of catheters 12 and 14).

FIG. 14 shows the concentric relationship between components of tubular system 10 (in an exploded view on the left side of FIG. 14). As described hereinabove, a distal end portion of outer catheter 12 is steerable. The distal end portion of outer catheter 12 comprises a pull ring 11 that is coupled to two or more pull wires 29a and 29b, that are disposed within respective secondary lumens within a wall of catheter 12 (as shown in section A-A). As shown in the exploded view, guide catheter 14 is configured to be concentrically disposed within the lumen of catheter 12. As described hereinabove, the distal end portion of guide catheter 14 is steerable. The distal end portion of catheter 14 comprises a pull ring 13 that is coupled to two or more pull wires 31a and 31b, that are disposed within respective secondary lumens within a wall of catheter 14 (as shown in sections A-A and B-B).

Guide catheter 14 is steerable to a desired spatial orientation in order to facilitate advancing and implantation of an implant in a body cavity of the patient. As shown, the implant comprises an annuloplasty ring structure 222 which defines a longitudinal implant comprising a flexible sleeve 26 (shown in the exploded view of FIG. 14). Sleeve 26 typically comprises a braided fabric mesh, e.g., comprising DACRON™. Sleeve 26 is typically configured to be placed only partially around a cardiac valve annulus (i.e., to assume a C-shape), and, once anchored in place, to be contracted so as to circumferentially tighten the valve annulus. Alternatively, the ring structure is configured to be placed entirely around the valve annulus. In order to tighten the annulus, annuloplasty ring structure 222 comprises a flexible elongated contracting member 226 that extends along sleeve 26. Elongated contracting member 226 comprises a wire, a ribbon, a rope, or a band, which typically comprises a flexible and/or superelastic material, e.g., nitinol, polyester, stainless steel, or cobalt chrome. For some applications, the wire comprises a radiopaque material. For some applications, contracting member 226 comprises a braided polyester suture (e.g., Ticron). For some applications, contracting member 226 is coated with polytetrafluoroethylene (PTFE). For some applications, contracting member 226 comprises a plurality of wires that are intertwined to form a rope structure.

For applications in which system 10 is used to deliver an implant to the mitral valve of the patient, typically, outer catheter 12 is configured for initial advancement through vasculature of the patient until a distal end 102 of catheter 12 is positioned in the left atrium. The distal steerable end portion of catheter 12 is then steered such that distal end 102 of catheter 12 is positioned in a desired spatial orientation within the left atrium. The steering procedure is typically performed with the aid of imaging, such as fluoroscopy, transesophageal echo, and/or echocardiography. Following the steering of the distal end portion of catheter 12, guide catheter 14 (which houses annuloplasty ring structure 222) is advanced through catheter 12 in order to facilitate delivery and implantation of structure 222 along the annulus of the mitral valve. During the delivery, at least a portion of the steerable distal end portion of catheter 14 is exposed from distal end 102 of catheter 12 and is thus free for steering toward the annulus of the mitral valve, as is described hereinbelow.

Annuloplasty ring structure 222 further comprises an adjustment mechanism 40, which facilitates contracting and expanding of annuloplasty ring structure 222 so as to facilitate adjusting of a perimeter of the annulus and leaflets of the cardiac valve. Adjustment mechanism 40 is described in more detail hereinbelow. Adjustment mechanism 40 comprises a rotatable structure (e.g., a spool, as described hereinbelow) that is disposed within a housing 44. As shown in the enlarged image of FIG. 1, adjustment mechanism 40 is surrounded by a braided mesh and is coupled (e.g., by being sutured or otherwise coupled) to the braided mesh of sleeve 26. For some applications, adjustment mechanism 40 is coupled to an outer, lateral surface of sleeve 26. During delivery of sleeve 26 to the annulus of the cardiac valve, sleeve 26 and mechanism 40 are disposed within a lumen of catheter 14 and are aligned longitudinally with a longitudinal lumen of catheter 14. Such coupling of mechanism 40 to sleeve 26 allows mechanism 40 to transition from a state in which it is in line with the longitudinal axis of catheter 14 (FIG. 14) to a state in which it is disposed alongside sleeve 26 (FIG. 13). The positioning of adjustment mechanism 40 alongside a portion of sleeve 26 exposes a driving interface of the rotational structure to be accessed by a rotational tool that is guided toward adjustment mechanism 40 via a guide member 86.

A flexible, longitudinal guide member 86 (e.g., a wire) is coupled to a portion of adjustment mechanism 40 (e.g., a portion of the rotatable structure, as described hereinbelow). Guide member 86 is configured to facilitate guiding of a rotational tool via guide member 86 and toward the rotatable structure of adjustment mechanism 40. Typically, the rotational tool is configured to engage the rotatable structure of adjustment mechanism 40 following implantation of sleeve 26 along the annulus of the cardiac valve. Guide member 86 passes from adjustment mechanism 40, alongside a portion of the distal end portion of guide catheter 14, and into a secondary lumen in the wall of guide catheter 14, through an opening 15 in guide catheter 14. Guide member 86 passes through the secondary lumen of guide catheter 14 (as shown in sections A-A and B-B in FIG. 14) and has a proximal end that is accessible from outside the body of the patient. The secondary lumen in the wall of guide catheter 14 facilitates passage of guide member 86 through system 10 without interfering with the other concentrically-disposed elongate tubular members that pass concentrically through the lumen of guide catheter 14.

In addition, system 10 comprises a plurality of anchors 32, typically between about 5 and about 20 anchors, such as about 10 or about 16 anchors. Each anchor 32 comprises a tissue coupling element 60 (e.g., a helical tissue coupling element), and a tool-engaging head 62, fixed to one end of the tissue coupling element. Only one anchor 32 is shown in FIG. 14 as being reversibly coupled to a deployment element 38 of a rotating anchor driver 36 of an anchor deployment manipulator 61. When sleeve 26 is disposed along the annulus of the cardiac valve, deployment manipulator 61 is configured to advance within a lumen of sleeve 26 and deploy each anchor 32 from within sleeve 26 through a wall of sleeve 26 and into cardiac tissue, thereby anchoring sleeve 26 around a portion of the valve annulus. The insertion of the anchors into the sleeve and deployment of the anchors into cardiac tissue is described in detail hereinbelow.

Typically, but not necessarily, anchors 32 comprise a biocompatible material such as stainless steel 316 LVM. For some applications, anchors 32 comprise nitinol. For some applications, anchors 32 are coated fully or partially with a non-conductive material.

As shown in the exploded view of FIG. 14, sleeve 26 is disposed within a lumen of guide catheter 14. A force is applied to a proximal end of sleeve 26 is by a distal end of a reference-force tube 19. As shown, an implant-decoupling channel 18 is advanceable within a lumen of reference-force tube 19 and through a lumen of sleeve 26. As shown in the enlarged image of FIG. 13, a distal end 17 of implant-decoupling channel 18 is disposed in contact with an inner wall of sleeve 26 at a distal end thereof. Additionally, a distal end portion of channel 18 comprises a radiopaque marker 1018. As shown, tube 19 and sleeve 26 are longitudinally and coaxially disposed with respect to each other.

For some applications, channel 18 is steerable.

Deployment manipulator 61 comprises anchor driver 36 and deployment element 38. Additionally, deployment manipulator comprises channel 18.

Reference is now made to FIGS. 14 and 2. It is to be noted that manipulator 61 shown in FIG. 2 comprises manipulator 61 as described herein with respect to FIG. 14.

Typically, manipulator 61 advances within channel 18. For some applications, system 10 comprises a plurality of anchor drivers 36 of manipulator 61, each driver 36 being coupled to a respective anchor 32. Each driver 36 is advanced within channel 18 in order to advance and implant anchor 32 in tissue. Following implantation of anchor 32, anchor 32 is decoupled from driver 36, as described herein, and driver 36 is removed from within channel 18. Subsequently, a new driver 36 coupled to another anchor 32 is then advanced within channel 18.

As will be described hereinbelow, a first anchor 32 is configured to be deployed through the wall of the sleeve into cardiac tissue, when sleeve 26 is positioned along the annulus of the valve. Following the deployment of the first anchor, a distal portion of sleeve 26 is slid distally off a portion of implant-decoupling channel 18. In order to decouple sleeve 26 distally from a portion of outer surface of channel 18, (1) a proximal force is applied to channel 18, while (2) reference-force tube 19 is maintained in place in a manner in which a distal end of tube 19 provides a reference force to sleeve 26 in order to facilitate freeing of a successive portion of sleeve 26 from around channel 18. Channel 18 is then positioned at a successive location within the lumen of sleeve 26 while either tube 19 and/or catheter 14 is steered toward a successive location along the annulus of the valve (as will be described hereinbelow). Consequently, the successive portion of sleeve 26 provides a free lumen for advancement of a successive anchor 32 and deployment of the anchor through the wall of the sleeve at the successive portion thereof. Such freeing of the successive portion of sleeve 26 creates a distance between successive anchors deployed from within the lumen of sleeve 26.

For some applications, sleeve 26 comprises a plurality of radiopaque markers 25, which are positioned along the sleeve at respective longitudinal sites. The markers may provide an indication in a radiographic image (such as a fluoroscopy image) of how much of the sleeve has been deployed at any given point during an implantation procedure, in order to enable setting a desired distance between anchors 32 along the sleeve. For some applications, the markers comprise a radiopaque ink.

Typically, at least a portion (e.g., at least three, such as all) of the longitudinal sites are longitudinally spaced at a constant interval. Typically, the longitudinal distance between the distal edges of adjacent markers, and/or the distance between the proximal edges of adjacent markers, is set equal to the desired distance between adjacent anchors. For example, the markers may comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance may be between 3 and 15 mm, such as 6 mm, and the longitudinal length of each marker may be between 0.1 and 14 mm, such as 2 mm. (If, for example, the distance were 6 mm and the length were 2 mm, the longitudinal gaps between adjacent markers would have lengths of 4 mm.)

Each anchor 32 is coupled to deployment element 38 of anchor driver 36. Anchor driver 36 comprises an elongate tube having at least a flexible distal end portion. The elongate tube of driver 36 extends within a lumen of channel 18, through system 10 toward a proximal end of a proximal handle portion 101 of system 10, which defines a proximal extracorporeal portion of the apparatus. The tube of anchor driver 36 provides a lumen for slidable advancement therethrough of an elongate rod 130. Rod 130 facilitates the locking and unlocking of anchor 32 to deployment element 38, as is described hereinbelow. As shown in Section E-E of FIG. 14, a proximal end of rod 130 is coupled to a component of an anchor-release mechanism 28 at a proximal end of system 10. Mechanism 28 comprises a housing 135 and a finger-engager 131 that is coupled to the proximal end of rod 130. Finger-engager 131 is coupled to a housing 135 via a spring 133 (section E-E of FIG. 14). A proximal end of the tube of anchor driver 36 is coupled to housing 135. As is described hereinbelow, the physician releases anchor 32 from deployment element 38 when finger-engager 131 is pulled proximally, thereby pulling rod 130 proximally.

Proximal handle portion 101 is supported by a stand having support legs 91 and a handle-sliding track 90. Proximal handle portion 101 defines a proximal extracorporeal portion. Handle portion 101 comprises an outer-catheter handle 22, a guide-catheter handle 24, an implant-manipulating handle 126, and anchor-release mechanism 28. Handle 22 of the proximal extracorporeal portion of handle portion 101 is coupled to a proximal end of outer catheter 12 and functions as a first control mechanism to control catheter 12. Handle 24 of the proximal extracorporeal portion of handle portion 101 is coupled to a proximal portion of guide catheter 14 and functions as a second control mechanism to control catheter 14. Handle 126 is coupled to a proximal portion of reference-force tube 19, and linear movement of handle 126 with respect to handle 24 moves reference-force tube 19 (and thereby typically structure 222) through catheter 14. As described hereinabove, housing 135 of anchor-release mechanism 28 is coupled to a proximal portion of the tube of anchor driver 36. The relative positioning of each of the concentrically-disposed components of system 10 is shown in the exploded view and sections A-A, B-B, C-C, and D-D of FIG. 14.

The stand supporting proximal handle portion 101 may be moved distally and proximally to control a position of the entire multi-component system 10, particularly so as to adjust a distance of distal end 102 of catheter 12 from the interatrial septum. Handle 22 comprises a steering knob 210 that is coupled to steering wires 29*a* and 29*b* disposed within respective secondary lumens in the wall of outer catheter 12. Rotation of knob 210 adjusts a degree of tension of wires 29*a* and 29*b* which, in turn, apply a force to pull ring 11 at the distal end portion of outer catheter 12. Such force steers the distal end portion of catheter 12 within the atrium of the heart of the patient in a manner in which the distal end portion of catheter 12 is steered in a first plane that is parallel with the plane of the annulus of the valve (e.g., in a direction from the interatrial septum toward surrounding walls of the atrium). For some applications of the present invention, the distal end portion of catheter 12 may be pre-shaped so as to point downward toward the valve. For other applications, the distal end portion of catheter 12 may be pulled to assume an orientation in which the distal end portion points downward toward the valve. For yet other applications of the present invention, the distal end portion of catheter 12 is not made to point downward toward the valve.

Handle 24 is coupled to track 90 via a first mount 92. Mount 92 is slidable proximally and distally along track 90 in order to control an axial position of guide catheter 14 with respect to outer catheter 12. Mount 92 is slidable via a control knob 216. For example, control knob 216 of mount 92 controls the proximal and distal axial movement of the distal steerable portion of guide catheter 14 with respect to distal end 102 of outer catheter 12. Handle 24 comprises a steering knob 214 that is coupled to steering wires 31*a* and 31*b* disposed within respective secondary lumens in the wall of guide catheter 14. Rotation of knob 214 adjusts a degree of tension of wires 31*a* and 31*b* which, in turn, apply a force to pull ring 13 at the distal end portion of guide catheter 14. Such force steers the distal end portion of catheter 14 in a second plane within the atrium of the heart of the patient downward and toward the annulus of the cardiac valve. Typically, as described hereinbelow, the distal end portion of guide catheter 14 is steered in the second plane that is substantially perpendicular with respect to the first plane in which the distal end portion of outer catheter 12 is steered.

The combined steering of the respective distal end portions of catheters 12 and 14 directs sleeve 26 down toward the annulus (e.g., via the steering of the distal end portion of catheter 14) and along the perimeter of annulus (e.g., from the posterior section of the valve to the anterior section of the valve, and vice versa), via the steering of the distal end portion of catheter 12.

For some applications, handle 22 may be tilted by the operating physician, in order to further adjust a position of the distal end of catheter 12.

As described herein, first and second couplings 152 and 154 of outer catheter 12 and guide catheter 14, respectively (e.g., slit 52 and engager 54, respectively), provide a controlled steerable system in which, during the steering and bending of the distal end portion of guide catheter 14, the distal end portion of outer catheter 12 is maintained in its steered configuration, or in its spatial orientation, without substantially affecting the steering or the bending of the distal end portion of guide catheter 14. Thus, first and second couplings 152 and 154, respectively, minimize the effect of the distal end portion of outer catheter 12 on the steering and bending of catheter 14. That is, first and second couplings 152 and 154 of outer catheter 12 and guide catheter 14, respectively, collectively define a relative-spatial-orientation-controlling device which rotationally locks the relative spatial orientation of the steerable distal end portion and the bending section of outer catheter 12 with respect to the steerable distal end portion and the bending section of guide catheter 14.

Guide member 86 exits from the lumen in the wall of guide catheter 14 at a portion of handle portion 101 that is between handles 22 and 24.

Handle 126 is coupled to track 90 via a second mount 93. Mount 93 is slidable proximally and distally along track 90, in order to control an axial position of reference-force tube 19 and at least a proximal portion of sleeve 26 with respect to guide catheter 14. Mount 93 is slidable via a control knob 95. For example, control knob 95 of mount 93 controls the proximal and distal axial movement of the tube 19 and at least the proximal portion of sleeve 26 with respect to distal end 104 of guide catheter 14. Taken together with the steering of the distal end portion of guide catheter 14, such movement of tube 19 and at least the proximal portion sleeve 26 moves the proximal portion of sleeve 26 toward a desired portion of tissue of the annulus of the valve during deployment of anchors 32 from within the lumen of sleeve 26, as is described hereinbelow.

As is described hereinabove, in order to decouple sleeve 26 from a portion of an outer surface of channel 18, (1) channel 18 is pulled proximally, while (2) reference-force tube 19 is maintained in place. A proximal end of channel 18 is coupled to a knob 94 which adjusts an axial position of channel 18 proximally and distally with respect to reference-force tube 19 and sleeve 26.

Typically, handle portion 101 comprises a release decision facilitation member 127, such as a latch or button, that automatically engages when a given length of sleeve 26 has advanced off channel 18 (e.g., when channel 18 is at a given position with respect to tube 19); typically just before sleeve 26 becomes completely decoupled from channel 18. Engagement of member 127 inhibits proximal movement of channel 18 with respect to tube 19, thereby reducing a likelihood of (e.g., preventing) inadvertent release of sleeve 26. In order to release sleeve 26 (e.g., to decouple channel 18 from the sleeve), the operating physician must disengage member 127, such as by pushing the button, before continuing to withdraw channel 18 proximally. Typically, when engaged, member 127 also inhibits distal movement of channel 18 with respect to tube 19.

Handle portion 101 (comprising handles 22, 24, and 126 and anchor-release mechanism 28) has a length L1 of between 65 and 85 cm, e.g., 76 cm. Typically, as shown, a majority of the body portion of outer-catheter handle 22 is disposed at a non-zero angle with respect to a longitudinal axis 7 of the multiple components of system 10. The steering mechanism provided by handle 22 in order to steer the distal end portion of catheter 12 is disposed within the portion of handle 22 that is disposed at the non-zero angle with respect to axis 7. Handle 22 comprises an in-line tubular portion 21 which is longitudinally disposed in-line along axis 7 and coaxially with respect to handles 24 and 126 and release mechanism 28. Tubular portion 21 is shaped so as to define a lumen for inserting guide catheter 14 therethrough and subsequently into the lumen of outer catheter 12 (as is described hereinbelow with reference to FIG. 15A). Tubular portion 21 has a length L24 of between 7 and 11 cm, e.g., 7 cm. Such spatial orientation of the majority of handle 22 at an angle with respect to axis 7 reduces an overall functional length of handle portion 101.

Figure 15A:
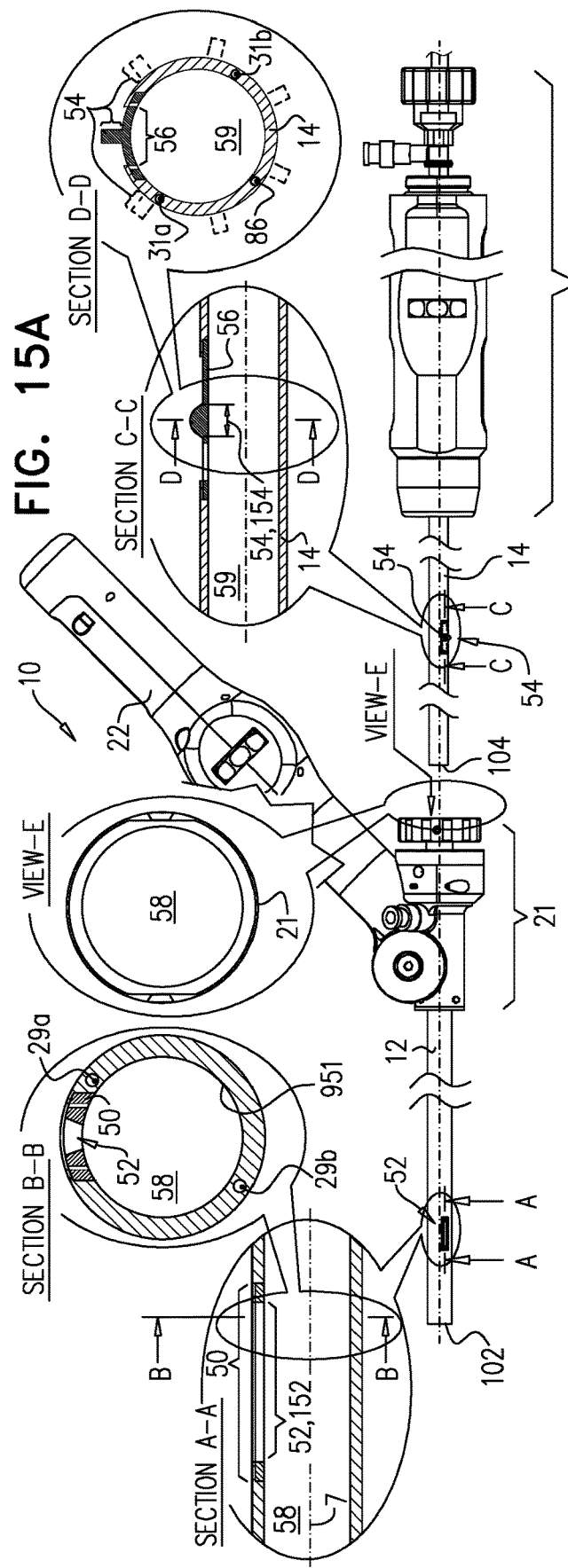

Reference is now made to FIGS. 15A-E, which are schematic illustrations of the functional relationship between first and second couplings 152 and 154, respectively, and respective degrees of rotational freedom of guide catheter 14 with respect to outer catheter 12, in accordance with some applications of the present invention. It is to be noted that FIGS. 15A-E show a functional relationship between catheters 12 and 14, and, for clarity of illustration, does not show the concentric components disposed within a longitudinal lumen 59 of catheter 14 (i.e., reference-force tube 19, channel 18, anchor driver 36, and rod 130, as shown in FIGS. 13 and 14). FIG. 15A shows catheters 12 and 14 in a state prior to advancing catheter 14 through a lumen 58 of catheter 12. Sections A-A and B-B of FIG. 15A show slit 52, or first coupling 152, empty. Section C-C shows a portion of catheter 14 which provides engager 54, or second coupling 154. As described hereinabove with reference to FIG. 13, engager 54 is coupled to a depressible tab 56 which facilitates depressible movement of engager 54 when a force is applied thereto (e.g., at a later stage by an inner wall 951 of catheter 12 that surrounds lumen 58 when catheter 14 is advanced through lumen 58, as is described hereinbelow). As shown in section C-C of FIG. 15A, in the absence of a pushing force, tab 56 is disposed in parallel with longitudinal axis 7, and engager 54 is in a resting state thereof in which engager 54 is not in a depressed state and protrudes from an external surface of catheter 14.

Figure 15B:
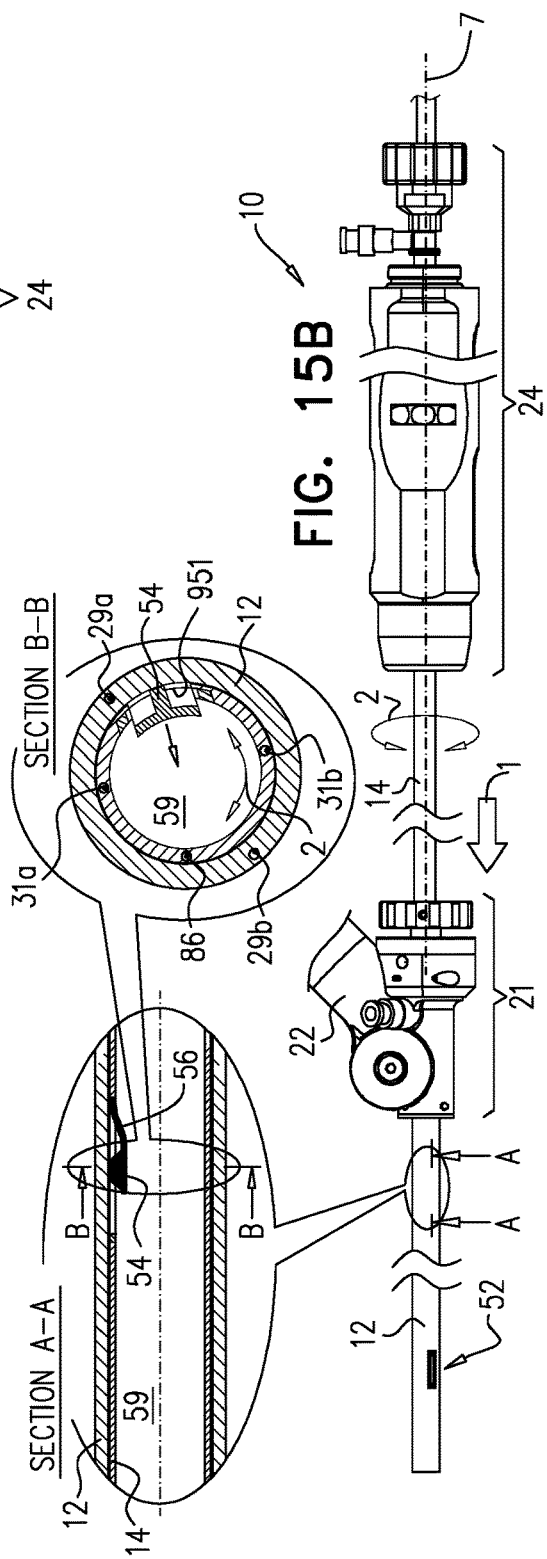

As shown in sections A-A and B-B of FIGS. 15A-B, first coupling 152 is provided in a manner in which lumen 58 of catheter 12 is free from any protrusions. Additionally, inner wall 951 of catheter 12 is not shaped to define any interrupted portions, such as recessed portions, along a proximal portion of catheter 12 and extending toward distal end 102 of catheter 12, except for slit 52 at a distal portion thereof. Once catheter 12 is advanced through the vasculature of the patient, distal end 104 of catheter 14 is configured to enter a lumen provided by tubular portion 21 of handle 22, and subsequently, catheter 14 passes through lumen 58 of catheter 12. View E is a view of lumen 58 of catheter 12 from a proximal portion of tubular portion 21 of handle 22. Since lumen 58 is free from any protrusions or recessed portions, as described hereinabove, and since engager 54 is depressible by tab 56, catheter 14 is configured to enter lumen 58 of catheter 12 in any rotational configuration thereof. Catheter 14 is shown in section D-D in a manner in which engager is oriented at 12 o'clock, by way of illustration and not limitation. Catheter 14 may enter lumen 58 of catheter 12 in any rotational configuration thereof, therefore, engager 54 is shown in phantom in a plurality of orientations in section D-D, since catheter 14 may enter lumen 58 of catheter 12 in a rotational orientation in which engager 54 may be oriented in any given orientation with respect to inner wall 951 of catheter 12.

During the insertion of distal end 104 and the distal portion of catheter 14, the physician pushes down on engager 54 such that engager 54 fits within the lumen of catheter 12. In response to the pushing force on engager 54, tab 56 is pushed downward as well.

Typically, catheter 12 has an inner diameter (or the diameter of lumen 58) of between 6.5 and 7.0 mm (e.g., 6.85 mm). Typically, catheter 14 has an inner diameter (or the diameter of lumen 59) of between 4.7 and 5.3 mm (e.g., 5.1 mm). System 10, by providing slit 52 and depressible engager 54, provides a system in which the inner diameters of catheters 12 and 14 are maintained during given stages of the procedure. For example, engager 54 maintains the inner diameter of catheter 12 as catheter 14 is advanced within the lumen of catheter 12, and slit 52 maintains the inner diameter of catheter 14 once engager 54 pops up and is disposed within slit 52.

FIG. 15B shows the axial advancement of a distal portion of catheter 14 through the lumen of catheter 12 in the direction as indicated by arrow 1. Typically, the advancement of catheter 14 through catheter 12 is controlled by the physician who moves handle 24 axially closer to handle 22. During the advancement of catheter 14 through catheter 12, engager 54 is maintained in a pushed state (as shown in section A-A of FIG. 15B) by a pushing force applied thereto by inner wall 951 of catheter 12. As shown in section B-B of FIG. 15B, inner wall 951 of outer catheter 12 pushes on engager 54, in the direction as indicated by the radial arrow. In response to the force applied on engager 54 by inner wall 951 of catheter 12, engager 54 is pushed and tab 56 is displaced at a non-zero angle with respect to axis 7 in order to allow for depression of engager 54. During the depression of engager 54, engager 54 is pushed slightly within lumen 59 of catheter 14.

As described hereinabove, inner wall 951 of catheter 12 is smooth and uninterrupted by recesses or slits (except for slit 52 at the distal end of catheter 12). Typically, slit 52 has a length L2 (shown in view B of FIG. 13) of between 5 and 15 mm, e.g., 10 mm. A proximal-most end of slit 52 is disposed up to 100 mm (e.g., up to 60 mm) from distal end 102 of catheter 12. Catheter 12 is typically between 80 and 100 cm long. Thus, inner wall 951 of the proximal portion of catheter 12, until the proximal-most end of slit 52, is smooth and uninterrupted by recesses or slits. Taken together, the depressibility of engager 54 and such a smooth configuration of inner wall 951 of catheter 12 enables rotation of catheter 14 by 360 degrees (i.e., as indicated by arrow 2) within the lumen of catheter 12.

FIG. 15C shows further axial advancement of catheter 14 within the lumen of catheter 12. As described hereinabove, during the advancement, and prior to the engaging of engager 54 with slit 52 (as is described hereinbelow with reference to FIG. 15D), inner wall 951 pushes on engager 54 such that catheter 14 can be rotated to any suitable rotational orientation within outer catheter 12. For example, engager 54 is shown at 2 o'clock in section B-B of FIG. 15B, while engager 54 is shown at 11 o'clock in section B-B of FIG. 15C. Furthermore, prior to the engaging of engager 54 with slit 52 catheter 14 may be extracted from within the lumen of catheter 12.

FIG. 15C shows axial advancement of catheter 14 within catheter 12 in the distal direction, as indicated by arrow 1, in a manner in which engager 54 is about to engage with slit 52 at a distal portion of catheter 12. FIG. 15C shows a relative position of catheter 14 with respect to catheter 12 in a manner in which catheter 14 is not fully pushed within catheter 12. Handle 24 of catheter 14 is still distanced from handle 22 of catheter 12. However, catheter 14 is pushed distally sufficiently for distal end 104 and a portion of the distal end portion of catheter 14 to emerge from within catheter 12 and extend distally beyond distal end 102 of catheter 12.

Following further distal advancement of catheter 14 within catheter 12, and slight rotation of catheter 14 within the lumen of catheter 12, engager 54 of catheter 14 is aligned with slit 52 of catheter 12, as shown in FIG. 15D. In the absence of the pushing force of inner wall 951 of catheter 12 on engager 54, engager 54 returns to its resting state and protrudes within slit 52 so as to engage slit 52. That is, first coupling 152 is engaged with second coupling 154. As engager 54 returns to its resting state, tab 56 returns to a position in which it is parallel with respect to longitudinal axis 7.

FIG. 15D shows engager 54 in a distal-most position within slit 52, i.e., a fully-pushed state of catheter 14. As such, handles 24 and 22 are disposed adjacently to each other. In this state, an exposed distal end portion 114 of catheter 14 extends beyond distal end 102 of catheter 12. Typically, at least a portion of distal end portion 114 is steerable and bendable, as is described hereinbelow. Distal end portion 114 of catheter 14 has a length L3 of between 25 and 35 mm, e.g., 30 mm. As described hereinabove, slit 52 has a length L2 of between 5 and 15 mm, e.g., 10 mm.

Reference is now made to FIGS. 13 and 3D. As shown in view B of FIG. 13, engager 54 has a longitudinal length L26 of between 2 and 3 mm, e.g., 2 mm. Length L26 facilitates motion of engager 54 along length L2 of slit 52. A proximal-most end of engager 54 is disposed up to 120 mm (e.g., up to 80 mm) from distal end 104 of catheter 14. As described hereinabove, a proximal-most end of slit 52 is disposed up to 100 mm (e.g., up to 60 mm) from distal end 102 of catheter 12. Thus, since slit 52 has a length L2 of between 5 and 15 mm, e.g., 10 mm, when engager 54 is disposed at a distal-most position within slit 52, as shown in FIG. 15D, exposed distal end portion 114 of catheter 14 has a length L3 of between 20 and 35 mm, e.g., 30 mm.

For some applications, the combined lengths of first and second couplings 152 and 154, respectively, is less than 30 mm, e.g., less than 20 mm. For applications in which first coupling 152 (e.g., slit 52) is between 5 and 15 mm, and second coupling 154 (e.g., engager 54) is between 2 and 3 mm, the combined lengths of first and second couplings 152 and 154, respectively, is less than 50 mm, e.g., less than 20 mm.

Engager 54 has a longitudinal length L26 that is less than 30% (e.g., less than 20%) of the longitudinal length of catheter 14. Typically, however, as described hereinabove, engager 54 has a length L26 of between 2 and 3 mm. That is, engager 54 has a longitudinal length that is less than 2% (e.g., less than 1%) of the longitudinal length of catheter 14.

Reference is now made to FIGS. 15C-D. A portion of exposed distal end portion 114 extends beyond distal end 102 of catheter 12 prior to engager 54 engaging slit 52. The length L2 of slit 52 enables retraction of catheter 14 between 5 and 15 mm, proximally from the fully-pushed state of catheter 14. As catheter 14 is retracted proximally, engager 54 moves proximally within slit 52 until a proximal-most end of engager 54 contacts a proximal-most end of slit 52. When engager 54 is disposed at the proximal-most end of slit 52, the distal end portion exposed from within catheter 12 is between 10 and 30 mm, e.g., 20 mm. When catheter 14 is pushed distally, engager 54 moves distally within slit 52 until a distal-most end of engager 54 contacts a distal-most end of slit 52.

Reference is again made to FIG. 15D. In the state in which engager 54 is disposed within slit 52, catheter 14 is restricted from rotating within the lumen of catheter 12, and catheters 12 and 14 are thereby rotationally locked with respect to each other.

FIG. 15E shows catheter 12 and 14 in a state in which catheter 14 has been pushed fully within catheter 12 (i.e., a state in which engager 54 is disposed at a distal-most end of slit 52 and handle 24 is disposed adjacently to handle 22). As described hereinabove, during the fully-pushed state of catheter 14, exposed distal end portion 114 extends beyond distal end 102 of catheter 12 and has a length L3 of between 25 and 35 mm, e.g., 30 mm. Additionally, as is described herein, at least a portion of distal end portion 114 is steerable and comprises an exposed bending section 1403 which is a portion of a collective distal bending section 1405 of catheter 14 (described hereinbelow with reference to FIGS. 17 and 18). A distal end portion of catheter 12 comprises a bending section 1203 (described hereinbelow with reference to FIGS. 16 and 18). A proximal portion of bending section 1405 of catheter 14 is bendable and disposed within the lumen of catheter 12 at bending section 1203 thereof.

The distal end portion of catheter 12 is steerable in a first plane (e.g., a plane that is parallel with respect to the cardiac valve of the patient). Bending section 1403 of exposed distal end portion 114 (and additional portions of collective bending section 1405) is steerable in second plane that is substantially perpendicular to the first plane in which the distal end portion of catheter 12 is steerable (e.g., a plane that is perpendicular with respect to the valve of the patient). As shown, bending section 1203 of the steerable distal end portion of outer catheter 12 is maintained in its steered configuration, or in its spatial orientation, without substantially affecting the steering of exposed distal end portion 114 of guide catheter 14, nor of the bending of bending section 1403, nor of the collective bending section 1405 (including the proximal portion of bending section 1405 of catheter 14 that is disposed within the lumen of catheter 12 at bending section 1203 thereof). That is, first and second couplings 152 and 154, respectively, advantageously reduce the effect of the distal end portion of catheter 12 on the steering of distal end portion 114 and the bending of bending section 1405. That is, first and second couplings 152 and 154 of outer catheter 12 and guide catheter 14, respectively, collectively define a relative-spatial-orientation-controlling device which rotationally locks the relative spatial orientation of the steerable distal end portion and bending section 1203 of outer catheter 12 with respect to the steerable distal end portion and bending section 1405 of guide catheter 14, specifically of exposed bending section 1403.

Thus, for applications in which system 10 is used to treat the mitral valve, bending section 1203 of catheter 12 bends the steerable distal end portion of catheter 12 within the atrium in the first plane that is parallel with respect to the mitral valve. First and second couplings 152 and 154, respectively, enable (1) bending of bending section 1405 toward the valve in the second plane that is substantially perpendicular with respect to the first plane and to the plane of the mitral valve, while (2) restricting or minimizing the effect of the spatial orientation of bending section 1203 of catheter 12 on bending section 1405 of catheter 14.

Reference is now made to FIGS. 15A-E. It is to be noted that for some applications, slit 52 has a longitudinal length L2 of less than 20 cm, e.g., a length of less than 15 cm. That is, slit 52 has a longitudinal length L2 that is less than 30% (e.g., less than 20%) of the longitudinal length of catheter 12. Typically, however, as described hereinabove, slit 52 has a length L2 of between 5 and 15 mm, e.g., 10 mm. That is, slit 52 has a longitudinal length that is less than 2% (e.g., less than 1%) of the longitudinal length of catheter 12. For such applications, the proximal-most end of slit 52 is disposed up to 30 mm from distal end 102 of catheter 12.

It is to be noted that the scope of the present invention includes providing slit 52 and engager 54 at respective proximal portions of catheters 12 and 14, respectively. For such applications, a distal-most end of slit 52 is disposed up to 100 mm (e.g., up to 60 mm) from the proximal end of catheter 12 and a distal-most end of engager 54 is disposed up to 120 mm (e.g., up to 80 mm) from the proximal end of catheter 14.

Reference is now made to FIGS. 13, 14, and 15A-E. It is to be noted that first and second couplings 152 and 154, respectively, may be provided on any standard catheter. That is, coupling 152 comprises frame 50 which can be coupled to an external surface of any standard catheter (in which case, a corresponding slit would be made in the standard catheter). Additionally coupling 154 may be coupled to any standard catheter by coupling the base portion of coupling 154 to any standard catheter. Suitable adjustments to the standard catheter would be made to accommodate the displacing of tab 56 and engager 54 in response to pushing forces applied to engager 54.

Figure 16:
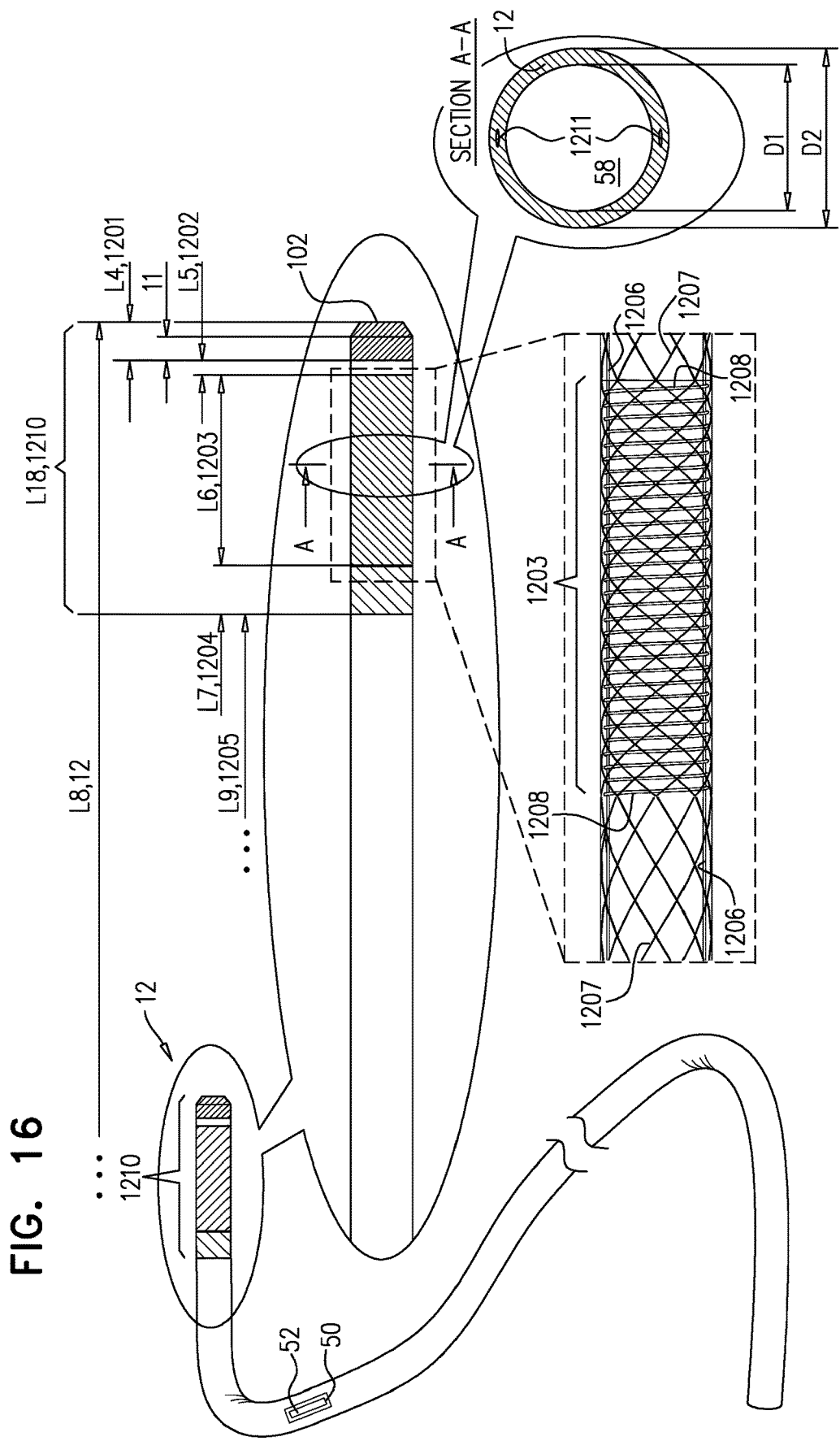
FIGS. 16-18 are schematic illustrations of components of the catheter system of FIGS. 13-14, in accordance with some applications of the present invention.

Reference is now made to FIG. 16, which is a schematic illustration of catheter 12 comprising a multiple-durometer section 1210 at a distal steerable end portion of catheter 12, in accordance with some applications of the present invention. Multiple-durometer section 1210 has a length L18 of between 30 mm and 40 mm, e.g., 36 mm. Each section of multiple-durometer section 1210 has a respective durometer sections in Shore D, or scale D. Catheter 12 comprises a uniform durometer section 1205 that is disposed proximal to multiple-durometer bending section 1210. Typically, multiple durometer section 1210 and uniform durometer section 1205 comprise an elastic tubular polymer 1206 (e.g., sequences of polyamide 12 segments (PA12) and polytetramethylene glycol segments (PTMG), polyether block amide, or PEBA) that defines the tubular structure of catheter 12. Polymer 1206 has mechanical and dynamic properties which impart flexibility, impact resistance, energy return, and fatigue resistance to catheter 12.

As shown in the cross-sectional image, catheter 12 provides a wall which defines lumen 58. The inner wall of catheter 12 (which defines lumen 58) is coated with a friction-reducing liner comprising polytetrafluoroethylene (PTFE) so as to reduce friction during the sliding of catheter 14 through lumen 58 of catheter 12. The wall of catheter 12 is shaped so as to define secondary lumens 1211, which are typically spaced apart from each other by 180 degrees. A respective pull wire 29a and 29b (not shown in FIG. 16 for clarity of illustration, but are shown in FIGS. 13 and 14) is advanced through each lumen 1211. The inner walls of each secondary lumen 1211 is coated with a friction-reducing liner comprising polytetrafluoroethylene (PTFE) so as to reduce friction during the sliding of respective wires 29a and 29b therethrough.

Typically, catheter 12 has an inner diameter D1 (or the diameter of lumen 58) of between 6.5 and 7.0 mm (e.g., 6.85 mm) and outer diameter D2 of between 8.0 and 9.0 mm (e.g., 8.3 mm).

It is to be noted that even though catheter 12 has multiple durometer segments, inner and outer diameters D1 and D2, respectively, remain constant along a longitudinal length L8 of catheter 12 (with the exception of outer diameter D2 being tapered at the distal end portion of section 1201, as is described hereinbelow).

Typically, catheter 12 has a longitudinal length L8 of between 800 and 900 mm, e.g., between 853 and 867 mm, e.g., 860 mm. Uniform durometer section 1205 has a length L9 that is between 770 and 860 mm, e.g., 824 mm. Tubular polymer 1206 extends an entire length L8 of catheter 12. Catheter 12 is surrounded by a braided mesh 1207, which typically comprises a flexible metal (e.g., stainless steel 304 or nitinol). Typically, braided mesh 1207 extends along the length of catheter 12 until a proximal portion at which the pull wires 29a and 29b (not shown for clarity of illustration) are exposed from within lumens 1211 at a proximal section of catheter 12, e.g., between 823 and 837 mm (e.g., 830 mm) from distal end 102 of catheter 12.

Section 1210 comprises a distal pull-ring section 1201 in which pull ring 11 is disposed. Typically, a distal-most portion of section 1201 is tapered so as to facilitate atraumatic advancement of catheter 12 through the vasculature of the patient. Section 1201 has a length of between 4 and 5 mm (e.g., 4.5 mm) and has a durometer of between 45 D and 63 D (e.g., 55 D). Such a durometer of section 1201 imparts more hardness and rigidity to the distal portion of catheter 12 in which pull ring 11 is disposed, such that section 1201 supports ring 11 and protects the distal portion of catheter 12 from the impact of forces applied thereto during the pulling of pull ring 11 by the pull wires. Typically, pull ring 11 has a length of between 2.5 and 2.6 mm, e.g., 2.54 mm. A distal transition section 1202 is disposed proximal to section 1201 and has a length L5 of between 1 and 2 mm (e.g., 1.5 mm) and has a durometer of between 63 D and 72 D (e.g., 72 D). The relatively high durometer of section 1202 imparts hardness to section 1202 such that pull ring 11 is supported and maintained in place during the pulling of pull ring 11 by the pull wires. Thus, section 1202 helps overcome high tensile forces acting on the distal end of catheter 12.

Catheter 12 provides bending section 1203 proximally adjacent to section 1202. As shown in the enlarged image, bending section 1203 comprises a coil 1208 which is embedded within the tubular polymer 1206. Typically, coil 1208 comprises a flexible metal (e.g., stainless steel 304 or nitinol). Coil 1208 imparts efficient and durable bending to bending section 1203. Additionally, polymer 1206 at bending section 1203 has a durometer of between 25 D and 45 D (e.g., 35 D) which provides a degree of softness that facilitates bending of the distal steerable portion of catheter 12 at bending section 1203. Bending section 1203 has a length L6 of between 22 and 27 mm, e.g., 25 mm.

Typically, bending section 1203 has a maximum bending angle between 120 and 140 degrees (e.g., 127 degrees). That is, bending section 1203 can bend between 0 and 140 degrees. For some applications, bending section 1203 has a pre-shaped angle of between 40 and 55 degrees (e.g., 45 degrees) so as to reduce force applied to bending section 1203 of catheter 12 by pull wires 29a and 29b.

It is to be noted that only tubular polymer 1206 and braided mesh 1207 extend proximally and distally beyond bending section 1203.

Proximally adjacent to bending section 1203 is a transition section 1204 having a length L7 of between 4 and 6 mm (e.g., 5 mm). Proximally adjacent to transition section 1203 is uniform durometer section 1205. Uniform durometer section 1205 has a durometer of between 63 D and 72 D (e.g., 72 D). Transition section 1204 has a durometer of between 35 D and 55 D (e.g., 45 D) so as to provide a transition from the relatively low durometer of bending section 1203 to the relatively high durometer of uniform durometer section 1205.

FIG. 16 shows the relative position of slit 52 with respect to distal end 102 of catheter 12. As described hereinabove, a proximal-most end of slit 52 is disposed up to 100 mm (e.g., up to 60 mm) from distal end 102 of catheter 12.

Typically, the spatial orientation of bending section 1203 is determined by pulling on pull wires 29a and 29b that are disposed within lumens 1211 (wires 29a and 29b are not shown for clarity of illustration). Bending section 1203, for some alternative applications of the present invention, may be pre-shaped (e.g., at 45 degrees with respect to a transverse plane provided by opposing pull wires 29a and 29b) to assume a given spatial orientation and the spatial orientation of section 1203 is additionally determined by pulling on pull wires 29a and 29b.

Figure 17:
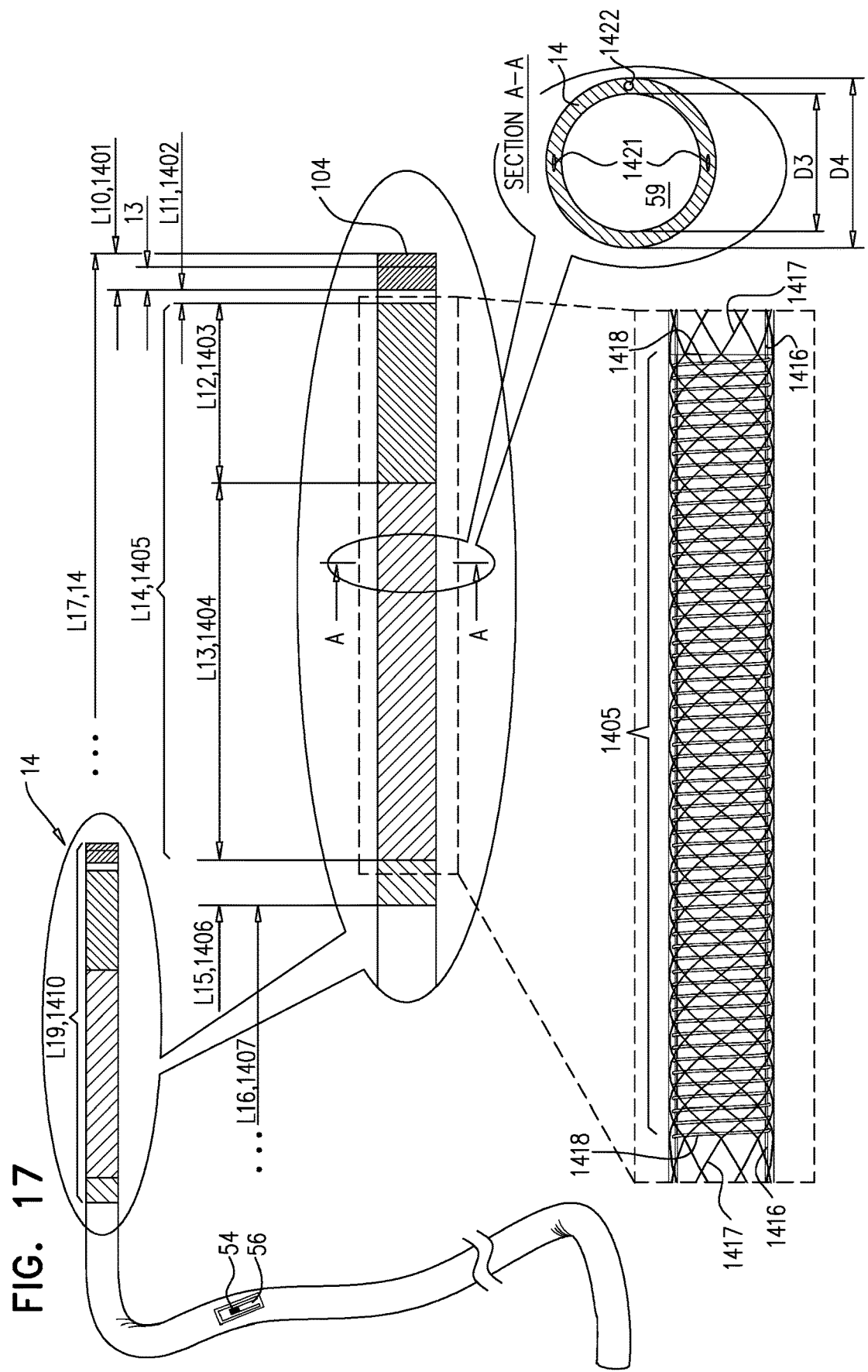

Reference is now made to FIG. 17, which is a schematic illustration of catheter 14 comprising a multiple-durometer section 1410 at a distal steerable end portion of catheter 14, in accordance with some applications of the present invention. Multiple-durometer section 1410 has a length L19 of between 70 mm and 80 mm, e.g., 74 mm. Each section of multiple-durometer section 1410 has a respective durometer sections in Shore D, or scale D. Catheter 14 comprises a uniform durometer section 1407 that is disposed proximal to multiple-durometer bending section 1410. Typically, multiple durometer section 1410 and uniform durometer section 1407 comprise an elastic tubular polymer 1416 (e.g., sequences of polyamide 12 segments (PA12) and polytetramethylene glycol segments (PTMG), polyether block amide, or PEBA) that defines the tubular structure of catheter 14. Polymer 1416 has mechanical and dynamic properties which impart flexibility, impact resistance, energy return, and fatigue resistance to catheter 14.

As shown in the cross-sectional image, catheter 14 provides a wall which defines lumen 59. The inner wall of catheter 14 (which defines lumen 59) is coated with a friction-reducing liner comprising polytetrafluoroethylene (PTFE) so as to reduce friction during the sliding of tube 19 (not shown for clarity of illustration, but shown in FIGS. 13 and 14) through lumen 59 of catheter 14. The wall of catheter 14 is shaped so as to define secondary lumens 1421, which are typically spaced apart from each other by 180 degrees. A respective pull wire 31*a* and 31*b* (not shown in FIG. 5 for clarity of illustration, but are shown in FIGS. 13 and 14) is advanced through each lumen 1421. The inner walls of each secondary lumen 1421 is coated with a friction-reducing liner comprising polytetrafluoroethylene (PTFE) so as to reduce friction during the sliding of respective wires 31*a* and 31*b* therethrough. Additionally, the wall of catheter 14 is shaped so as to define a secondary lumen 1422 for passage therethrough of guide member 86 (not shown in FIG. 17 for clarity of illustration, but are shown in FIGS. 13 and 14). The inner wall of secondary lumen 1422 is coated with a friction-reducing liner comprising polytetrafluoroethylene (PTFE) so as to reduce friction during the sliding of guide member 86 therethrough.

Typically, catheter 14 has an inner diameter D3 (or the diameter of lumen 59) of between 4.7 and 5.3 mm (e.g., 5.1 mm) and outer diameter D4 of between 6.3 and 6.9 mm (e.g., 6.5 mm or 6.7 mm).

It is to be noted that even though catheter 14 has multiple durometer segments, inner and outer diameters D3 and D4, respectively, remain constant along a longitudinal length L17 of catheter 14.

Typically, catheter 14 has a length L17 of between 1000 and 1500 mm, e.g., between 1190 and 1210 mm, e.g., 1200 mm. Uniform durometer section 1407 has a length L16 that is between 900 and 1400 mm, e.g., between 1110 and 1130 mm, e.g., 1126 mm. Tubular polymer 1416 extends an entire length L17 of catheter 14. Catheter 14 is surrounded by a braided mesh 1417, which typically comprises a flexible metal (e.g., stainless steel 304 or nitinol). Typically, braided mesh 1417 extends along the length of catheter 14 until a proximal portion at which the pull wires 31*a* and 31*b* (not shown for clarity of illustration) are exposed from within lumens 1421 at a proximal section of catheter 14, e.g., between 993 and 1007 mm (e.g., 1000 mm) from distal end 104 of catheter 14.

Section 1410 comprises a distal pull-ring section 1401 in which pull ring 13 is disposed. Section 1401 has a length of between 3.5 and 4.5 mm (e.g., 4.04 mm) and has a durometer of between 45 D and 63 D (e.g., 55 D). Such a durometer of section 1401 imparts more hardness and rigidity to the distal portion of catheter 14 in which pull ring 13 is disposed, such that section 1401 supports ring 13 and protects the distal portion of catheter 14 from the impact of forces applied thereto during the pulling of pull ring 13 by the pull wires. Typically, pull ring 13 has a length of between 2.5 and 2.6 mm, e.g., 2.54 mm. A distal transition section 1402 is disposed proximal to section 1401 and has a length L11 of between 1 and 2 mm (e.g., 1.5 mm) and has a durometer of between 63 D and 72 D (e.g., 72 D). The relatively high durometer of section 1402 imparts hardness to section 1402 such that pull ring 13 is supported and maintained in place during the pulling of pull ring 13 by the pull wires. Thus, section 1402 helps overcome high tensile forces acting on the distal end of catheter 14.

Catheter 14 provides collective bending section 1405 proximally adjacent to section 1402. As shown in the enlarged image, bending section 1405 comprises a coil 1418 which is embedded within the tubular polymer 1416. Typically, coil 1418 comprises a flexible metal (e.g., stainless steel 304 or nitinol). Coil 1418 imparts efficient and durable bending to bending section 1405. Bending section 1405 has a length L14 of between 60 and 70 mm, e.g., 62 mm. Collective bending section 1405 comprises exposed bending section 1403 and a proximal bending section 1404.

Figure 18:
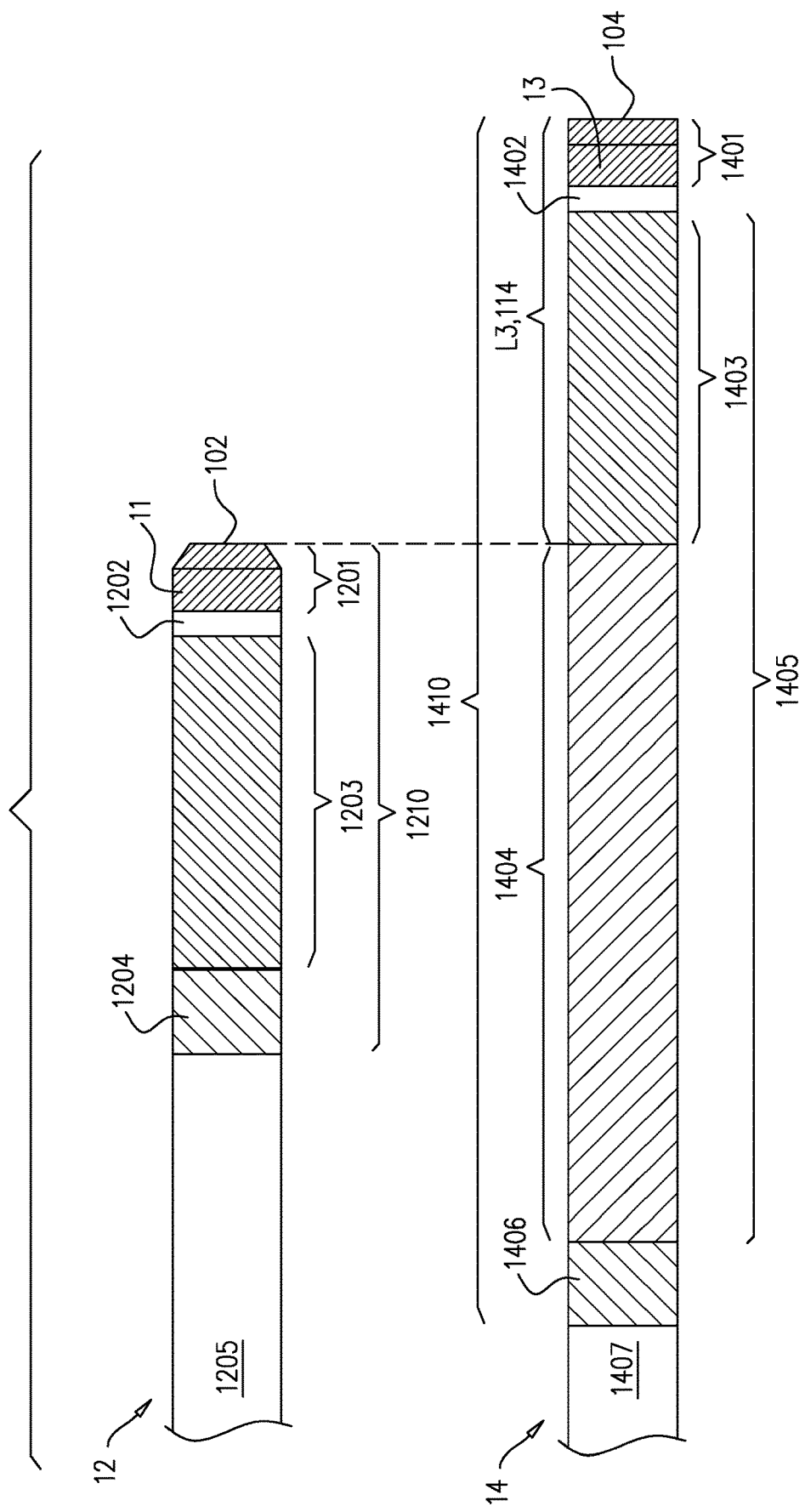

Reference is now made to FIG. 18, which is a schematic illustration of a relative spatial orientation of the steerable distal end portions of catheters 12 and 14, respectively. Typically, in a fully-pushed state of catheter 14 within catheter 12, as described hereinabove, catheter 14 provides exposed distal end portion 114 that extends beyond distal end 102 of catheter 12. Distal end portion 114 comprises exposed bending section 1403. In the fully-pushed state of catheter 14, exposed bending section 1403 is configured to be exposed from and extend beyond distal end 102 of catheter 12, while at least a distal portion of proximal bending section 1404 is configured to remain concentrically disposed within the lumen of catheter 12 in general alignment with bending section 1203 of catheter 12, as indicated by the broken line in FIG. 18.

Reference is now made to FIGS. 17 and 18. Polymer 1416 at exposed bending section 1403 (in FIG. 5) has a durometer of between 20 D and 35 D (e.g., 25 D) which provides a degree of softness at exposed bending section 1403 that facilitates bending of section 1403. Additionally, proximal bending section 1404 has a durometer of between 25 D and 45 D (e.g., 35 D) which provides a degree of softness at exposed bending section 1404 that facilitates bending of second 1404. It is to be noted that the durometer of proximal bending section 1404 is higher than the durometer of exposed bending section 1403. Since the durometer of proximal bending section 1404 of catheter 14 is generally similar to the durometer of bending section 1203 of catheter 12, the steering of the distal end portion of catheter 14 (and of exposed distal end portion 114) and the bending of bending section 1405 of catheter 14 (especially the bending of exposed bending section 1403) does not substantially influence the bending and spatial orientation of bending section 1203 at the distal end portion of catheter 12 when catheter 14 is disposed within catheter 12.

Typically, bending section 1405 has a maximum bending angle between 100 and 140 degrees (e.g., 117 degrees). That is, bending section 1405 can bend between 0 and 140 degrees. For some applications, at least a portion of bending section 1405 has a pre-shaped angle of between 40 and 55 degrees (e.g., 45 degrees) so as to reduce force applied to bending section 1405 of catheter 14 by pull wires 31*a* and 31*b*.

Reference is again made to FIG. 17. It is to be noted that only tubular polymer 1416 and braided mesh 1417 extend proximally and distally beyond bending section 1405.

Proximally adjacent to bending section 1405 is a transition section 1406 having a length L15 of between 4 and 6 mm (e.g., 5 mm). Proximally adjacent to transition section 1406 is uniform durometer section 1407. Uniform durometer section 1407 has a durometer of between 63 D and 72 D (e.g., 72 D). Transition section 1406 has a durometer of between 35 D and 55 D (e.g., 45 D) so as to provide a transition from the relatively low durometer of proximal bending section 1404 of bending section 1405 to the relatively high durometer of uniform durometer section 1407.

FIG. 17 shows the relative position of slit engager 54 with respect to distal end 104 of catheter 14. As described hereinabove, a proximal-most end of engager 54 is disposed up to 120 mm (e.g., up to 80 mm) from distal end 104 of catheter 14.

Typically, the spatial orientation of bending section 1405 is determined by pulling on pull wires 31a and 31b that are disposed within lumens 1421 (wires 31a and 31b are not shown for clarity of illustration). Bending section 1405, for some alternative applications of the present invention, may be pre-shaped to assume a given spatial orientation and the spatial orientation of section 1405 is additionally determined by pulling on pull wires 31a and 31b.

Reference is now made to FIG. 19A, which is a schematic illustration of a catheter 1012 as described hereinabove with regard to catheter 12 with reference to FIG. 16, with the exception that catheter 1012 comprises a tubular portion 1250 that is shaped so as to define slit 52 described herein, in accordance with some applications of the present invention. Tubular portion 1250 comprises a flexible or rigid metal segment that is shaped to provide first coupling 152. For some applications, slit 52 is created in tubular portion 1250. For other applications, frame 50 (described hereinabove with reference to FIG. 13) is coupled to tubular portion 1250 in alignment with a slit generated therein.

During manufacture of catheter 1012, tubular portion 1250 is positioned longitudinally and coaxially between segments of section 1205 of catheter 1012. That is, a portion of section 1205 is cut in order to generate intermediate free ends, and tubular portion 1250 is attached at respective free ends thereof to the intermediate free ends of section 1205. For some applications, catheter 1012 is not cut, but rather catheter 1012 is comprised of two separate parts, each having free ends which are each coupled to portion 1250. For some applications, the intermediate free ends are coupled to respective metal segments, and tubular portion 1250 is coupled to the metal segments at the intermediate free ends of catheter 12 by being welded to the metal segments.

Typically, but not necessarily, the metal of portion 1250 is covered by plastic or the polymer of catheter 12, described hereinabove with reference to FIG. 16.

Typically, the pull wires of catheter 12 described hereinabove with reference to FIG. 14, run through secondary lumens in the wall of tubular portion 1250, or adjacently to the wall of portion 1250.

It is to be noted that tubular portion 1250 may be coupled to any suitable catheter known in the art.

Reference is now made to FIG. 19B, which is a schematic illustration of a catheter 1014 as described hereinabove with regard to catheter 14 with reference to FIG. 17, with the exception that catheter 1014 comprises a tubular portion 1450 that is shaped so as to define engager 54 and tab 56 described herein, in accordance with some applications of the present invention. Tubular portion 1450 comprises a flexible or rigid metal segment that is shaped to provide second coupling 154. That is, tubular portion 1450 provides slits 57 (as shown in FIG. 1) which define tab 56 and engager 54. Thus, for some applications, tubular portion 1450 and tab 56 are constructed from a single unit by creating slits in tubular portion 1450, and the protrusion of engager 54 is welded or otherwise coupled to a distal end of tab 56. For other applications, coupling 154 comprises a base which defines tab 56 and provides engager 54, and the base is coupled to tubular portion 1450.

During manufacture of catheter 1014, tubular portion 1450 is positioned longitudinally and coaxially between segments of section 1407 of catheter 1014. That is, a portion of section 1407 is cut in order to generate intermediate free ends, and tubular portion 1450 is attached at respective free ends thereof to the intermediate free ends of section 1407. For some applications, catheter 1014 is not cut, but rather catheter 1014 is comprised of two separate parts, each having free ends which are each coupled to section 1250. For some applications, the intermediate free ends are coupled to respective metal segments, and tubular portion 1450 is coupled to the metal segments at the intermediate free ends of catheter 14 by being welded to the metal segments.

Typically, but not necessarily, the metal of portion 1450 is covered by plastic or the polymer of catheter 14, described hereinabove with reference to FIG. 17.

Typically, the pull wires of catheter 14 described hereinabove with reference to FIG. 14, run through secondary lumens in the wall of tubular portion 1450, or adjacently to the wall of portion 1450.

It is to be noted that tubular portion 1450 may be coupled to any suitable catheter known in the art.

Reference is now made to FIGS. 20A-I, which are schematic illustrations of a procedure for implanting an annuloplasty ring structure 222 to repair a mitral valve 230, in accordance with an application of the present invention. This procedure is one exemplary procedure that can be performed using system 10.

Annuloplasty ring structure 222 is used to repair a dilated valve annulus of an atrioventricular valve, such as mitral valve 230. For some applications, the annuloplasty ring is configured to be placed only partially around the valve annulus (e.g., to assume a C-shape), and, once anchored in place, to be contracted so as to circumferentially tighten the valve annulus. The annuloplasty ring comprises flexible sleeve 26 and a plurality of anchors 32. Anchor deployment manipulator 61 is advanced into a lumen of sleeve 26, and, from within the lumen, deploys the anchors through a wall of the sleeve and into cardiac tissue, thereby anchoring the sleeve around a portion of the valve annulus. For some application, annuloplasty ring structure 222 is implemented using techniques described in U.S. application Ser. No. 12/437,103, filed May 7, 2009 which published as US 2010/0286767, and/or U.S. application Ser. No. 12/689,635, filed Jan. 19, 2010 which published as US 2010/0280604, both of which are assigned to the assignee of the present application and are incorporated herein by reference. As described hereinabove, annuloplasty ring structure 222 comprises adjustment mechanism 40. The adjustment mechanism comprises a rotatable structure, such as a spool, arranged such that rotation of the rotatable structure contracts the implant structure. The implant further comprises a longitudinal member, such as a wire, which is coupled to the adjustment mechanism. A rotation tool is provided for rotating the rotatable structure. The tool is configured to be guided along (e.g., over, alongside, or through) the longitudinal member, to engage the rotatable structure, and to rotate the rotatable structure in response to a rotational force applied to the tool.

Figure 20A:
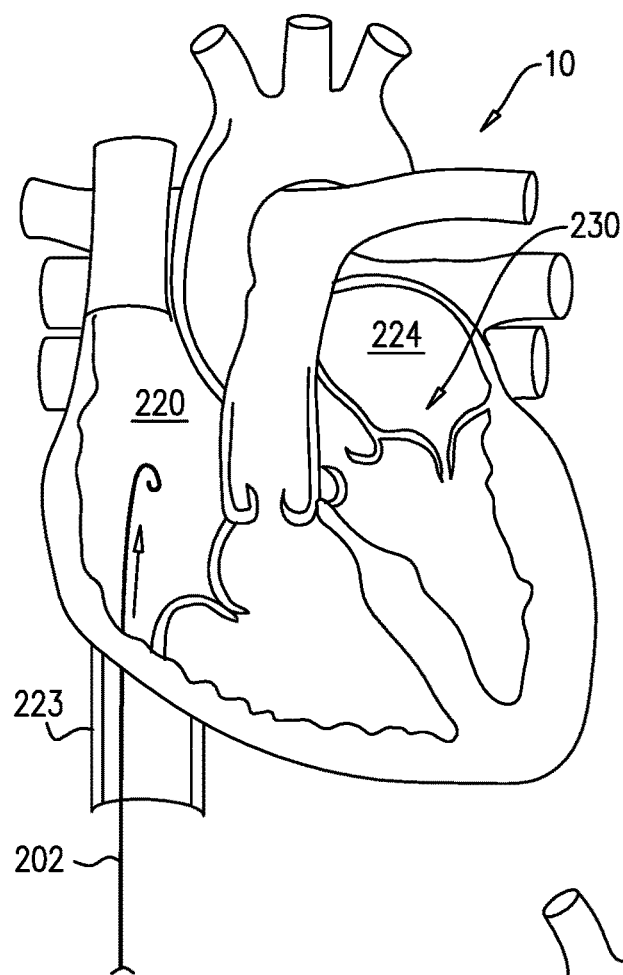

As shown in FIG. 20A, the procedure typically begins by advancing a semi-rigid guidewire 202 into a right atrium 220 of the patient. The procedure is typically performed with the aid of imaging, such as fluoroscopy, transesophageal echo, and/or echocardiography.

Figure 20B:
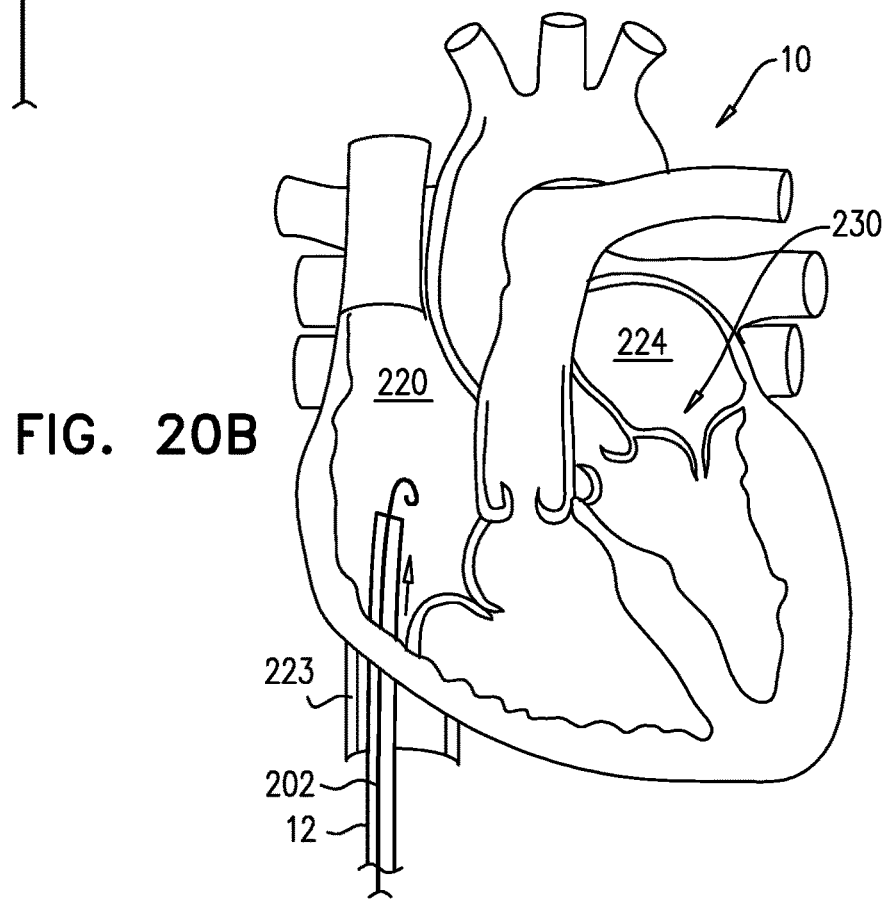

As show in FIG. 20B, guidewire 202 provides a guide for the subsequent advancement of outer catheter 12 therealong and into the right atrium. Once a distal portion of catheter 12 has entered the right atrium, guidewire 202 is retracted from the patient's body. Catheter 12 typically comprises a 14-24 F sheath, although the size may be selected as appropriate for a given patient. Catheter 12 is advanced through vasculature into the right atrium using a suitable point of origin typically determined for a given patient. For example:

catheter 12 may be introduced into the femoral vein of the patient, through an inferior vena cava 223, into right atrium 220, and into a left atrium 224 trans septally, typically through the fossa ovalis;

catheter 12 may be introduced into the basilic vein, through the subclavian vein to the superior vena cava, into right atrium 220, and into left atrium 224 trans septally, typically through the fossa ovalis; or catheter 12 may be introduced into the external jugular vein, through the subclavian vein to the superior vena cava, into right atrium 220, and into left atrium 224 trans septally, typically through the fossa ovalis.

For some applications of the present invention, catheter 12 is advanced through inferior vena cava 223 of the patient (as shown) and into right atrium 220 using a suitable point of origin typically determined for a given patient.

Figure 20C:
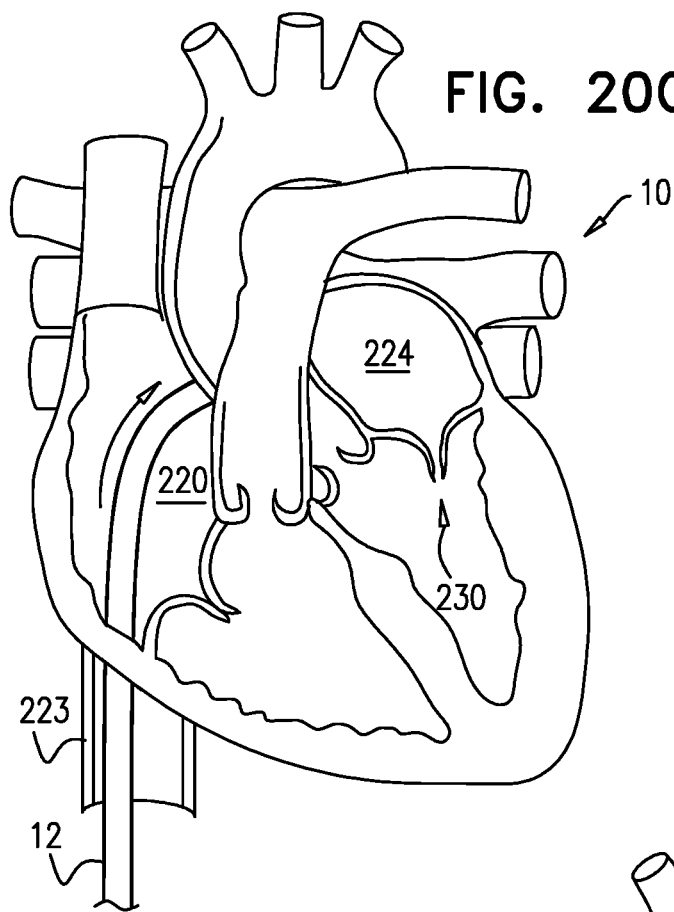

Catheter 12 is advanced distally until the sheath reaches the interatrial septum, and guidewire 202 is withdrawn, as shown in FIG. 20C.

Figure 20D:
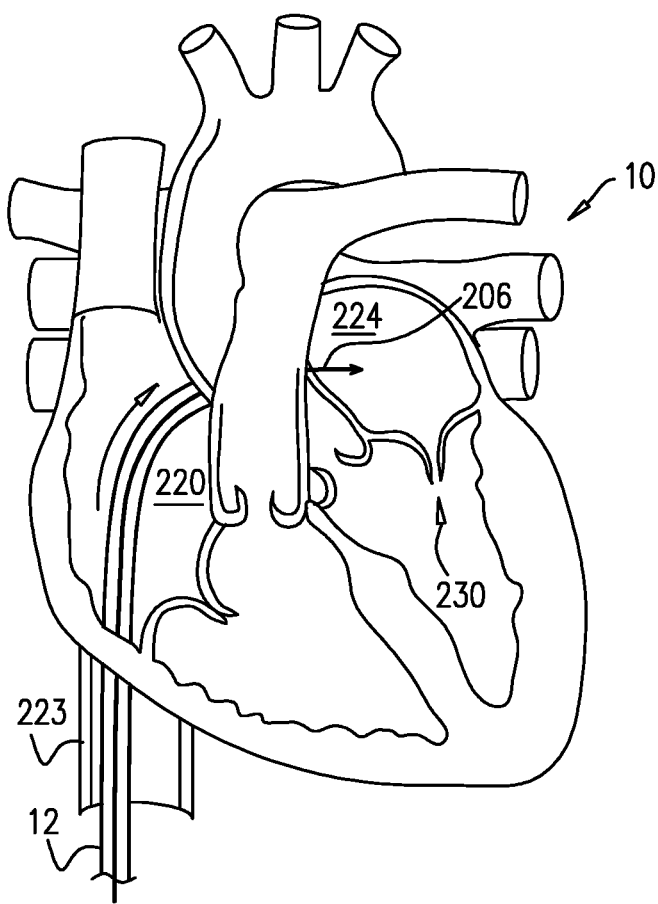

As shown in FIG. 20D, a resilient needle 206 and a dilator (not shown) are advanced through catheter 12 and into the heart. In order to advance catheter 12 transseptally into left atrium 224, the dilator is advanced to the septum, and needle 206 is pushed from within the dilator and is allowed to puncture the septum to create an opening that facilitates passage of the dilator and subsequently catheter 12 therethrough and into left atrium 224. The dilator is passed through the hole in the septum created by the needle. Typically, the dilator is shaped to define a hollow shaft for passage along needle 206, and the hollow shaft is shaped to define a tapered distal end. This tapered distal end is first advanced through the hole created by needle 206. The hole is enlarged when the gradually increasing diameter of the distal end of the dilator is pushed through the hole in the septum. As shown in FIG. 16, for example, a distal-most end 102 of catheter 12 is tapered so as to facilitate passage of the distal portion of catheter 12 through the opening in the septum.

Figure 20E:
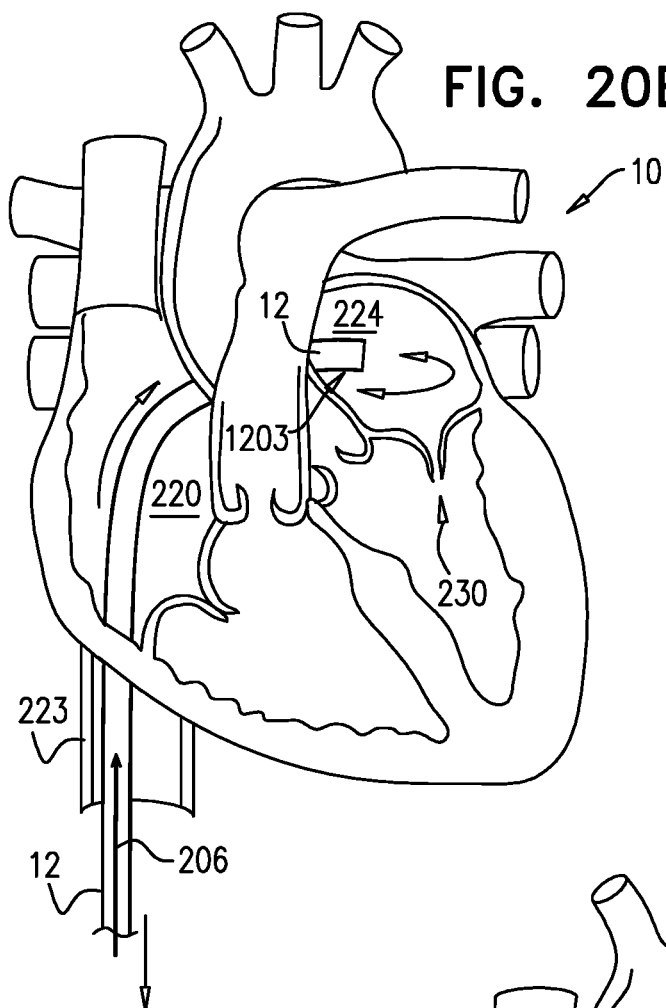

The advancement of catheter 12 through the septum and into the left atrium is followed by the extraction of the dilator and needle 206 from within catheter 12, as shown in FIG. 20E. Once the distal portion of catheter 12 is disposed within atrium 224, the steerable distal end portion of catheter 12 (which includes at least a portion of bending section 1203, as described hereinabove with reference to FIGS. 16 and 18) is steered in a first plane that is parallel to a plane of the annulus of mitral valve 230. Such steering moves the distal end portion of catheter 12 in a direction from the interatrial septum toward surrounding walls of the atrium, as indicated by the arrow in atrium 224. As described hereinabove, steering of the distal portion of catheter 12 is performed via steering knob 210 of handle 22 in handle portion 101 (in FIGS. 13 and 14).

Figure 20F:
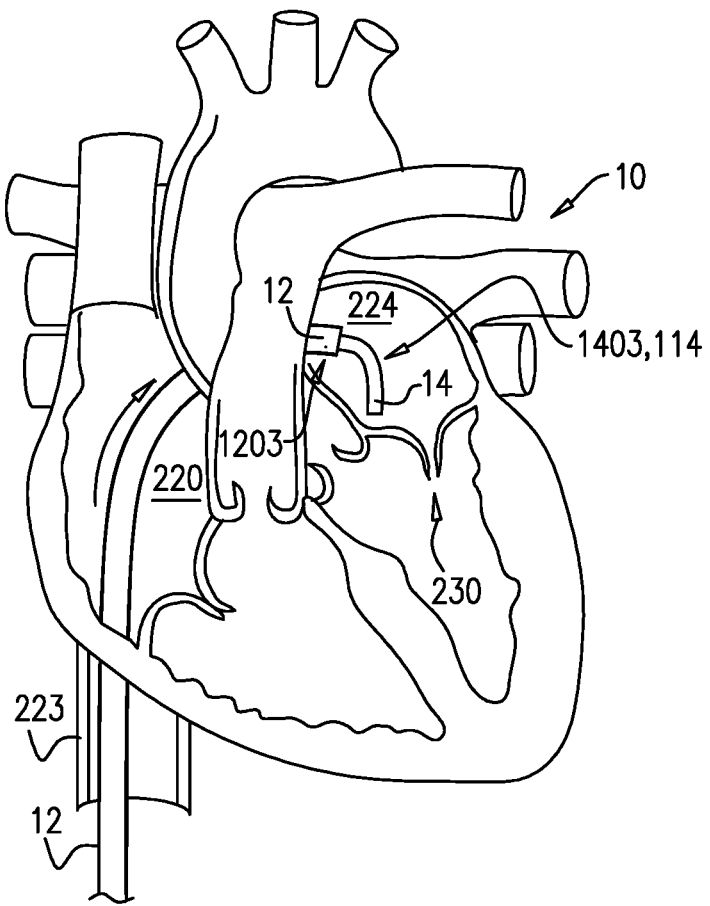

As shown in FIG. 20F, annuloplasty ring structure 222 (not shown for clarity of illustration, with anchor deployment manipulator 61 therein) is advanced through guide catheter 14, which is in turn, advanced through catheter 12 into left atrium 224. As shown in FIG. 20F, exposed distal end portion 114 of catheter 14 extends beyond distal end 102 of catheter 12. Exposed distal end portion 114 is then (1) steered toward the annulus of valve 230 along a plane that is perpendicular with respect to the steering plane of catheter 12 and that is perpendicular with respect to valve 230, and is (2) bent, via bending section 1403 (as described hereinabove with reference to FIGS. 17 and 18) toward valve 230. As described hereinabove, steering of the distal portion of catheter 14 is performed via steering knob 214 of handle 24 in handle portion 101 (in FIGS. 13 and 14).

As shown in FIG. 20G, a distal end 251 of sleeve 26 is positioned in a vicinity of a left fibrous trigone 242 of an annulus 240 of mitral valve 230. (It is noted that for clarity of illustration, distal end 251 of sleeve 26 is shown schematically in the cross-sectional view of the heart, although left trigone 242 is in reality not located in the shown cross-sectional plane, but rather out of the page closer to the viewer.) Alternatively, the distal end of sleeve 26 is positioned in a vicinity of a right fibrous trigone 244 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Once positioned at the desired site near the selected trigone, deployment manipulator 61 deploys a first anchor 32 through the wall of sleeve 26 (by penetrating the wall of the sleeve in a direction in a direction parallel to a central longitudinal of deployment manipulator 61, or anchor driver 36, through the distal end of channel 18, and/or parallel to central longitudinal axis of tissue coupling element 60 of anchor 32) into cardiac tissue near the trigone. Following the deployment of anchor 32 in the cardiac tissue, deployment element 38 is decoupled from anchor 32 by moving rod 130 proximally.

Anchors 32 are typically deployed from a distal end of manipulator 61 while the distal end is positioned such that a central longitudinal axis through the distal end of manipulator 61 forms an angle with a surface of the cardiac tissue of between about 20 and 90 degrees, e.g., between 45 and 90 degrees, such as between about 75 and 90 degrees, such as about 90 degrees. Typically, anchors 32 are deployed from the distal end of manipulator 61 into the cardiac tissue in a direction parallel to the central longitudinal axis through the distal end of manipulator 61. Such an angle is typically provided and/or maintained by channel 18 being more rigid than sleeve 26. Distal end 17 (shown in FIG. 2) of channel 18 is typically brought close to the surface of the cardiac tissue (and the wall of sleeve 26 that is disposed against the surface of the cardiac tissue), such that little of each anchor 32 is exposed from channel 18 before penetrating the sleeve and the tissue. For example, distal end 17 of channel 18 may be placed (e.g., pushed) against the wall of the sleeve, sandwiching the sleeve against the cardiac tissue.

Reference is now made to FIGS. 14 and 20G. As shown on the right side of FIG. 14, channel 18 is a tube which has an opening 1118 at distal end 17 of channel 18. As shown in 20G, during the sandwiching, channel 18 sandwiches a portion of the wall of the sleeve between the opening (not shown in FIG. 20G for clarity of illustration) in channel 18 and a region of cardiac tissue. During the sandwiching, anchor 32 is deployed.

For some applications, this placement of distal end 17 of channel 18 against the cardiac tissue (via the wall of the sleeve), stabilizes the distal end during deployment and anchoring of each anchor 32, and thereby facilitates anchoring. For some applications, pushing of distal end 17 against the cardiac tissue (via the wall of the sleeve) temporarily deforms the cardiac tissue at the site of contact. This deformation may facilitate identification of the site of contact using imaging techniques (e.g., by identifying a deformation in the border between cardiac tissue and blood), and thereby may facilitate correct positioning of the anchor.

For some applications of the present invention, anchors 32 may be deployed from a lateral portion of manipulator 61.

Reference is now made to FIGS. 20G and 1B. It is to be noted that mechanism 40 shown in FIG. 1B is coupled to sleeve 26 using connectors 27.

Figure 20H:
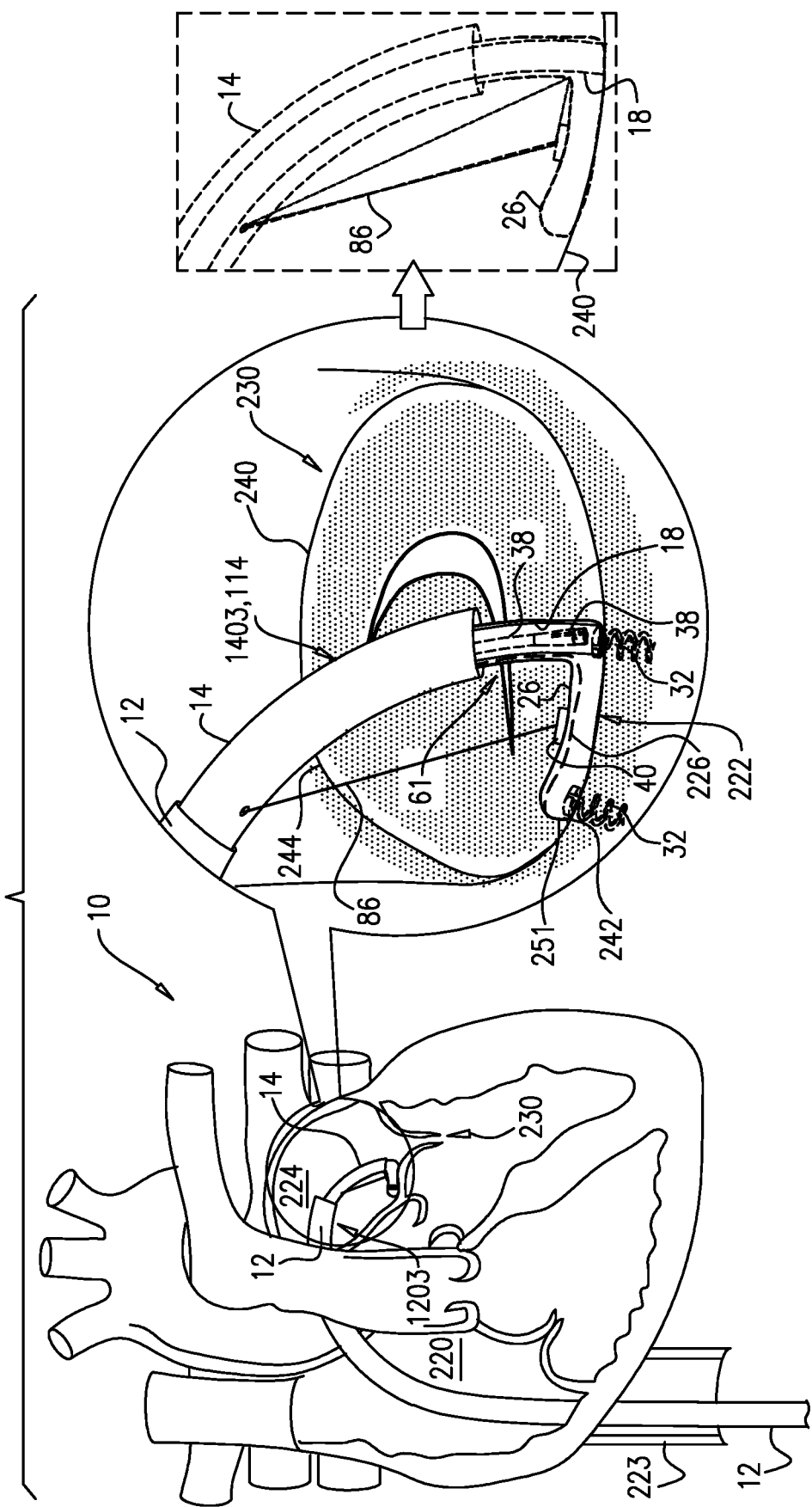

Reference is now made to FIGS. 20G and 14. Following the deployment of the first anchor, a distal portion of sleeve 26 is decoupled from a portion of implant-decoupling channel 18. In order to decouple the portion of sleeve 26 from outer surface of channel 18, (1) channel 18 is pulled proximally, while (2) reference-force tube 19 is maintained in place in a manner in which a distal end of tube 19 provides a reference force to sleeve 26 in order to facilitate retraction freeing of a successive portion of sleeve 26 from around channel 18. In order to decouple sleeve 26 from the outer surface of channel 18, (1) channel 18 is pulled proximally, while (2) reference-force tube 19 is maintained in place. An indicator 2120 (shown herein with reference to FIGS. 30A-B) on handle 126 provides an indication of how much channel 18 is withdrawn from within sleeve 26 (i.e., how much the delivery tool is decoupled from sleeve 26, and how much the sleeve has advanced off channel 18 and against tissue). A proximal end of channel 18 is coupled to a knob 94 (FIG. 14) which adjusts an axial position of channel 18 proximally and distally with respect to reference-force tube 19 and sleeve 26. As shown in FIG. 20H, deployment manipulator 61 is repositioned along annulus 240 to another site selected for deployment of a second anchor 32. Reference is now made to FIGS. 13 and 20H. Such repositioning of manipulator 61 is accomplished by:

1. the steering of the distal end portion of catheter 12 (e.g., by steering knob 210 of handle 22) in the first plane that is parallel with respect to annulus 240 of valve 230 to a desired spatial orientation and in a manner which bends bending section 1203 of catheter 12, 2. the steering of the distal end portion of portion of catheter 14 (e.g., by steering knob 214 of handle 24) in the second plane that is perpendicular with respect to annulus 240 of valve 230 to a desired spatial orientation, and in a manner which bends bending section 1405 of catheter 14 (specifically bending section 1403), 3. by axially moving catheter 14 with respect to catheter 12 via knob 216, 4. by axially moving the stand supporting handles 22 and 24 to move both catheters 12 and 14, 5. by moving tube 19 and sleeve 26 axially by sliding mount 93 along track 90 via knob 95, and/or 6. by moving channel 18 relative to tube 19 by actuating knob 94.

Typically, the first anchor is deployed most distally in the sleeve (generally at or within a few millimeters of the distal tip of the sleeve), and each subsequent anchor is deployed more proximally, such that the sleeve is gradually decoupled from channel 18 of deployment manipulator 61 in a distal direction during the anchoring procedure (i.e., channel 18 is withdrawn from within sleeve 26, and handle 126 is moved distally so as to retract the tool to make the successive proximal portion sleeve 26 ready for implantation of a subsequent anchor). The already-deployed first anchor 32 holds the anchored end of sleeve 26 in place, so that the sleeve is drawn from the site of the first anchor towards the site of the second anchor. Typically, as sleeve 26 is decoupled from channel 18, deployment manipulator 61 is moved generally laterally along the cardiac tissue, as shown in FIG. 20H. Deployment manipulator 61 deploys the second anchor through the wall of sleeve 26 into cardiac tissue at the second site. Depending on the tension applied between the first and second anchor sites, the portion of sleeve 26 therebetween may remain tubular in shape, or may become flattened, which may help reduce any interference of the ring with blood flow.

As shown in the enlarged in-phantom image to the right, during repositioning of manipulator 61, a generally-triangular shape is formed between: (1) guide member 86, (2) a distal portion of sleeve 26, and (3) channel 18 surrounded partially by catheter 14. It is to be noted that the illustrated triangle is shown in phantom to indicate the relative triangular orientation of the three components, and that the illustrated triangle is not a part of the apparatus shown.

Figure 20I:
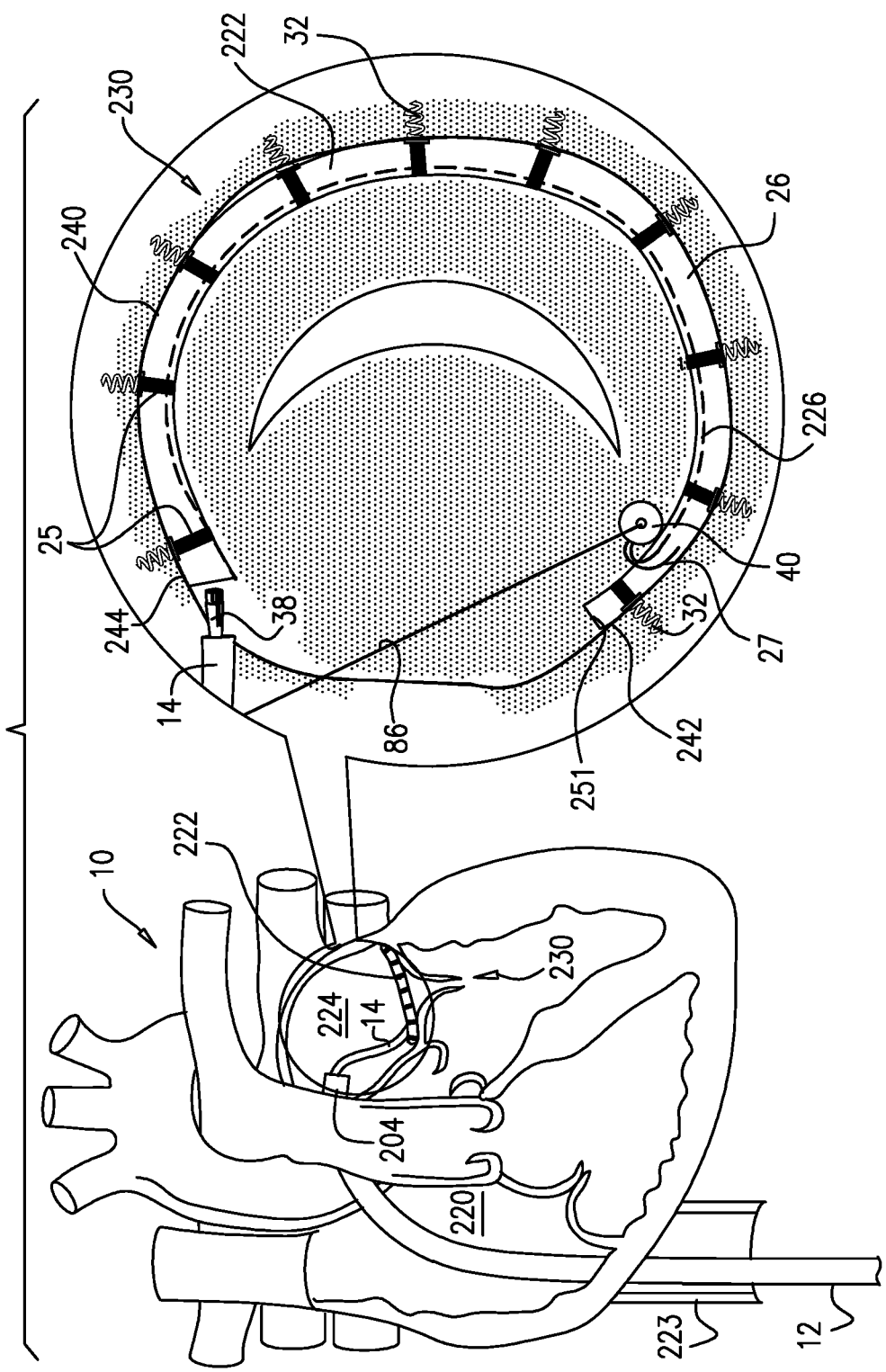

As shown in FIG. 20I, deployment manipulator 61 is repositioned along the annulus to additional sites, at which respective anchors are deployed, until the last anchor is deployed in a vicinity of right fibrous trigone 244 (or left fibrous trigone 242 if the anchoring began at the right trigone). Alternatively, the last anchor is not deployed in the vicinity of a trigone, but is instead deployed elsewhere in a vicinity of the mitral valve, such as in a vicinity of the anterior or posterior commissure. Then, system 10 is removed, leaving behind guide member 86. A rotation tool is then threaded over and advanced along guide member 86 toward adjustment mechanism 40, and is used to rotate the spool of adjustment mechanism 40 in order to tighten structure 222 by adjusting a degree of tension of contracting member 226 (not shown in FIG. 20I, but shown in FIG. 5B). Once the desired level of adjustment of structure 222 is achieved (e.g., by monitoring the extent of regurgitation of the valve under echocardiographic and/or fluoroscopic guidance), the rotation tool and guide member 86 are removed from the heart. For some applications, a distal portion of guide member 86 may be left within the heart of the patient and the proximal end may be accessible outside the body, e.g., using a port. For such applications, adjustment mechanism 40 may be accessed at a later stage following initial implantation and adjustment of ring structure 222.

As shown, sleeve 26 of ring structure 222 comprises a plurality of radiopaque markers 25, which are positioned along the sleeve at respective longitudinal sites to indicate anchor-designated target areas. The markers may provide an indication in a radiographic image (such as a fluoroscopy image) of how much of sleeve 26 has been deployed at any given point during an implantation procedure, in order to enable setting a desired distance between anchors 32 along the sleeve 26.

Alternatively, annuloplasty ring structure 222 is implanted by right or left thoracotomy, mutatis mutandis.

As shown, mechanism 40 is coupled typically coupled to sleeve 26 via one or more connectors 27, such as sutures, which provide flexible and/or articulated coupling. A proximal end of connector 27 is disposed proximally to mechanism 40 (e.g., by being fixed to a portion of sleeve 26 proximal to mechanism 40 or by being accessible outside the body of the patient). A distal end of connector 27 is coupled (e.g., by being fixedly coupled by a knot or other mechanical coupling) to mechanism 40. Guide member 86, described hereinabove, typically extends distally from catheter 14, between end 251 of sleeve 26 and adjustment mechanism 40, and there is coupled to the adjustment mechanism. For some applications it is advantageous to (1) advance the structure to the mitral valve while mechanism 40 is disposed on the longitudinal axis of sleeve 26 (e.g., collinearly with the sleeve), so as to maintain a small cross-sectional diameter of the structure for transluminal delivery; and (2) to subsequently move mechanism 40 away from the longitudinal axis, e.g., so as to allow the distal end wall of sleeve 26 to be placed against the annulus, and/or so as to allow an anchor to be driven through the end wall of the sleeve. Connectors 27 facilitate this technique by making mechanism 40 flexibly and/or articulatably coupled to sleeve 26. For some applications, connectors 27 are tensioned or relaxed to move mechanism 40 with respect to sleeve 26 to reposition mechanism 40. For some applications, guide member 86 is tensioned or relaxed in order to reposition mechanism 40. For some applications, connectors 27 comprise a hinge.

For some applications of the present invention, following implantation of sleeve 26 along the annulus, an excess portion of sleeve 26 may be present at the proximal portion of sleeve. In such applications, following removal of manipulator 61, a cutting tool (not shown) may be advanced within channel 18 and into the lumen of the excess portions of sleeve 26 (e.g., from within sleeve 26) in order to cut the sleeve proximal to the proximal-most-deployed anchor 32.

Reference is now made to FIGS. 6A-I and 20A-I. It is to be noted that techniques for implantation of structure 222 shown in FIGS. 20A-I may be employed in techniques for implantation of ring 3022, as described herein with respect to FIGS. 6A-I. For example, ring 3022 may comprise guide member 86, as shown in FIGS. 20G-I.

Figure 21:
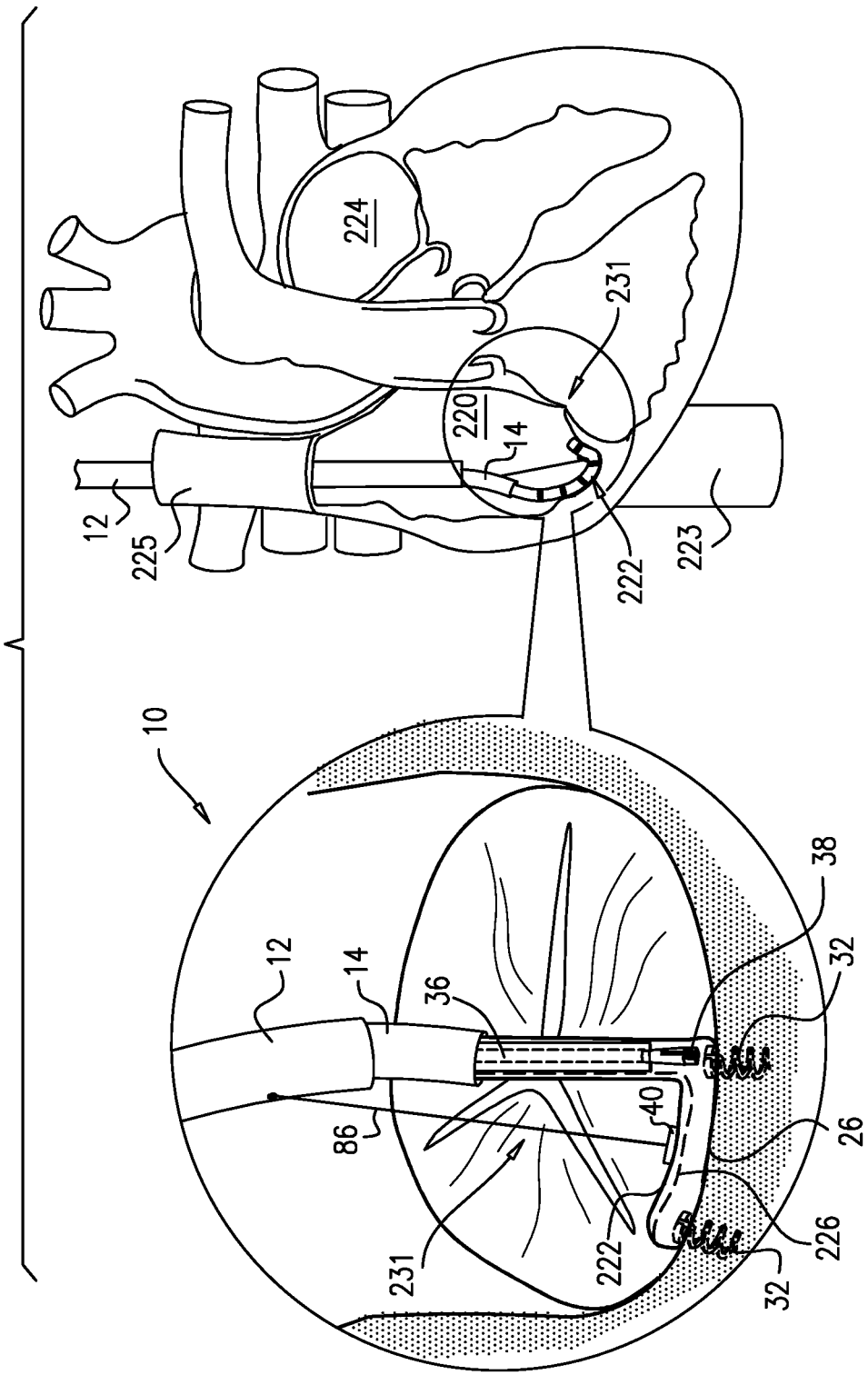
FIG. 21 is a schematic illustration of a procedure for implanting an annuloplasty ring structure to repair a tricuspid valve, in accordance with some applications of the present invention.

Reference is made to FIG. 21. For some applications of the present invention, annuloplasty ring structure 222 is used to treat an atrioventricular valve other than the mitral valve, i.e., tricuspid valve 231, using system 10 in a similar method as described hereinabove with reference to FIGS. 20A-I, in accordance with some applications of the present invention.

For these applications, ring structure 222 and other components of system 10 described hereinabove as being placed in the left atrium are instead placed in the right atrium 220. FIG. 21 shows accessing right atrium 220 through superior vena cava 225 by way of illustration and not limitation. Components of system 10 may be advanced into the right atrium through inferior vena cava 223.

Reference is now made to FIGS. 22A-D, which are schematic illustrations of an indicator and locking system 1700 comprising (1) a protrusion 1724 coupled to guide-catheter handle 24, and (2) a housing 1702, or cradle, shaped to define a groove 1704 configured to receive protrusion 1724, in accordance with some applications of the present invention. System 1700 is configured to provide an indication, at a proximal location outside the body of the patient, of the state of coupling of first and second couplings 152 and 154 of outer catheter 12 and guide catheter 14, respectively (i.e., when engager 54 is received within slit 52 at the distal end portions of catheters 14 and 12, respectively). Additionally, system 1700 is configured to rotationally lock catheter 12 to catheter 14, as is described hereinbelow.

Housing 1702 comprises a handle portion that is coupled to a proximal end of catheter 12. As shown, groove 1704 is shaped so as to define a curved groove along a lateral portion of housing 1702. Groove 1704 extends between 45 and 135 rotational degrees, e.g., 90 degrees, as shown.

As described hereinabove with reference to FIGS. 13-14, proximal handle portion 101 is supported by a stand having support legs 91 (i.e., first leg 91a and second leg 91b, as shown in FIGS. 22A-D). As shown in FIGS. 22A-D, first leg 91a (which is configured to receive guide-catheter handle 24) provides housing 1702. As described hereinabove, guide catheter 14 is first advanced within the lumen of outer catheter 12 when the physician places the distal end of catheter 14 within the lumen of catheter 12 (via outer-catheter handle 22) and advances handle 24 (coupled to the proximal end of catheter 14) toward handle 22, as indicated by the arrow in FIG. 22A. As described hereinabove with reference to FIGS. 15A-B, since the lumen of catheter 12 is free from any protrusions or recessed portions, and since engager 54 is depressible by tab 56, catheter 14 is configured to enter the lumen of catheter 12 in any rotational configuration thereof. As handle 24 is advanced toward handle 22, protrusion 1724 of handle 24 advances toward groove 1704. Groove 1704 is shaped to provide a protrusion-access location 1706 and a protrusion-locking location 1708, which locations are typically but not necessarily spaced 90 degrees apart. Protrusion-locking location 1708 is shaped to provide a depressible locking element 1710 which comprises a depressible pin to lock protrusion 1724 in place, as is described hereinbelow.

Figure 22A:
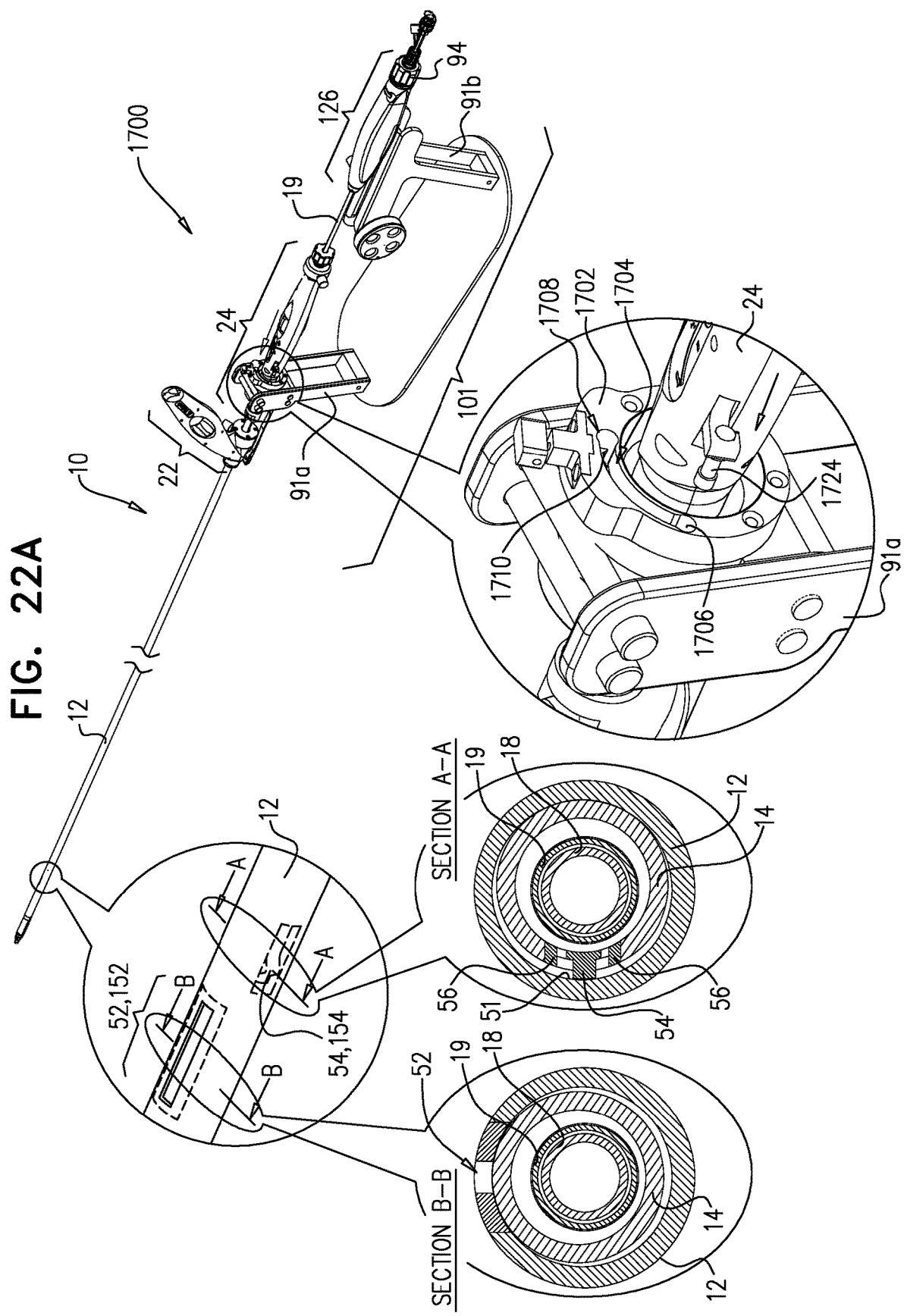
Figure 22B:
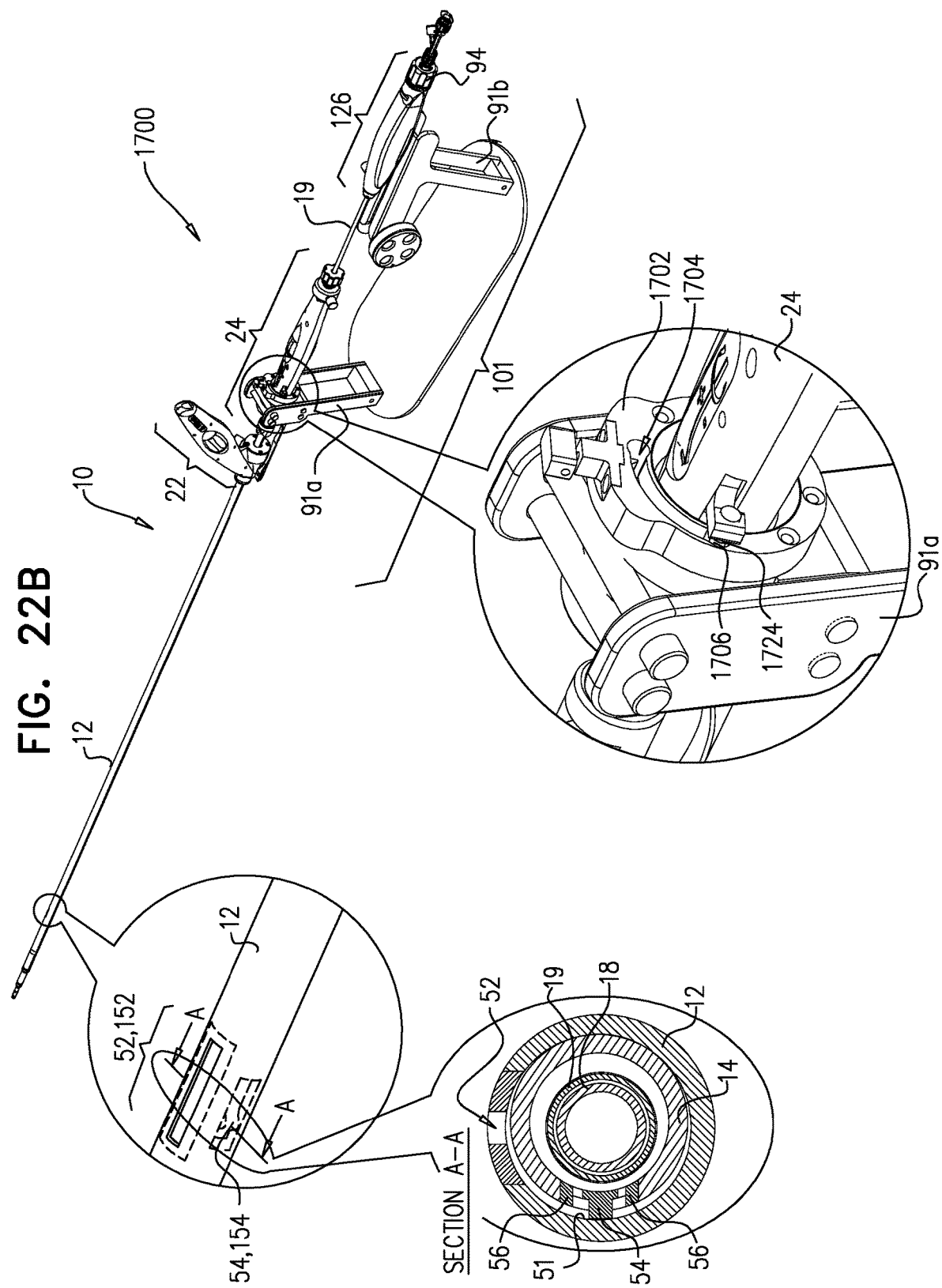

As shown in FIG. 22B, when handle 24 has been pushed distally toward handle 22, protrusion 1724 advances toward groove 1704 in order to engage protrusion-access location 1706 thereof. Depending on the rotational orientation of handle 24 with respect to handle 22, the physician may need to rotate handle 24 to bring protrusion 1724 in alignment with protrusion-access location 1706 of groove 1704. Once protrusion 1724 is in alignment with protrusion-access location 1706, handle 24 is further pushed distally in order to engage protrusion 1724 with protrusion-access location 1706 of groove 1704. Once protrusion 1724 is located within protrusion-access location 1706 of groove 1704, engager 54 is disposed in proximity with (e.g., in a distal location in the vicinity of) slit 52. As shown in the enlarged image at the distal end portion of system 10 and in section A-A, when protrusion 1724 is located within protrusion-access location 1706 of groove 1704, engager 54 of catheter 14 is rotationally offset with respect to slit 52 of catheter 12 by 90 degrees, by way of illustration and not limitation (i.e., the degrees between protrusion-access location 1706 and protrusion-locking location 1708).

FIG. 22C shows rotation of catheter 14 with respect to catheter 12, in response to rotation of handle 24 in the direction indicated by the arrow. As handle 24 is rotated, protrusion 1724 slides within groove 1704 toward protrusion-locking location 1708, as shown in the enlarged image of a portion of handle 24. As shown in the enlarged section of the distal end portion of system 10 and in section A-A, as protrusion 1724 is being advanced toward protrusion-locking location 1708, engager 54 is closer to slit 52 and is rotationally offset with respect to slit 52 by fewer degrees than when protrusion 1724 is located at protrusion-access location 1706.

Figure 22D:
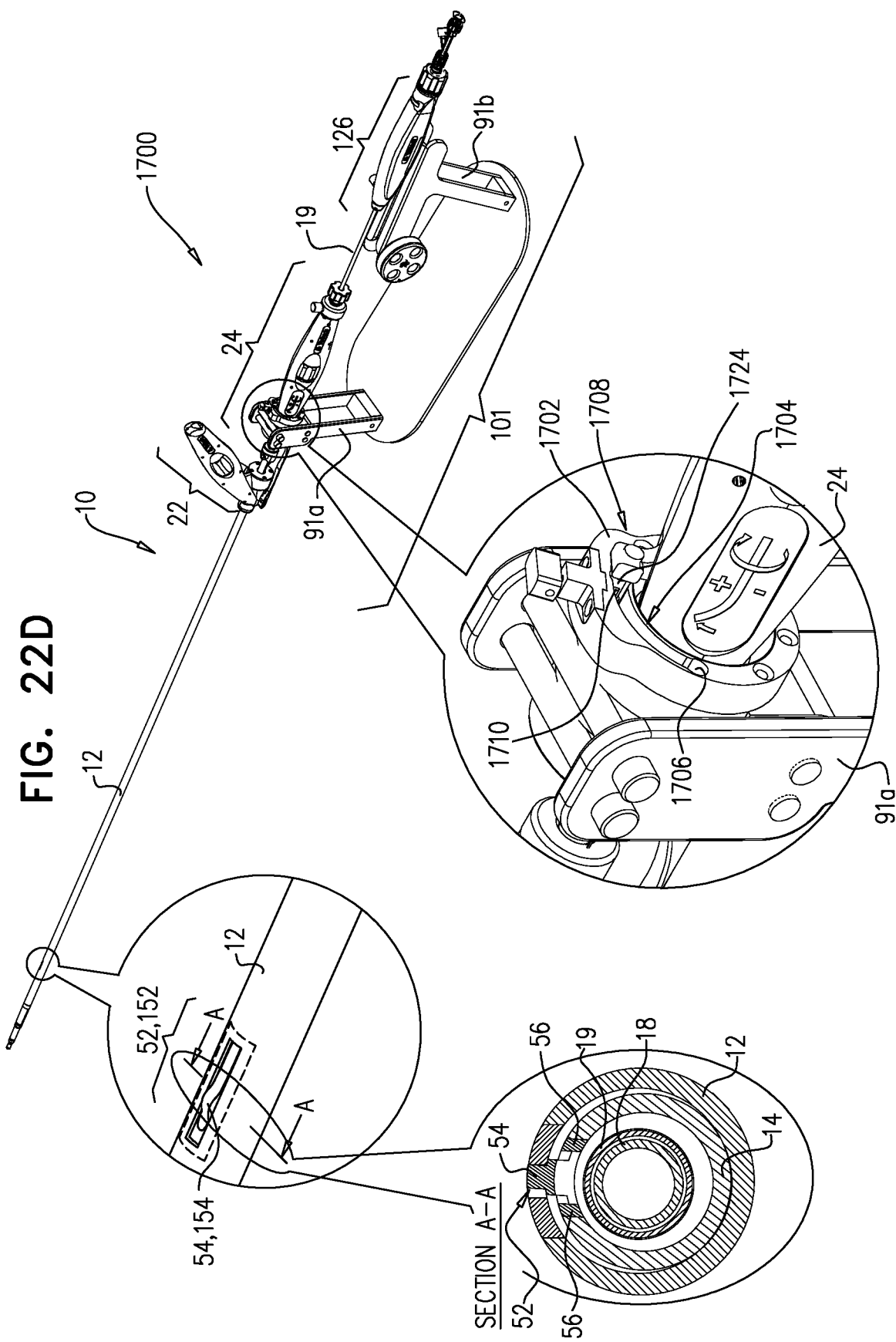

FIG. 22D shows system 1700 following the rotation of handle 24 to position protrusion 1724 within protrusion-locking location 1708, in order to rotationally lock catheter 12 to catheter 14 in addition to the rotational locking of catheters 12 and 14 provided by insertion of engager 54 within slit 52, as shown the enlarged section of the distal end portion of system 10 and in section A-A. As protrusion 1724 advances toward location 1708, protrusion 1724 pushes locking element 1710. For some applications, locking element 1710 is spring-loaded, and is configured to return to a resting state (as shown in FIG. 22D) in the absence of force applied thereto. Thus, once protrusion 1724 has advanced beyond locking element 1710 into protrusion-locking location 1708, element 1710 returns to its resting state to prevent protrusion from returning toward protrusion-access location 1706. That is, locking element 1710 is only depressible when protrusion 1724 is advanced from protrusion-access location 1706 toward protrusion-locking location 1708. In such a manner, groove 1704, protrusion 1724, and locking element 1710 of system 1700 rotationally lock catheters 12 and 14 and also prevents accidental movement of handle 24 with respect to handle 22.

Typically, when protrusion 1724 couples to housing 1702 (e.g., when protrusion 1724 locks into protrusion-locking location 1708), coupling 154 simultaneously couples to coupling 152.

Reference is now made to FIGS. 13, 15A-E, and 22A-D. For some applications, two pairs of couplings are thereby provided: (pair 1) couplings 152 and 154 at a distal portion of catheters 12 and 14, respectively, and (pair 2) housing 1702 and protrusion 1724 at a proximal portion of the catheters. It should be noted that, whereas couplings 152 and 154 typically facilitate some longitudinal sliding of the distal end of catheter 14 with respect to the distal end of catheter 12 (as described hereinabove), housing 1702 and protrusion 1724 typically inhibit (e.g., prevent) longitudinal movement of the proximal end of catheter 14 with respect to the proximal end of catheter 12.

Figure 23A:
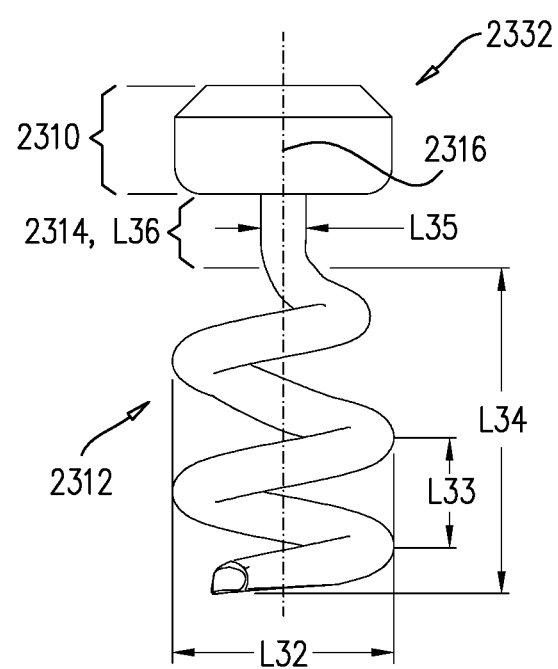
Figure 23B:
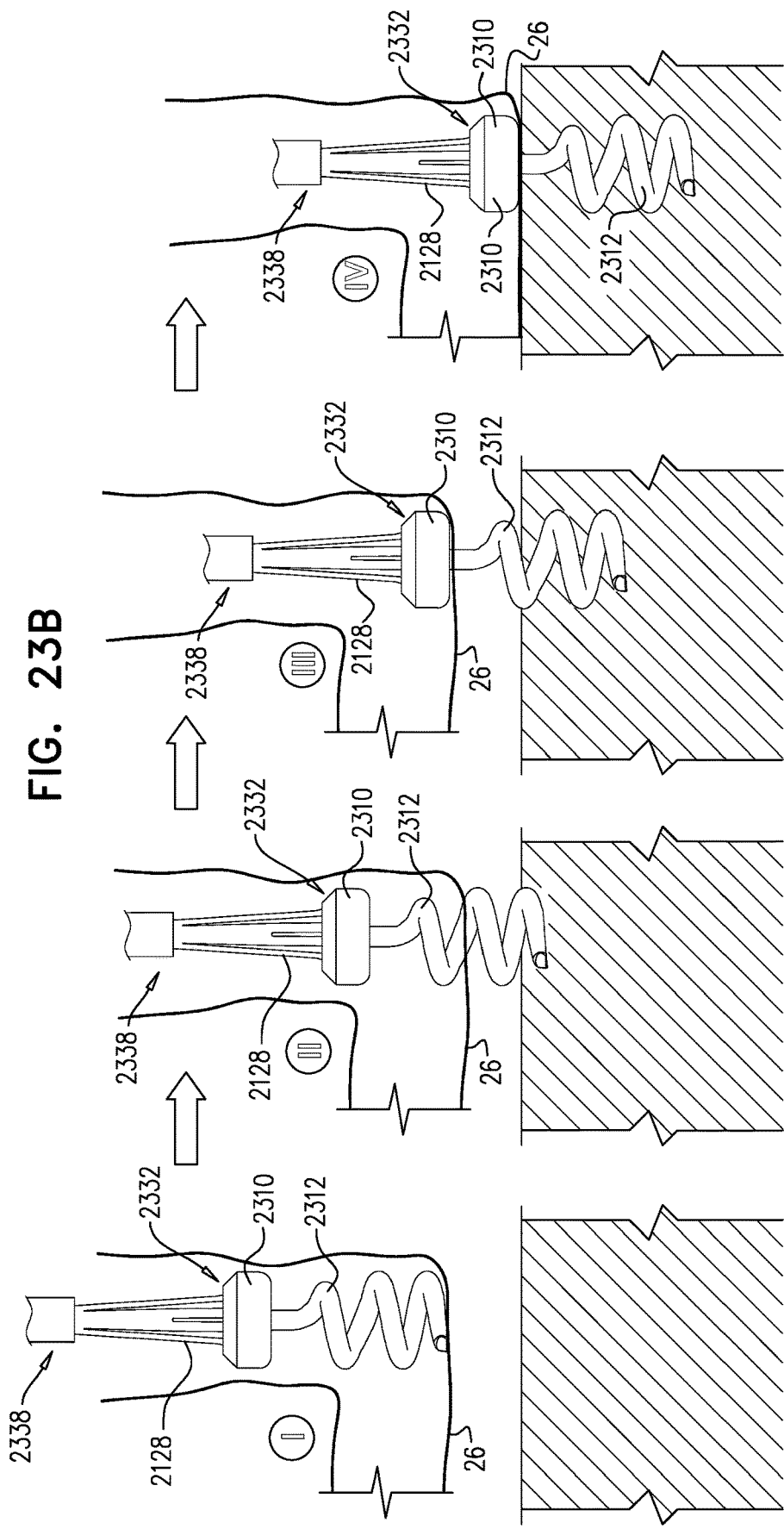

Reference is made to FIGS. 23A-C, which are schematic illustrations of a tissue anchor 2332 configured for anchoring sleeve 26 described hereinabove, in accordance with some applications of the present invention. Anchor 2332 has a coupling head 2310 configured to be coupled to a deployment element 2338, which has a locking mechanism 2128 disposed at a distal end thereof. Typically, deployment element 2338 and locking mechanism 2128 respectively comprise deployment element 38 and locking mechanism 128, described hereinabove. For some applications, coupling head 2310 is alternatively or additionally configured to be coupled to, and/or used with, deployment manipulator 61, deployment element 38, anchor driver 36, and/or anchor-manipulation tool 1802 described hereinabove. Anchor 2332 provides a tissue coupling element 2312 (e.g., a helical tissue coupling element, as shown, or a screw). For some applications of the invention, anchor 32 described hereinabove, comprises anchor 2332 and/or anchors 32 and 2332 are interchangeable.

A proximal portion of coupling element 2312 comprises a vertical (and typically straight) proximal portion 2314 which is coupled to coupling head 2310 within 3 mm of a central longitudinal axis 2316 of tissue anchor 2332 (e.g., within 1 mm of axis 2316, such as on axis 2316). Proximal portion 2314 may alternatively comprise a proximal stem portion that couples coupling element 2312 to coupling head 2310. Vertical proximal portion 2314 typically has a length L36 of 0.2-0.7 mm, and is typically more than 1.3 times as great as (e.g., between 2 and 10 times as great, such as between 2 and 4 times as great as) a thickness of the fabric of sleeve 26. During anchoring of sleeve 26 by anchor 2332 (e.g., as shown in FIG. 23B), such a configuration of the positioning of portion 2314 at the center of coupling head 2310 facilitates rotation of tissue anchor 2332 with respect to sleeve 26 in a manner that prevents twisting of sleeve 26 during rotation. That is, once coupling element 2312 has passed far enough through sleeve 26 such that portion 2314 traverses the wall of the sleeve (as shown in stage (iii) of FIG. 23B), portion 2314 rotates freely within the wall of the sleeve. (For some applications in which portion 2314 is coupled to coupling head 2310 within 3 mm of, but not on, axis 2316, flexibility of the fabric of sleeve 26 facilitates such free rotation, by distorting as portion 2314 "wiggles".) Such a configuration allows anchor 2332 to be driven into the cardiac tissue, such that coupling head 2310 draws sleeve 26 closer to the cardiac tissue, without distorting (e.g., twisting, kinking, buckling, etc.) the sleeve (as shown by the transition from stage (iii) to stage (iv) of FIG. 23B). For some such applications, anchor 2332, coupling element 2312, and/or portion 2314 act as an integral washer and/or a screw with an integral washer, as is known in the hardware art.

Coupling head 2310 may be either male (e.g., a hex or square protrusion) or female (e.g., a straight slot, a hex opening, a Phillips opening, or a Robertson opening). The use of helical anchors, which are screwed into the cardiac tissue, generally minimizes the force that needs to be applied during deployment of the anchors into the cardiac tissue. Anchor driver 36 has a deployment element 38 that is either male (e.g., comprising a screwdriver head, having, such as a slot-head, an Allen-head, a Phillips-head, a Robertson-head, or a hex-head) or female (e.g., comprising a wrench head, having, for example, a square or hex opening), as appropriate for the driving interface provided by coupling head 2310 of anchor 2332 of FIGS. 23A-C.

Anchor 2332 has an anchor helix diameter L32 of between 0.2 and 0.3 cm, e.g., 0.25 cm. That is, the radius of the anchor helix from longitudinal axis 2316 is typically between 0.1 and 0.15 cm, e.g., 0.125 cm. Anchor 2332 has an anchor helix pitch L33 of between 0.1 and 0.2 cm, e.g., 0.12 cm. Anchor 2332 has an anchor helix length L34 of between 0.3 and 0.6 cm, such as 0.3 and 0.45 cm, e.g., 0.35 cm. Anchor 2332 has a helix wire thickness L35 of between 0.02 and 0.1 cm, e.g., 0.05 cm.

For some applications of the invention, a torque-limiting apparatus is coupled to anchor driver 36 and prevents over-rotation of the anchor, penetration of tissue coupling element 2312 too deep into tissue, and/or damage to the tissue.

For some applications, a ratio between diameter L32 of the helix of anchor 2332 (cm) to torque (Ncm) is typically, but not necessarily 0.25/0.8, or 0.3125. For some applications, a ratio between pitch L33 of anchor 2332 (*cm*) to torque (Ncm) is typically, but not necessarily 0.12/0.8, or 0.15. For some applications, a ratio between length L34 of the helix of anchor 2332 (cm) to torque (Ncm) is typically, but not necessarily 0.35/0.8, or 0.4375. For some applications, a ratio between thickness L35 of the wire forming anchor 2332 (*cm*) to torque (Ncm) is typically, but not necessarily 0.05/0.8, or 0.0625.

Typically, but not necessarily, anchor 2332 comprises a biocompatible material such as stainless steel 316 LVM. For some applications, anchor 2332 comprises nitinol. For some applications, anchor 2332 is coated with a non-conductive material.

Reference is now made to FIGS. 1-23B. It is to be noted that any sleeve 26 shown in any of the figures shown herein, e.g., FIGS. 1A-B, 3-5B, 6G-14, and 20G-21 may be used with any one of the systems described herein.

Figure 24:
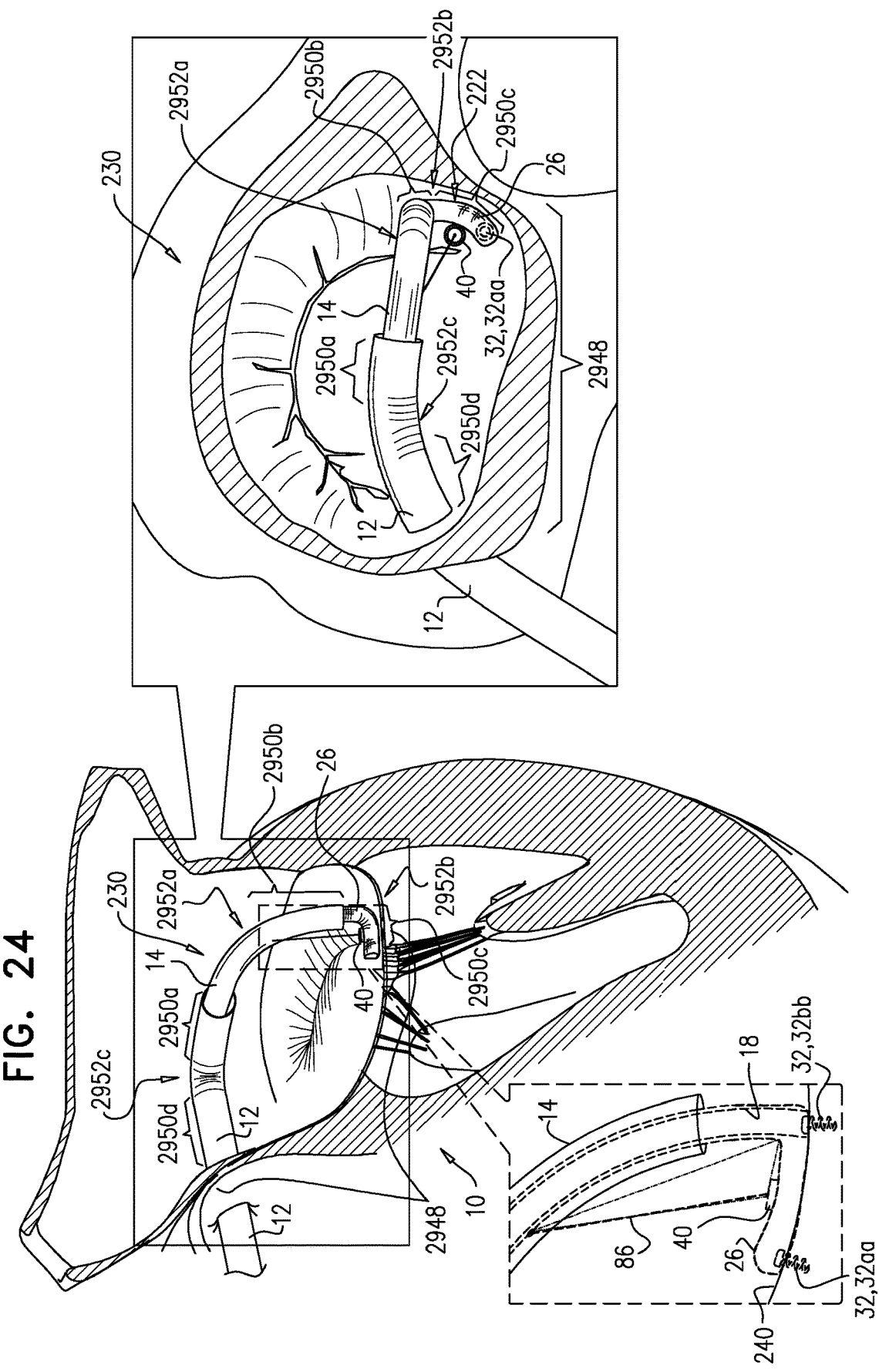
FIG. 24 is a schematic illustration of a state of a distal portion of a multi-component tubular system within the heart of a subject, in accordance with some applications of the invention.

Reference is made to FIG. 24, which is a schematic illustration of a state of a distal portion of system 10 within the heart of a subject, in accordance with some applications of the invention. As generally described hereinabove, (i) catheter 12 is steerable in a first plane, (ii) catheter 14 is steerable in a second plane that is typically perpendicular to the first plane, and (iii) distal portions of sleeve 26 are laid along the annulus of the native valve while proximal portions of the sleeve (and the distal end of manipulator 61, within the sleeve) are disposed at a nonzero angle with respect to the annulus. Thus, system 10 is configured to assume a multi-bend formation 2948 (e.g., handle portion 101 is configured to configure catheter 12, catheter 14, and structure 222 to assume the multi-bend formation) in which at least three domains 2950, and at least two bends 2952 separating the domains, are defined.

The formation includes (i) a first bend 2952a that separates a first domain 2950a of the formation from a second domain 2950b of the formation, and (ii) a second bend 2952b that separates the second domain from a third domain 2950c of the formation. Typically, the formation further includes a third bend 2952c that separates first domain 2950a from a fourth domain 2950d of the formation. First domain 2950a comprises at least (1) part of catheter 12 and (2) part of catheter 14 (i.e., at least a part of catheter 14 disposed within catheter 12), and typically further comprises at least part of sleeve 26 (i.e., at least part of sleeve 26 disposed within catheter 14). Second domain 2950b comprises at least part of catheter 14 (e.g., distal end portion 114 thereof), and at least part of sleeve 26 (e.g., the second domain comprises at least part of sleeve 26 disposed within a portion of catheter 14 that is exposed from catheter 12). Third domain 2950c comprises at least part of sleeve 26, and none of catheters 12 or 14 (i.e., the third domain comprises part of sleeve 26 that is disposed out of the distal end of catheter 14). In applications in which formation 2948 includes third bend 2952c and fourth domain 2950d, the fourth domain comprises at least (1) part of catheter 12 and (2) part of catheter 14 (i.e., at least a part of catheter 14 disposed within catheter 12), and may further comprise at least part of sleeve 26 (i.e., at least part of sleeve 26 disposed within catheter 14). Thus, domains 2950a and 2950d are typically of similar composition, but separated by third bend 2952c.

Thus, the proximal extracorporeal handle portion 101 may be considered to be configured:
  to facilitate sliding of the catheter 14 within catheter 12, and sliding of the structure 222 within catheter 14,
  to drive at least (i) part of catheter 12 and (ii) part of catheter 14 to define first domain 2950a,
  to drive at least part of catheter 14 that is disposed outside of catheter 12 to define second domain 2950b,
  to drive system 10 to define third domain 2950c from sleeve 26, and
  typically, to drive at least (i) part of catheter 12 and (ii) part of catheter 14 to define fourth domain 2950d.

As shown, during anchoring of sleeve 26 (e.g., typically during anchoring of a second anchor 32bb), a generally-triangular shape is formed between: (1) guide member 86, (2) a distal portion of sleeve 26, and (3) channel 18 surrounded partially by catheter 14. It is to be noted that the illustrated triangle is shown in phantom to indicate the relative triangular orientation of the three components, and that the illustrated triangle is not a part of the apparatus shown. For example, a generally-triangular shape is formed in the apparatus between: (1) the guide member, (2) the distal portion of the implant structure at at least a portion of the third domain, and (3) at least a portion of the second domain.

Reference is now made to FIGS. 6A-I, 20A-I, and 24. It is to be noted that techniques for implantation of structure 222 for creating the multi-bend structure shown in FIG. 24 may be employed in techniques described for implantation of ring 3022 in FIGS. 6A-I and in techniques described for implantation of structure 222 in FIGS. 20A-I. For example, the multi-bend formation 2948 is shown in FIG. 6H.

Reference is now made to FIGS. 6H and 24. When system 10 forms multi-bend formation 2948, a first-deployed tissue anchor 32aa anchors a distal end portion of the longitudinal implant (i.e., ring 3022 in FIG. 6H and structure 222 in FIG. 24) to tissue of the subject. Tissue anchor 32aa facilitates the formation of second bend 2952b before and during placement of a second-deployed anchor 32bb by applying a reference force to the implant at the distal end portion of the implant. Additionally, the tube that is disposed within the sleeve 26 (i.e., manipulator 61 in FIG. 6H and channel 18 in FIG. 24) facilitates the formation of second bend 2952b before and during placement of a second-deployed anchor 32bb by applying a reference force to the implant along the second domain 2950b.

Reference is made to FIGS. 6A-I and 24. It is to be noted that annuloplasty ring 3022 of FIGS. 6A-I can be used in the procedure as described in FIG. 24, and structure 222 of FIG. 24 can be used in the procedure as described in FIGS. 6A-I. Additionally, manipulator 61 of FIGS. 6A-I can be used in the procedure as described in FIG. 24, and channel 18 of FIG. 24 can be used in the procedure as described in FIGS. 6A-I. Reference is now made to FIGS. 15A-E, 22A-D, and 24. FIGS. 15A-E describe a first locking mechanism of system 10. The first locking mechanism is located at respective distal portions of outer catheter 12 and guide catheter 14. The first locking mechanism is configured to rotationally lock catheter 12 with respect to catheter 14 at their respective distal portions. For example, and as shown, the first locking mechanism comprises (1) first coupling 152 (e.g., slit 52) at the distal portion of outer catheter 12, and (2) second coupling 154 (e.g., depressible engager 54 comprising a detent) at the distal portion of guide catheter 14. FIGS. 22A-D describe a second locking mechanism of system 10 and how it functions together with the first locking mechanism at the distal end of catheters 12 and 14. The second locking mechanism is located at the proximal extracorporeal handle portion 101 at respective proximal portions of outer catheter 12 and guide catheter 14. The second locking mechanism is configured to rotationally lock catheter 12 with respect to catheter 14 at their respective proximal portions and at the proximal extracorporeal handle portion 101. For example, and as shown, the second locking mechanism comprises (1) housing 1702 shaped to define a groove 1704, and (2) protrusion 1724 at a proximal portion of catheter 14 for engaging groove 1704 of housing 1702 of the second locking mechanism to lock the guide catheter 14 to outer catheter 12. For some applications, the first and the second locking mechanisms are configured to lock substantially simultaneously.

The first and second locking mechanisms enable steering of the distal portion of the catheter 14 in any one or more suitable planes with respect to the distal portion of catheter 12 in a manner which substantially maintains the spatial, angular, and rotational orientation of catheter 12 during the steering of catheter 14. In such a manner, for example, the first and second locking mechanisms enable catheters 12 and 14 to assume multi-bend formation 2948 shown in FIG. 24.

With such a rotational locking provided by the first and/or second locking mechanism, during steering of catheter 14, catheter 14 will not tend to assume the rotational configuration and angular, curved orientation of catheter 12, and vice versa. Additionally, catheter 12 may be further steered without substantially disrupting the spatial, angular, and rotational orientation of the distal portion of catheter 14, and vice versa.

Figure 25:
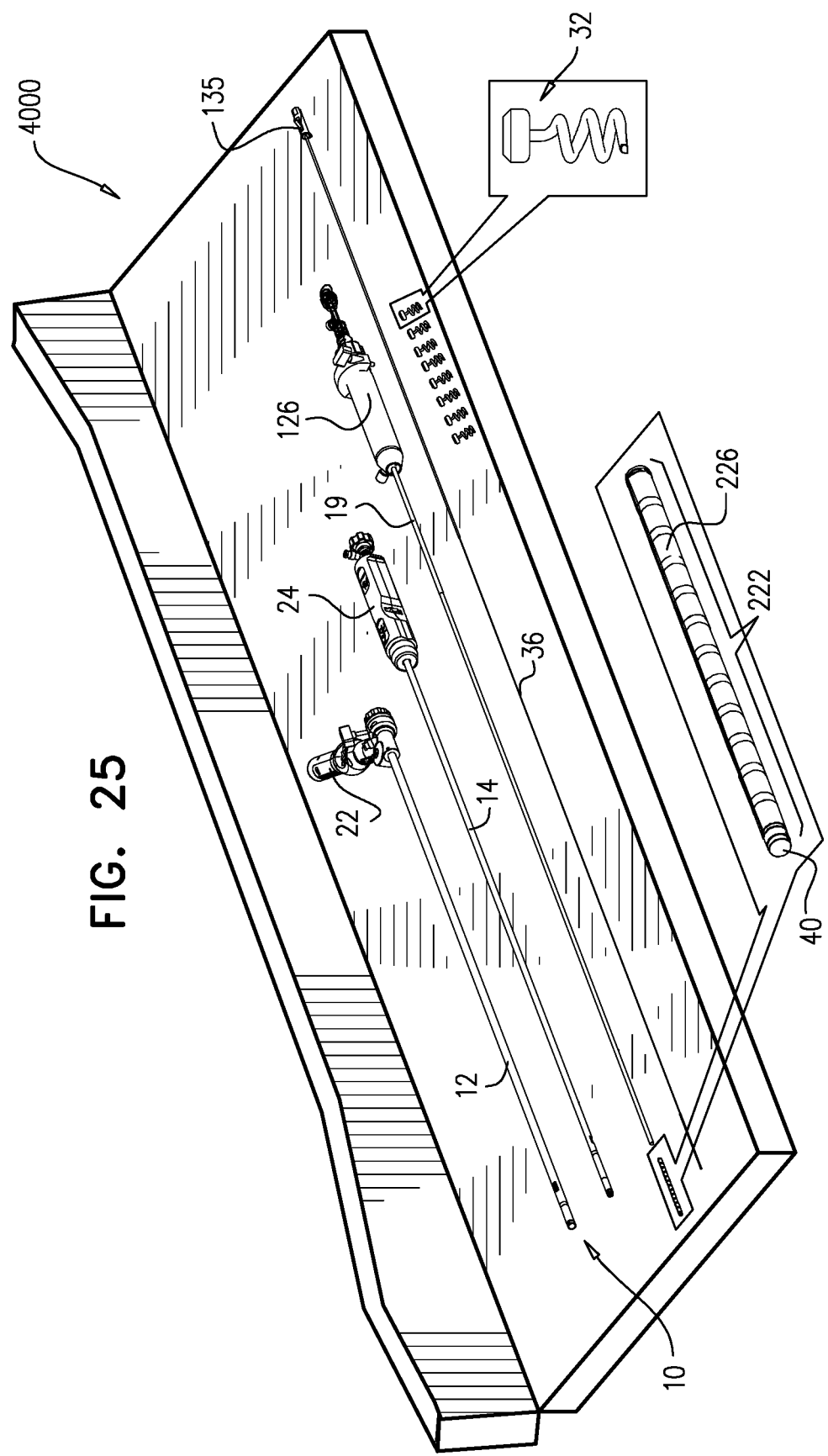
FIG. 25 is a schematic illustration of a kit of components of the catheter system of FIGS. 13-14, in accordance with some applications of the invention.

Reference is now made to FIG. 25, which is a schematic illustration of a kit 4000 comprising components of multi-component tubular system 10, in accordance with some applications of the present invention. As shown, kit 4000 comprises the components shown hereinabove with reference to FIGS. 13 and 14. That is, kit comprises catheter 12 coupled to handle 22, catheter 14 coupled to handle 24, handle 126 coupled to reference-force tube 19 (housing channel 18, not shown), annuloplasty ring structure 222 comprising sleeve 26 and mechanism 40, anchor driver 36 coupled to housing 135, and a plurality of tissue anchors 32. It is to be noted that although FIG. 25 shows a portion of the reference numbers shown in FIGS. 13 and 14, kit 4000 comprises all of the components described hereinabove with reference to FIGS. 13-19B and 22A-23C.

As shown, kit 4000 comprises a single anchor driver 36. It is to be noted that for some applications, a single driver 36 is configured to anchor all of anchors 32 by being reloaded with each anchor subsequently to deploying the previous anchor 32. That is, anchor driver 36 is removed from the body subsequently to deploying each anchor 32. For other applications, driver 36 comprises an anchor storage unit. That is, anchor driver 36 is not removed from the body subsequently to deploying each anchor 32, only after the last anchor is deployed. Alternatively, for some applications, kit 4000 comprises a plurality of anchor drivers 36 coupled to a plurality of anchors 32, respectively.

Kit 4000 comprises a kit for repairing a cardiac valve. As described hereinabove, catheter 14 sized for delivery through vasculature of a subject (i.e., typically through catheter 12). Catheter 14 defines a delivery passage (e.g., its lumen) and has an elongated catheter axis extending therethrough. Structure 222 an elongated and flexible annuloplasty structure which comprises sleeve 26 having an elongated lumen therein. Structure 222 has a structure axis extending along the lumen. Structure 222 is sized and configured for delivery to the heart through catheter 14 substantially along the catheter axis of catheter 14 while the structure axis is substantially parallel to the catheter axis. One or more of anchors 32 (e.g., a plurality, as shown) are configured for delivery to a region of cardiac tissue from a proximal end of catheter 14 (e.g., through channel 18) toward a distal end of catheter 14 and substantially along the structure axis of structure 222 and the catheter axis of catheter 14 at the distal end of catheter 14 while at least a portion of annuloplasty structure 222 is within the passage of catheter 14, as shown in FIGS. 20G-H.

Reference is now made to FIGS. 2-3, 6A-11, and 25. For some applications, sheath 2104 functions as catheter 14. That is, anchors 32 are delivered through a portion of a wall of sleeve 26 while at least a portion of annuloplasty ring 3022 is within a lumen of sheath 2104.

Reference-force tube 19 houses channel 18 (not shown), which comprises an elongated and flexible anchor delivery channel sized and configured to extend within the lumen of structure 222 while at least a portion of structure 222 is within the passage of catheter 14. For some applications, the channel is steerable.

For some applications, channel 18 is configured to be advanced with structure 222 during a period when catheter 14 is maintained in a substantially constant position.

Kit 4000 comprises handle 24 which defines a first control mechanism, and handle 126 which defines a second control mechanism. The first and the second control mechanisms are configured to enable independent movement and steering of catheter 14 channel 18, respectively. Typically, the first control mechanism and the second control mechanism are configured to enable incremental release of the annuloplasty structure from a distal end of channel 18 as the plurality of anchors are sequentially deployed from within channel 18. Typically, the plurality of anchors 32 are configured for location within channel 18 (e.g., each anchor at different times), a distal end of channel 18 is configured for location within the lumen of structure 222, and structure 222 is configured for location at least partially within the lumen of catheter 14.

As shown, kit 4000 comprises catheter 12 which defines an elongated introducer shaft sized for delivery through the vasculature, the introducer shaft defining a lumen and having an elongated shaft axis extending therethrough, wherein the lumen is sized and configured to hold at least a portion of catheter 14 therein while the catheter axis is substantially parallel to the shaft axis (i.e., the axis of catheter 12). Handle 22 defines a catheter control mechanism and a introducer control mechanism configured to enable independent movement of catheter 12 and the introducer shaft. As described hereinabove with reference to FIGS. 13-15E and 22A-D, catheter 12 is shaped so as to define first coupling 152 is shaped so as to define slit 52 for receiving engager 54 comprising a detent). Such first coupling 152 defines a first locking mechanism located at a distal region of catheter 12. A second locking mechanism is also provided for catheter 12, that is, protrusion-locking location 1708 of housing 1702, described hereinabove with reference to FIGS. 22A-D. This second locking mechanism is located at a proximal region of catheter 12. The first and the second locking mechanisms are configured to inhibit rotation of catheter 14 within the lumen of catheter 12.

For some applications, the first and the second locking mechanisms are configured to lock substantially simultaneously.

Although annuloplasty ring 3022 and ring structure 222 is described hereinabove as being placed in an atrium, for some application the ring is instead placed in either the left or right ventricle.

Accordingly, it is noted that, annuloplasty ring 3022 and annuloplasty ring structure 222 and other components of system 10 described hereinabove and methods shown in the application can be used on any cardiac valve (e.g., the mitral, tricuspid, aortic, and/or pulmonary).

Although annuloplasty ring 3022 and structure 222 have been described hereinabove as comprising a partial annuloplasty ring, in some applications of the present invention, the ring instead comprises a full annuloplasty ring.

Reference is now made to FIG. 26, which is a schematic illustration of a stiffening element 1926, in accordance with some applications of the present invention. Stiffening element 1926 is threaded through sleeve 26, so as to provide controllably-variable stiffness to sleeve 26. For example, one or more generally stiff stiffening elements 1926, e.g., a wire or a suture, is woven one or more times (e.g., a plurality of times) through sleeve 26 to provide the stiffness, and subsequently be removed at the conclusion of the implantation procedure when the stiffness is no longer useful.

Since channel 18 and components that are slidable therein are deflectable and steerable, stiffening element 1926 helps maintain the relative positioning of channel 18 with respect to sleeve 26 in order to prevent channel 18 of the deployment manipulator from deploying an anchor through sleeve 26 in a vicinity of contracting member 226 (shown in FIG. 14). That is, stiffening element 1926 helps maintain the shape and integrity of sleeve 26 (e.g., prevents flailing and/or kinking of sleeve 26). Stiffening element 1926 helps ensure that the anchors are deployed through sleeve 26 without interfering with contracting member 226. For some applications, stiffening element 1926 additionally or alternatively facilitates positioning of portions of sleeve 26 and/or anchors 32, such as positioning of subsequent portions and/or anchors following positioning of previous portions and/or anchors.

For some applications, element 1926 is removed from sleeve 26 by being pulled by an operating physician, e.g., using a tool. For other applications, element 1926 is coupled to another portion of system 10, such as a portion of channel 18, the deployment manipulator, or a component that is slidable within a lumen of the deployment manipulator, and is removed by being pulled either by the channel or the manipulator or any component thereof. For some applications, stiffening element 1926 (e.g., a proximal end thereof) is coupled to reference-force tube 19, and is pulled out of sleeve 26 (e.g., unthreaded from the sleeve) following release of the sleeve, as tube 19 is withdrawn proximally (e.g., as shown in blow-up B).

For some applications, stiffening element 1926 may comprise more than one component, at least one of the components being removed from sleeve 26, and at least one of the components remaining within the sleeve. For some applications, such stiffening elements may facilitate loading of the stiffening element into sleeve 26, removal of the stiffening element (or an element thereof) from the sleeve. For example, stiffening element 1926 may comprise a relatively flexible tube, and a relatively stiff rod within the tube, the rod being pulled out of the tube in order to reduce the stiffness of the stiffening element and the sleeve. For some applications, stiffening element 1926 may comprise a plurality of relatively stiff tubes, arranged in series, and a longitudinal member (e.g., a wire or a suture) disposed through the tubes, and fixedly coupled to at least one of the tubes (e.g., a tube at the end of the series). When the longitudinal member is under tension, the tubes are held together (e.g., resembling one long tube), and the stiffening element is generally stiff along its overall length. When the longitudinal member is released and/or removed, the tubes may separate, and although each tube remains relatively stiff, the stiffening element becomes less stiff along its overall length. For some applications, such a stiffening element resembles a trick collapsing "magic wand."

For some applications, the controllably-variable stiffness of sleeve 26 is provided by stiffening element 1926 becoming less stiff (e.g., without mechanically removing the stiffening element). For example, the stiffening element may be configured to become less stiff and/or to dissolve at least in part over time and/or in response to being disposed within the body of the subject (e.g., due to temperature or body fluids). Alternatively or additionally, the stiffening element may comprise a shape-memory or shape-change material having a transition temperature, the stiffening element being delivered in a configuration (e.g., a shape) that is relatively stiff, and transitioning (e.g., in response to provided electromagnetic, electrical, and/or heat energy) to a configuration (e.g., a shape) that is relative flexible.

Reference-force tube 19 is reversibly coupled and couplable to structure 222, and the lumen of reference-force tube 19 is in fluid communication with the lumen of sleeve 26. Stiffening element 1926 is couplable to sleeve 26 and to reference-force tube 19 such that progressive proximal movement of reference-force tube 19 away from sleeve 26 by unthreading stiffening element 1926 from sleeve 26, which (1) decouples stiffening element 1926 from sleeve 26, (2) decouples stiffening element 1926 from progressively proximal portions of sleeve 26, and (3) reduces the inhibition of the flexibility of progressively proximal portions of sleeve 26.

Figure 27A:
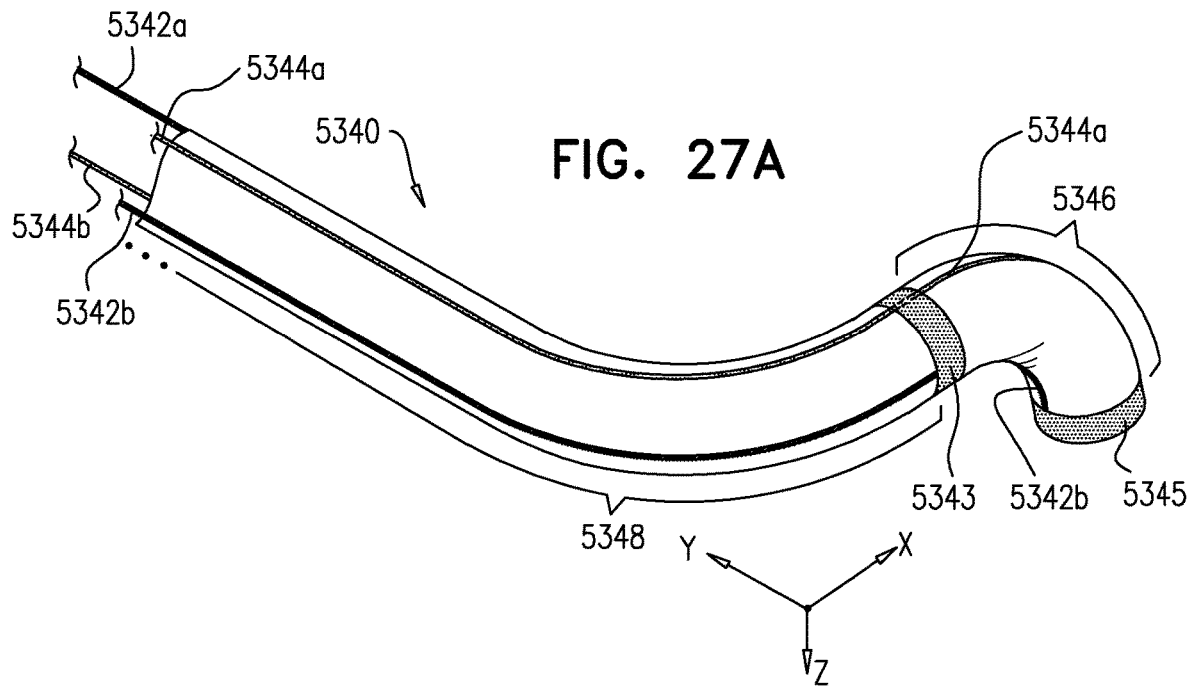
FIGS. 27A-B are schematic illustrations of a steerable catheter having multiple variable steering segments, in accordance with some applications of the present invention.
Figure 27B:
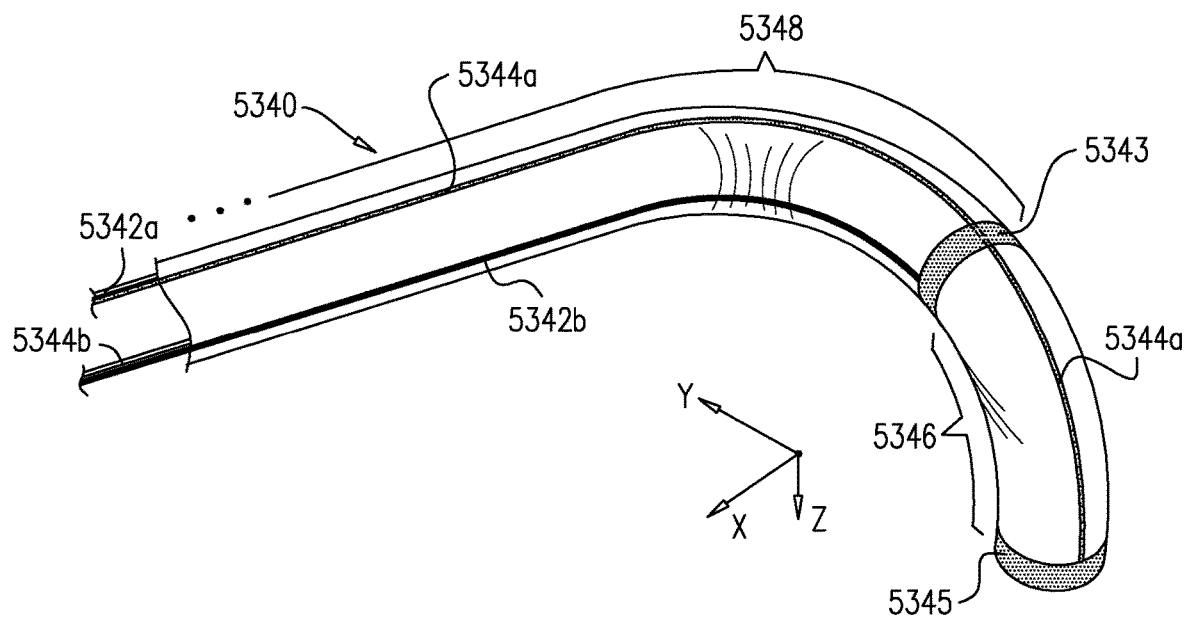

Reference is now made to FIGS. 27A-B, which are schematic illustrations of a catheter 5340 having multiple steering segments (e.g., first and second steering segments 5348 and 5346, respectively), in accordance with some applications of the present invention. First steering segment 5348 comprises a first pull ring 5343 that is coupled to respective distal ends of first and second first-segment steering wires 5342a and 5342b. Steering wires 5342a and 5342b extend from pull ring 5343 toward a proximal portion of catheter 5340. Second steering segment 5346 comprises a second pull ring 5345 that is coupled to respective distal ends of first and second second-segment steering wires 5344a and 5344b. Steering wires 5344a and 5344b extend from the distal end of catheter 5340 toward a proximal portion of catheter 5340.

Segment 5346 is configured to be coupled to only steering wires 5344a and 5344b. Steering wires 5344a and 5344b pass through respective channels provided by pull ring 5343.

In response to the pulling of wires 5342a and 5342b steering segment 5348 is steered in a first plane, and in response to the pulling of wires 5344a and 5344b steering segment 5346 is steered in a second plane, which second plane is at a non-zero angle with respect to the first plane (e.g., generally perpendicular to the first plane). For applications in which catheter 5340 is used to deliver annuloplasty structures 222 and 3022 described herein and anchor driver 36 described herein to a cardiac valve, segment 5348 is configured to be steered in the plane that is parallel with respect to the valve, and segment 5346 is configured to be steered toward the valve in a second plane that is perpendicular with respect to the plane of the valve.

For some applications catheter 5340 may be introduced within multi-component tubular system 10, described hereinabove with reference to FIGS. 13 and 24, in place of catheters 12 and 14. That is reference force tube 19, structure 222, channel 18, and deployment manipulator 61 may be advanced within a lumen of catheter 5340.

Figure 28:
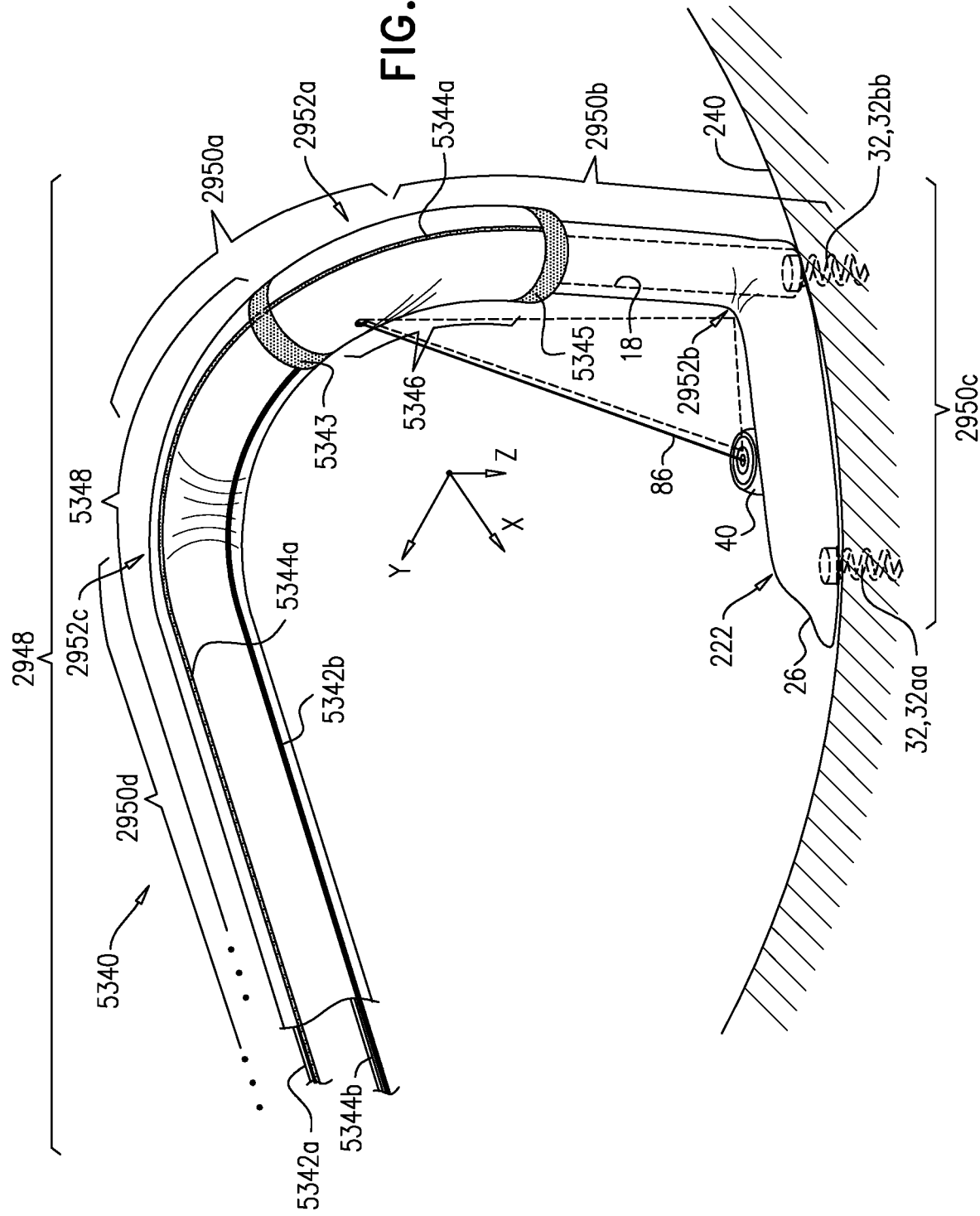
FIG. 28 is a schematic illustration of a state of a distal portion of the steerable catheter of FIGS. 27A-B, in accordance with some applications of the invention.

Reference is made to FIG. 28, which is a schematic illustration of a state of a distal portion of catheter 5340, in accordance with some applications of the invention. The distal portion of catheter 5340 is steerable (i) in a first plane, and (2) in a second plane that is typically perpendicular to the first plane, and (iii) distal portions of sleeve 26 are laid along the annulus 240 of the native valve while proximal portions of the sleeve (and the distal end of manipulator 61, within the sleeve) are disposed at a nonzero angle with respect to the annulus. Thus, catheter 5340 is configured to assume multi-bend formation 2948 (e.g., a proximal extracorporeal handle portion is configured to configure catheter 5340 and structure 222 to assume the multi-bend formation) in which at least three domains 2950, and at least two bends 2952 separating the domains, are defined.

The formation includes (i) a first bend 2952a that separates a first domain 2950a of the formation from a second domain 2950b of the formation, and (ii) a second bend 2952b that separates the second domain from a third domain 2950c of the formation. Typically, the formation further includes a third bend 2952c that separates first domain 2950a from a fourth domain 2950d of the formation. First domain 2950a comprises at least (1) a distal part of steering segment 5348, and (2) typically further comprises at least part of sleeve 26 (i.e., at least part of sleeve 26 disposed within catheter 5340). Second domain 2950b comprises at least part of steering segment 5346 and at least a middle part of sleeve 26 (e.g., the second domain comprises at least part of sleeve 26 disposed within a distal end portion of catheter 5340 and that is exposed from catheter 5340) and none of steering segment 5348. Third domain 2950c comprises at least part of sleeve 26, and none of catheter 5340 (i.e., the third domain comprises a distal part of sleeve 26 that is disposed out of the distal end of catheter 5340). In applications in which formation 2948 includes third bend 2952c and fourth domain 2950d, the fourth domain comprises at least part of catheter 5340 at steering segment 5348 that is proximal to bend 2952c and may further comprise at least part of sleeve 26 (i.e., at least a proximal part of sleeve 26 disposed within catheter 5340). Thus, domains 2950a and 2950d are typically of similar composition, but separated by third bend 2952c.

As shown, during anchoring of sleeve 26 (e.g., typically during anchoring of a second anchor 32bb), a generally-triangular shape is formed between: (1) guide member 86, (2) a distal portion of sleeve 26, and (3) channel 18 surrounded partially by catheter 5340. It is to be noted that the illustrated triangle is shown in phantom to indicate the relative triangular orientation of the three components, and that the illustrated triangle is not a part of the apparatus shown. For example, a generally-triangular shape is formed in the apparatus between: (1) the guide member, (2) the distal portion of the implant structure at at least a portion of the third domain, and (3) at least a portion of the second domain.

Reference is now made to FIGS. 6A-I, 20A-I, and 28. It is to be noted that techniques for implantation of structure 222 for creating the multi-bend structure shown in FIG. 28 may be employed in techniques described for implantation of ring 3022 in FIGS. 6A-I and in techniques described for implantation of structure 222 in FIGS. 20A-I. For example, the multi-bend formation 2948 is shown in FIG. 6H.

Reference is now made to FIGS. 6H and 28. When catheter 5340 forms multi-bend formation 2948, a first-deployed tissue anchor 32aa anchors a distal end portion of the longitudinal implant (i.e., ring 3022 in FIG. 6H and structure 222 in FIG. 24) to tissue of the subject. Tissue anchor 32aa facilitates the formation of second bend 2952b before and during placement of a second-deployed anchor 32bb by applying a reference force to the implant at the distal end portion of the implant. Additionally, the tube that is disposed within the sleeve 26 (i.e., manipulator 61 in FIG. 6H and channel 18 in FIG. 28) facilitates the formation of second bend 2952b before and during placement of a second-deployed anchor 32bb by applying a reference force to the implant along the second domain 2950b.

Reference is made to FIGS. 6A-I and 28. It is to be noted that annuloplasty ring 3022 of FIGS. 6A-I can be used in the procedure as described in FIG. 28, and structure 222 of FIG. 28 can be used in the procedure as described in FIGS. 6A-I. Additionally, manipulator 61 of FIGS. 6A-I can be used in the procedure as described in FIG. 28, and channel 18 of FIG. 28 can be used in the procedure as described in FIGS. 6A-I.

In some applications of the present invention, system 10 is used to treat an atrioventricular valve other than the mitral valve, i.e., the tricuspid valve. In these embodiments, annuloplasty ring 3022, structure 222, and other components of system 10 described hereinabove as being placed in the left atrium are instead placed in the right atrium. Although annuloplasty ring 3022 and structure 222 are described hereinabove as being placed in an atrium, for some application the ring is instead placed in either the left or right ventricle.

Additionally, the scope of the present invention includes embodiments described in the following applications, which are incorporated herein by reference. In an embodiment, techniques and apparatus described in one or more of the following applications are combined with techniques and apparatus described herein:

U.S. patent application Ser. No. 12/341,960 to Cabiri, entitled, "Adjustable partial annuloplasty ring and mechanism therefor," filed on Dec. 3022, 2008, which published as US Patent Application Publication 2010/0161047 and issued as U.S. Pat. No. 8,241,351;

U.S. patent application Ser. No. 12/435,291 to Maisano et al., entitled, "Adjustable repair chords and spool mechanism therefor," filed on May 4, 2009, which published as US Patent Application Publication 2010/0161041 and issued as U.S. Pat. No. 8,147,542;

U.S. patent application Ser. No. 12/437,103 to Zipory et al., entitled, "Annuloplasty ring with intra-ring anchoring," filed on May 7, 2009, which published as US Patent Application Publication 2010/0286767, and which issued as U.S. Pat. No. 8,715,342;

U.S. patent application Ser. No. 12/548,991 to Maisano et al., entitled, "Implantation of repair chords in the heart," filed on Aug. 27, 2009, which published as US Patent Application Publication 2010/0161042, and which issued as U.S. Pat. No. 8,808,368;

PCT Patent Application PCT/IL2009/001209 to Cabiri et al., entitled, "Adjustable annuloplasty devices and mechanisms therefor," filed on Dec. 3022, 2009, which published as PCT Publication WO 10/073246;

PCT Patent Application PCT/IL2010/000357 to Maisano et al., entitled, "Implantation of repair chords in the heart," filed on May 4, 2010, which published as WO 10/128502;

PCT Patent Application PCT/IL2010/000358 to Zipory et al., entitled, "Deployment techniques for annuloplasty ring and over-wire rotation tool," filed on May 4, 2010, which published as WO 10/128503; and/or PCT Patent Application PCT/IL2012/050451 to Sheps et al., entitled, "Controlled steering functionality for implant-delivery tool," filed on Nov. 8, 2012, and which published as WO 13/069019.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A system for repairing a cardiac valve, the system comprising:
   a catheter sized for delivery through vasculature of a subject, the catheter defining a delivery passage and having an elongated catheter axis extending therethrough;

an elongated and flexible annuloplasty structure having an elongated lumen and an annuloplasty structure axis extending along the lumen, wherein the annuloplasty structure is sized and configured for delivery to a heart of the subject through the catheter substantially along the catheter axis while the annuloplasty structure axis is substantially parallel to the catheter axis; and a plurality of anchors, configured for delivery, from a proximal end of the catheter toward the annuloplasty structure and the heart and substantially along the annuloplasty structure axis and the catheter axis while at least a portion of the annuloplasty structure is within the delivery passage of the catheter.

2. The system according to claim 1, further comprising an elongated and flexible anchor delivery channel sized and configured to extend within the annuloplasty structure lumen while at least a portion of the annuloplasty structure is within the delivery passage of the catheter.

3. The system according to claim 2, wherein the channel is steerable.

4. The system according to claim 2, further comprising a first control mechanism and a second control mechanism, wherein the first and the second control mechanisms are configured to enable independent movement of the catheter and the anchor delivery channel, respectively.

5. The system according to claim 4, wherein the anchor delivery channel is configured to be advanced with the annuloplasty structure during a period when the catheter is maintained in a substantially constant position.

6. The system according to claim 4, wherein the first control mechanism and the second control mechanism are configured to enable incremental release of the annuloplasty structure from a distal end of the channel as the plurality of anchors are sequentially deployed from the anchor delivery channel.

7. The system according to claim 2, wherein the plurality of anchors are configured for location within the anchor delivery channel, a distal end of the anchor delivery channel is configured for location within the annuloplasty structure lumen, and the annuloplasty structure is configured for location within the delivery passage of the catheter.

8. The system according to claim 1, wherein the cardiac valve is a mitral valve.

9. The system according to claim 1, further comprising an elongated introducer shaft sized for delivery through the vasculature, the introducer shaft defining an introducer shaft lumen and having an elongated shaft axis extending therethrough, wherein the introducer shaft lumen is sized and configured to hold at least a portion of the catheter therein while the catheter axis is substantially parallel to the shaft axis.

10. The system according to claim 9, further comprising a catheter control mechanism and an introducer control mechanism configured to enable independent movement of the catheter and the introducer shaft.

11. The system according to claim 9, further comprising a first locking mechanism located at a distal region of the catheter and a second locking mechanism located at a proximal region of the catheter, wherein the first and the second locking mechanisms are configured to inhibit rotation of the catheter.

12. The system according to claim 11, wherein the first locking mechanism comprises a detent.

13. The system according to claim 12, wherein the first and the second locking mechanisms are configured to lock substantially simultaneously.

14. The system according to claim 1, wherein the annuloplasty structure comprises a sleeve that has a wall, the elongated lumen being an elongated lumen of the sleeve, and wherein the plurality of anchors are configured to penetrate and pass though material of the wall of the sleeve.

15. The system according to claim 14, wherein each one of the plurality of anchors is deliverable through the elongated lumen of the sleeve and is configured to penetrate and pass through the material of the wall of the sleeve from within the elongated lumen of the sleeve.

16. A method for repairing a cardiac valve, the method comprising:

advancing a catheter through vasculature of a subject, the catheter defining a delivery passage and having an elongated catheter axis extending therethrough;

delivering an elongated and flexible annuloplasty structure to a heart of the subject through the catheter substantially along the catheter axis while the annuloplasty structure axis is substantially parallel to the catheter axis, the elongated and flexible annuloplasty structure having an elongated lumen and an annuloplasty structure axis extending along the lumen; and anchoring the annuloplasty structure to cardiac tissue by delivering a plurality of anchors from a proximal end of the catheter, toward the annuloplasty structure and the heart and substantially along the annuloplasty structure axis and the catheter axis while at least a portion of the annuloplasty structure is within the delivery passage of the catheter.

17. The method according to claim 16, wherein the cardiac valve is a mitral valve.

18. The method according to claim 16, wherein the annuloplasty structure comprises a sleeve that has a wall, the elongated lumen being an elongated lumen of the sleeve, and wherein anchoring the annuloplasty structure to cardiac tissue comprises penetrating and passing each one of the plurality of tissue anchors though material of the wall of the sleeve.

19. The method according to claim 18, wherein penetrating and passing each one of the plurality of tissue anchors comprises delivering the plurality of tissue anchors through the elongated lumen of the sleeve and penetrating and passing each one of the plurality of tissue anchors through the material of the wall of the sleeve from within the elongated lumen of the sleeve.

* * * * *